US010953001B2

(12) United States Patent
Brownstein

(10) Patent No.: US 10,953,001 B2
(45) Date of Patent: *Mar. 23, 2021

(54) METHODS FOR TREATING POST TRAUMATIC STRESS DISORDER

(71) Applicant: Azevan Pharmaceuticals, Inc., Bethlehem, PA (US)

(72) Inventor: Michael J. Brownstein, Rockville, MD (US)

(73) Assignee: Azevan Pharmaceuticals, Inc., Bethlehem, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/987,053

(22) Filed: May 23, 2018

(65) Prior Publication Data

US 2019/0099410 A1 Apr. 4, 2019

Related U.S. Application Data

(63) Continuation of application No. 15/134,549, filed on Apr. 21, 2016, now Pat. No. 9,987,265, which is a continuation of application No. 13/807,613, filed as application No. PCT/US2011/042785 on Jul. 1, 2011, now Pat. No. 9,376,424.

(60) Provisional application No. 61/360,686, filed on Jul. 1, 2010.

(51) Int. Cl.
| | |
|---|---|
| A61K 31/4545 | (2006.01) |
| A61K 31/397 | (2006.01) |
| A61K 31/422 | (2006.01) |
| A61K 31/439 | (2006.01) |
| A61K 31/454 | (2006.01) |
| A61K 31/496 | (2006.01) |
| A61K 31/5377 | (2006.01) |
| C07D 413/04 | (2006.01) |
| C07D 413/14 | (2006.01) |
| A61K 31/4178 | (2006.01) |

(52) U.S. Cl.
CPC ........ *A61K 31/4545* (2013.01); *A61K 31/397* (2013.01); *A61K 31/4178* (2013.01); *A61K 31/422* (2013.01); *A61K 31/439* (2013.01); *A61K 31/454* (2013.01); *A61K 31/496* (2013.01); *A61K 31/5377* (2013.01); *C07D 413/04* (2013.01); *C07D 413/14* (2013.01)

(58) Field of Classification Search
CPC .............. A61K 31/4545; A61K 31/397; A61K 31/4178; A61K 31/422; A61K 31/454; A61K 31/496; A61K 31/5377; C07D 413/04; C07D 413/14
USPC .................................................. 514/210.02
See application file for complete search history.

(56) References Cited

U.S. PATENT DOCUMENTS

| | | |
|---|---|---|
| 3,912,743 A | 10/1975 | Christensen |
| 4,007,196 A | 2/1977 | Christensen |
| 4,085,225 A | 4/1978 | Welle |
| 4,136,193 A | 1/1979 | Bogeso |
| 4,314,081 A | 2/1982 | Molloy |
| 4,341,698 A | 7/1982 | Carr |
| 4,352,752 A | 10/1982 | Ojima |
| 4,478,836 A | 10/1984 | Mouzin |
| 4,536,518 A | 8/1985 | Welch, Jr. |
| 4,576,753 A | 3/1986 | Kamiya |
| 4,734,498 A | 3/1988 | Cooper |
| 4,751,299 A | 6/1988 | Sugawara |
| 4,761,501 A | 8/1988 | Husbands |
| 4,772,694 A | 9/1988 | Cooper |
| 4,956,388 A | 9/1990 | Robertson |
| 5,011,472 A | 4/1991 | Aebischer |
| 5,023,252 A | 6/1991 | Hseih |
| 5,246,943 A | 9/1993 | Blankley |
| 5,338,744 A | 8/1994 | Dudley |
| 5,759,865 A | 6/1998 | Bruns |
| 6,054,453 A | 4/2000 | Lohray |
| 6,054,457 A | 4/2000 | Setoi |
| 6,204,260 B1 | 3/2001 | Bruns, Jr. |
| 6,403,632 B1 | 6/2002 | Duan |
| 6,610,680 B1 | 8/2003 | Bruns, Jr. |
| 6,627,625 B1 | 9/2003 | Koppel |
| 7,119,083 B2 | 10/2006 | Bruns, Jr. |
| 7,179,907 B2 | 2/2007 | Eaton |
| 7,268,125 B2 | 9/2007 | Bruns, Jr. et al. |
| 8,048,874 B2 | 11/2011 | Koppel |
| 9,376,424 B2 | 6/2016 | Brownstein |
| 9,597,314 B2 | 3/2017 | Koppel |
| 9,802,925 B2 | 10/2017 | Brownstein |
| 9,987,265 B2 * | 6/2018 | Brownstein .......... A61K 31/397 |
| 2004/0132714 A1 | 7/2004 | Zhou et al. |
| 2004/0266750 A1 | 12/2004 | Bruns |
| 2005/0059650 A1 | 3/2005 | Jones et al. |

(Continued)

FOREIGN PATENT DOCUMENTS

| | | |
|---|---|---|
| CA | 2615813 | 1/2007 |
| CN | 1106802 | 8/1995 |

(Continued)

OTHER PUBLICATIONS

Ferris et al Pharmacology, Biochemistry and Behavior, 2006, 83, 169-174 (Year: 2006).*

Ojima, Iwao, and Hauh-Jyun C. Chen. "Novel and effective routes to optically pure amino acids, dipeptides, and their derivatives via □ ?] actams obtained through asymmetric cycloaddition." Journal of the Chemical Society, Chemical Communications 8 (1987): 625-626.

Petit, Samuel, and G□ ⊚ ard Coquerel. "The amorphous state." Polymorphism: In the Pharmaceutical Industry 10 (2006): 1.

(Continued)

*Primary Examiner* — Yevgeny Valenrod
(74) *Attorney, Agent, or Firm* — Brannon Sowers & Cracraft PC

(57) ABSTRACT

Compounds and compositions are described herein for treating post traumatic stress disorder.

23 Claims, 2 Drawing Sheets

(56) References Cited

U.S. PATENT DOCUMENTS

| | | |
|---|---|---|
| 2006/0217364 A1 | 9/2006 | Bruns |
| 2006/0281728 A1 | 12/2006 | Guillon |
| 2008/0033165 A1 | 2/2008 | Koppel |
| 2008/0076754 A1 | 3/2008 | Xiang |
| 2008/0280870 A1 | 11/2008 | Kopopel |
| 2009/0170825 A1 | 7/2009 | Koppel |
| 2010/0016274 A1 | 1/2010 | Koppel |
| 2010/0137402 A1 | 6/2010 | Ducoux |
| 2010/0317652 A1 | 12/2010 | Bryans |
| 2011/0059935 A1 | 3/2011 | Bruns |
| 2011/0071160 A1 | 3/2011 | Couturier |
| 2017/0174670 A1 | 6/2017 | Brownstein |

FOREIGN PATENT DOCUMENTS

| | | |
|---|---|---|
| CN | 2000504731 | 4/2000 |
| CN | 1272111 | 11/2000 |
| CN | 1606554 A | 4/2005 |
| EP | 0144840 A2 | 6/1985 |
| EP | 0591040 A1 | 4/1994 |
| EP | 1558598 | 8/2005 |
| JP | S6125361 A | 10/1981 |
| WO | 9316609 A1 | 9/1993 |
| WO | 1993016609 | 9/1993 |
| WO | 9401402 A1 | 1/1994 |
| WO | 1994001402 | 1/1994 |
| WO | 9404494 A1 | 3/1994 |
| WO | 1994004494 | 3/1994 |
| WO | 9426735 A1 | 11/1994 |
| WO | 1994026735 | 11/1994 |
| WO | 199730707 A1 | 8/1997 |
| WO | 1997030707 | 8/1997 |
| WO | 200212187 A1 | 2/2002 |
| WO | 2002012187 | 2/2002 |
| WO | 03031407 A2 | 4/2003 |
| WO | 2004037809 | 5/2004 |
| WO | 06061407 A2 | 6/2006 |
| WO | 2006102283 A2 | 9/2006 |
| WO | 2006102308 | 9/2006 |
| WO | 2006123242 | 11/2006 |
| WO | 2007109615 | 9/2007 |
| WO | 101268068 | 9/2008 |
| WO | 2009115685 | 9/2009 |
| WO | 2014127350 | 8/2014 |
| WO | 2015148962 | 10/2015 |
| WO | 2019055913 | 3/2019 |

OTHER PUBLICATIONS

Ojima, Iwao, Takeo Komata, and Xiaogang Qiu. "Asymmetric alkylations of a phenylalanylglycinate equivalent. Novel route to dipeptides bearing. alpha.-alkyl-. alpha.-amino.acid residues." Journal of the American Chemical Society 112.2 (1990): 770-774.

PCT International Search Report for PCT/US2007/006555 completed by the US Searching Authority dated Jun. 16, 2008.

Hakimelahi, 'The Synthesis of Highly Strainerd Monocyclic and Bicyclic Beta-Lactams (delta-carbapenem)' Helvetica Chimica Acta (1982) vol. 65 Fasc. 5 pp. 1378-1384.

Serradeil-Le Gal, C., et al. "Biochemical and pharmacological properties of SR 49059, a new, potent, nonpeptide antagonist of rat and human vasopressin V1a receptors." Journal of Clinical Investigation 92.1 (1993): 224.

PCT International Search Report for PCT/US2007/064309 completed by the US Searching Authority dated Oct. 1, 2007.

Ragner Liedman et al., 'Intrauterine pressure, ischemia markers, and experienced pain during administration of a vasopressin Via receptor antagonist in spontaneous and vasopressin-induced dysmenorrhea]', Acta Obstetricia et Gynecologica. 85: 207-211, (2005).

R. Brouard et al., 'Effect of SR49059, an orally active Via vasopressin receptor antagonist, in the prevention of dysmenorrhoea', British Journal of Obstetrics and Gynecology, May 2000, vol. 107, pp. 614-619.

Ojima, Iwao, and Xiaogang Qiu. "Asymmetric alkylation of chiral. beta.-lactam ester enolates. A new approach to the synthesis of. alpha.-alkylated. alpha.-amino acids." Journal of the American Chemical Society 109.21 (1987): 6537-6538.

Ojima, Iwao, and Hauh-Jyun C. Chen. "Novel and effective routes to optically pure amino acids, dipeptides, and their derivatives via □ ?| actams obtained through asymmetric cycloaddition." Journal of the Chemical Society, Chemical Communications 8 (1987): 625-626.

International Search Report and Written Opinion for PCT/US2007/078451 completed Apr. 23, 2008.

International Search Report and Written Opinion for PCT/US2006/010192 completed Jul. 1, 2008.

STN web20100331X225934.

Japanese Translation of PCT International Application No. 2000-504731.

Japanese Patent Application Laid-open Publication No. 60-112757.

Chemical Abstracts AN:1992:6288, 1990.

Ghosh, M. et al, Journal of the Indian Chemical Society, 1985, 62(6), pp. 457-459.

Petit, Samuel, and G□ ⊘ard Coquerel. "The amorphous state." Polymorphism: In the Pharmaceutical Industry 10 (2006): 1.

International Search Report and Written Opinion for PCT/US2015/023060 completed Jun. 24, 2015.

Sampalis, Fotini, et al. "Evaluation of the effects of Neptune Krill Oil™ on the management of premenstrual syndrome and dysmenorrhea." Alternative medicine review 8.2 (2003): 171-179.

Dickerson, Lori M., Pamela J. Mazyck, and Melissa H. Hunter. "Premenstrual syndrome." American family physician 67.8 (2003): 1743-1752.

Treatment Improvement Protocol (TIP) Series 51. HHS Publication No. (SMA) 09-4426. Rockville, MD: Substance Abuse and Mental Health Services Administration (2009); Appendix E: DSM-IV-TR Criteria for Posttraumatic Stress Disorder.

Ring, Robert H. "The central vasopressinergic system: examining the opportunities for psychiatric drug development." Current pharmaceutical design 11.2 (2005): 205-225.

Simon, N.G. et al., "Novel vasopressin la anta1,>onists for CNS disorders: Development and characterization of clinical candidates", Neuroscience 2011, 1-2.

Fabio, Karine, et al. "Vasopressin antagonists as anxiolytics and antidepressants: Recent developments." Frontiers CNS Drug Discov 1.1 (2010): 156-183.

European Search Report for EP 15769990, dated Oct. 18, 2011.

Lee, Royce J., et al. "A novel V1a receptor antagonist blocks vasopressin-induced changes in the CNS response to emotional stimuli: an fMRI study." Frontiers in systems neuroscience 7 (2013).

Fabio, Karine, et al. "Synthesis and evaluation of potent and selective human V1a receptor antagonists as potential ligands for PET or SPECT imaging." Bioorganic & medicinal chemistry 20.3 (2012): 1337-1345.

Ojima, Iwao, et al., "Asymmetric Alkylation of Chiral (.beta.-Lactam Ester Enolates. A New Approach to the Synthesis of .alpha.-Alkylated alpha.-Amino Acids,," 1987, J. Am. Chem. Soc., Chem. Comm., pp. 6537-6540.

Jarrahpour, A.A., et al., 'Asymmetric Synthesis and Antimicrobial Activity of Some New Mono and Bicyclic .beta.-Lactams,' Molecules, 2004, vol. 9, pp. 939-948.

Jarrahpour, A.A., et al., 'Asymmetric Synthesis of a New Monocyclic beta.-Lactam as a potential biological active compound,' Molecules, 2005, M439.

PCT International Search Report for PCT/US2006/027703, dated Mar. 30, 2007.

PCT International Search Report for PCT/US2006/10192, dated Jul. 1, 2008.

European Search Report for EP 06739075.7, dated Sep. 13, 2011.

Surget et al.: 'Involvement of Vasopressin in Affective Disorders' European Journal Pharmacology vol. 583, 2008, pp. 340-349, XP022532879.

De Kloet et al: "Elevated plasma arginine vasopressin levels in veterans with posttraumatic stress disorder", Journal of Psychiatric

(56) References Cited

OTHER PUBLICATIONS

Research, Elsevier Ltd, GB, vol. 42, No. 3, Dec. 20, 2007 (Dec. 20, 2007), pp. 192-198, XP022395299, ISSN: 0022-3956.
Ferris C F et al: "Orally active vasopressin V1a receptor antagonist, SRX251, selectively blocks aggressive behavior", Pharmacology Biochemistry and Behavior, Elsevier, US, vol. 83, No. 2, Feb. 1, 2006 (Feb. 1, 2006), pp. 169-174, XP027929666, ISSN: 0091-3057 [retrieved on Feb. 1, 2006].
Guillon et al: "Azetidinones as vasopressin V1a antagonists", Bioorganic & Medicinal Chemistry, Pergamon, GB, vol. 15, No. 5, Jan. 31, 2007 (Jan. 31, 2007), pp. 2054-2080, XP005867173, ISSN: 0968-0896, DOI: 10.1016/J.BMC.2006.12.031.
PCT International Search Report for PCT/US04/32401 competed by the U.S. Searching Authority dated Mar. 2, 2005.
Hirai, Koichi, et al. "An Example of the B-Lactam Ring Formation and Pyrrolinoazetidinone Ring Construction," Chemical Research Laboratories, vol. 37, pp. 133-139, 1985.
Office Action for U.S. Appl. No. 10/492,323 dated Nov. 9, 2005, 13 pages.
Office Action for U.S. Appl. No. 10/492,323 dated Mar. 7, 2005, 16 pages.
Office Action for U.S. Appl. No. 11/442,788 dated Nov. 2, 2006, 16 pages.
Office Action for U.S. Appl. No. 11/835,017 dated Apr. 16, 2008, 5 pages.
Bhatia, Subhash C., and Shashi K. Bhatia. "Diagnosis and treatment of premenstrual dysphoric disorder." Am Fam Physician 66.7 (2002): 1239-1249.
Stromberg et al. (Acta Obstetricia et Gynecologica Scandinavica, 63, 6, 533-38), 1984.
Thibonnier, M., et al. "The basic and clinical pharmacology of nonpeptide vasopressin receptor antagonists." Annual review of pharmacology and toxicology 41.1 (2001): 175-202.

\* cited by examiner

METHODS FOR TREATING POST TRAUMATIC STRESS DISORDER

CROSS-REFERENCE TO RELATED APPLICATIONS

This application is a continuation of U.S. patent application Ser. No. 15/134,549, filed Apr. 21, 2016, which issued as U.S. Pat. No. 9,987,265 on Jun. 5, 2018, is a continuation of U.S. patent application Ser. No. 13/807,613, filed Dec. 28, 2012, which issued as U.S. Pat. No. 9,376,424 on Jun. 28, 2016, which is a U.S. national entry application under 37 C.F.R. § 371(b) of International Application Serial No. PCT/US2011/042785 filed Jul. 1, 2011, which claims priority under 35 U.S.C. § 119(e) to U.S. Provisional Application Ser. No. 61/360,686, filed Jul. 1, 2010, the entirety of the disclosure of each of which is expressly incorporated herein by reference.

GOVERNMENT RIGHTS

This invention was made with government support under R44 MH063663 awarded by the National Institutes of Health. The government has certain rights in the invention.

TECHNICAL FIELD

The invention described herein pertains to compounds, compositions, medicaments, and methods for treating post traumatic stress disorder using vasopressin antagonists.

BACKGROUND AND SUMMARY OF THE INVENTION

PTSD is recognized by the Department of Defense, the Department of Veterans Affairs, and the National Institute of Mental Health as a major medical issue for both deployed and returning U.S. troops. In particular, recent studies indicate that the incidence of PTSD among Iraq and Afghanistan veterans is 20% and may reach 35%, which is a rate 4-7 times higher than the general population. PTSD is not only an illness that affects military personnel; the NIMH reports that almost eight million Americans suffer from this disorder and that it ranks among the most common psychiatric conditions in the country. PTSD is characterized by diminished emotional capacity, compromised relationships with family and friends, reduced interest in activities that bring enjoyment, irritability, increased aggression, and sometimes violent behavior. Additional disorders often co-occur with PTSD, including depression, substance abuse, other anxiety disorders, anger and impulsivity disorders, and the like. Like other mental health conditions, the consequences of PTSD extend beyond the patient to their families as well. Not only are there increased long-term medical costs, there also is diminished earning capacity and adverse impacts on quality of life. In combination, these circumstances produce a cycle of spiraling demand for Federal assistance, lost earnings, and escalating, ongoing social and economic costs. Improved treatments for PTSD and depression, especially during the first two years after deployment could reduce medical treatment costs for the US military (projected at $4.0 to $6.2 billion) by 25% to 40%.

Current drug therapies for PTSD rely on existing, repurposed antidepresants and anxiolytics that have not demonstrated sufficient efficacy, include undesirable side effects, and have been recognized to be further limited due to compliance issues; see, for example, Keane, et al. Posttraumatic stress disorder: etiology, epidemiology, and treatment outcome. Annu Rev Clin Psychol, 2: 61-97 (2006); Lader, Effectiveness of benzodiazepines: do they work or not? Expert Rev Neurother, 8(8): 1189-91 (2008); Marks, et al., Paroxetine: safety and tolerability issues. Expert Opin Drug Saf, 7(6):783-94 (2008). The foregoing publications, and each additional publication cited herein is incorporated herein by reference. Whether it is the complexity of PTSD or differences in the underlying neurobiology of the disorder, available drugs offer limited relief. A new approach to pharmacotherapy is needed for significant improvement in clinical outcomes.

It has been discovered herein that PTSD and related diseases and disorders are treatable with selective vasopressin V1a antagonists of the formula

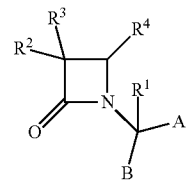

and pharmaceutically acceptable salts thereof, wherein
A is a carboxylic acid, an ester, or an amide;
B is a carboxylic acid, an ester, or an amide; or B is an alcohol or thiol, or a derivative thereof;
$R^1$ is hydrogen or $C_1$-$C_6$ alkyl;
$R^2$ is hydrogen, alkyl, alkenyl, alkynyl, alkoxy, alkylthio, halo, haloalkyl, cyano, formyl, alkylcarbonyl, or a substituent selected from the group consisting of —$CO_2R^8$, —$CONR^8R^{8'}$, and —$NR^8(COR^9)$; where $R^8$ and $R^{8'}$ are each independently selected from hydrogen, alkyl, cycloalkyl, optionally substituted aryl, or optionally substituted arylalkyl; or $R^8$ and $R^{8'}$ are taken together with the attached nitrogen atom to form a heterocyclyl group; and where $R^9$ is selected from hydrogen, alkyl, cycloalkyl, alkoxyalkyl, optionally substituted aryl, optionally substituted arylalkyl, optionally substituted heteroaryl, optionally substituted heteroarylalkyl, and $R^8R^{8'}N$—($C_1$-$C_4$ alkyl);
$R^3$ is an amino, amido, acylamido, or ureido group, which is optionally substituted; or $R^3$ is a nitrogen-containing heterocyclyl group attached at a nitrogen atom; and
$R^4$ is alkyl, alkenyl, alkynyl, cycloalkyl, cycloalkenyl, alkylcarbonyl, optionally substituted aryl, optionally substituted arylalkyl, optionally substituted arylhaloalkyl, optionally substituted arylalkoxyalkyl, optionally substituted arylalkenyl, optionally substituted arylhaloalkenyl, or optionally substituted arylalkynyl.

DETAILED DESCRIPTION

Figure 1A:
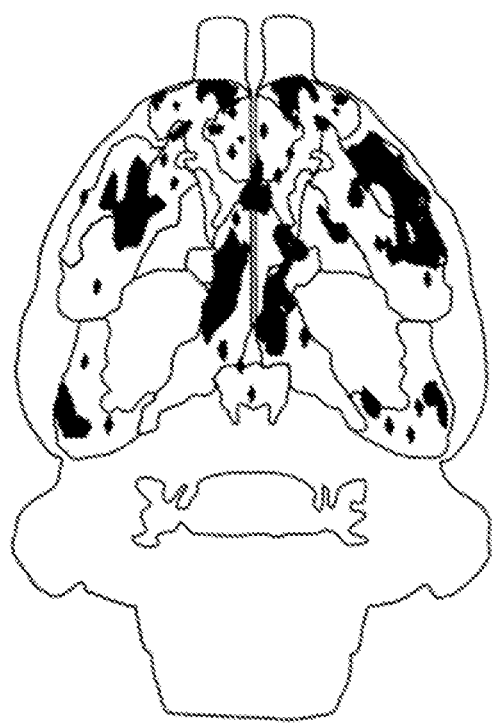
FIG. 1A. shows a 3D representation of the Papez circuit, where areas in black denote the average significant BOLD activation of eight animals for unconditioned pattern of activation for the ferret alone.
Figure 1B:
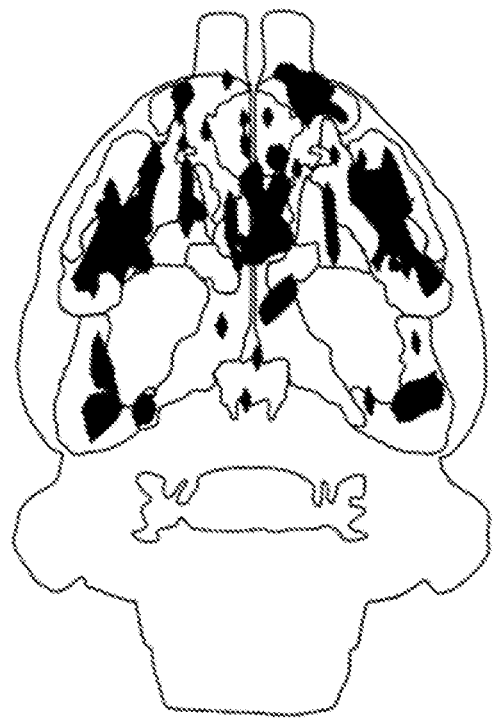
FIG. 1B shows the unconditioned pattern of activation for ferret following pretreatment with AVN576 (5 mg/kg body weight)
Figure 1C:
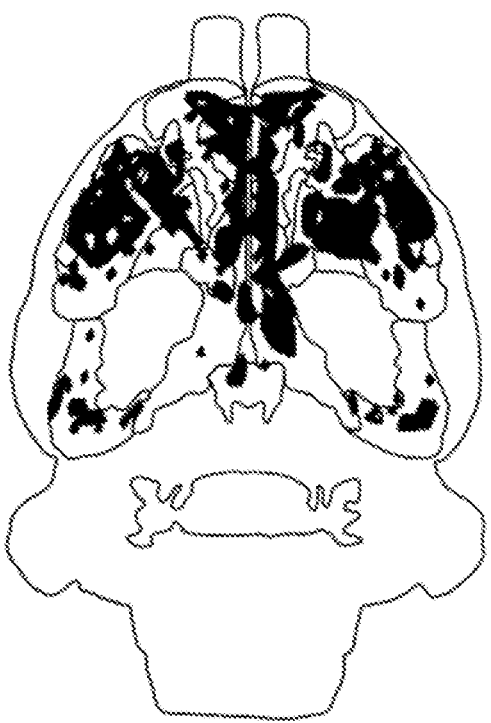
FIG. 1C shows the conditioned activation pattern when the animals are re-exposed to sucrose alone in the magnet two weeks later.
Figure 1D:
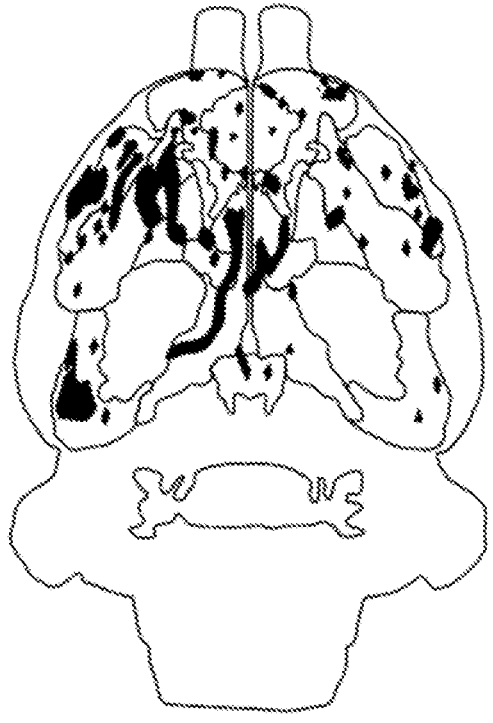
FIG. 1D shows the conditioned activation pattern when animals are pretreated with AVN576 (5 mg/kg body weight), and re-exposed to sucrose alone in the magnet two weeks later.

Described herein is the use of AVP antagonists as a therapeutic approach for treating PTSD. The compounds described herein may have the potential to greatly improve the lives of active military personnel, returning veterans, their families, and the general population by addressing an unmet medical need and reducing the overall economic burden of one of the most common and growing mental health disorders in the United States.

In one illustrative embodiment of the methods described herein, one or more compounds of the formula:

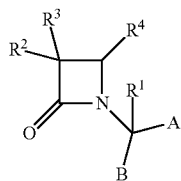

and pharmaceutically acceptable salts thereof, are administered to a patient having PTSD; wherein A is a carboxylic acid, an ester, or an amide;

B is a carboxylic acid, an ester, or an amide; or B is an alcohol or thiol, or a derivative thereof;

$R^1$ is hydrogen or $C_1$-$C_6$ alkyl;

$R^2$ is hydrogen, alkyl, alkenyl, alkynyl, alkoxy, alkylthio, halo, haloalkyl, cyano, formyl, alkylcarbonyl, or a substituent selected from the group consisting of —$CO_2R^8$, —$CONR^8R^{8'}$, and —$NR^8(COR^9)$; where $R^8$ and $R^{8'}$ are each independently selected from hydrogen, alkyl, cycloalkyl, optionally substituted aryl, or optionally substituted arylalkyl; or $R^8$ and $R^{8'}$ are taken together with the attached nitrogen atom to form a heterocyclyl group; and where $R^9$ is selected from hydrogen, alkyl, cycloalkyl, alkoxyalkyl, optionally substituted aryl, optionally substituted arylalkyl, optionally substituted heteroaryl, optionally substituted heteroarylalkyl, and $R^8R^{8'}N$—($C_1$-$C_4$ alkyl);

$R^3$ is an amino, amido, acylamido, or ureido group, which is optionally substituted; or $R^3$ is a nitrogen-containing heterocyclyl group attached at a nitrogen atom; and $R^4$ is alkyl, alkenyl, alkynyl, cycloalkyl, cycloalkenyl, alkylcarbonyl, optionally substituted aryl, optionally substituted arylalkyl, optionally substituted arylhaloalkyl, optionally substituted arylalkoxyalkyl, optionally substituted arylalkenyl, optionally substituted arylhaloalkenyl, or optionally substituted arylalkynyl.

In another illustrative embodiment, one or more compounds of formula (I):

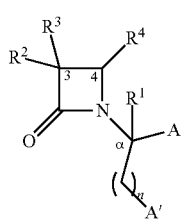

and pharmaceutically acceptable salts thereof, are administered to the patient; wherein A and A' are each independently selected from —$CO_2H$, or an ester or amide derivative thereof;

n is an integer selected from 0 to about 3;

$R^1$ is hydrogen or $C_1$-$C_6$ alkyl;

$R^2$ is hydrogen, alkyl, alkenyl, alkynyl, alkoxy, alkylthio, halo, haloalkyl, cyano, formyl, alkylcarbonyl, or a substituent selected from the group consisting of —$CO_2R^8$, —$CONR^8R^{8'}$, and —$NR^8(COR^9)$; where $R^8$ and $R^{8'}$ are each independently selected from hydrogen, alkyl, cycloalkyl, optionally substituted aryl, or optionally substituted arylalkyl; or $R^8$ and $R^{8'}$ are taken together with the attached nitrogen atom to form an heterocycle; and where $R^9$ is selected from hydrogen, alkyl, cycloalkyl, alkoxyalkyl, optionally substituted aryl, optionally substituted arylalkyl, optionally substituted heteroaryl, optionally substituted heteroarylalkyl, and $R^8R^{8'}N$—($C_1$-$C_4$ alkyl);

$R^3$ is an amino, amido, acylamido, or ureido group, which is optionally substituted; or $R^3$ is a nitrogen-containing heterocyclyl group attached at a nitrogen atom; and $R^4$ is alkyl, alkenyl, alkynyl, cycloalkyl, cycloalkenyl, alkylcarbonyl, optionally substituted aryl, optionally substituted arylalkyl, optionally substituted arylhaloalkyl, optionally substituted arylalkoxyalkyl, optionally substituted arylalkenyl, optionally substituted arylhaloalkenyl, or optionally substituted arylalkynyl.

In another illustrative embodiment, one or more compounds of formula (II):

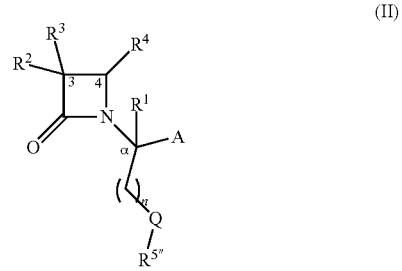

(II)

and pharmaceutically acceptable salts thereof, are administered to the patient; wherein A is —$CO_2H$, or an ester or amide derivative thereof;

Q is oxygen; or Q is sulfur or disulfide, or an oxidized derivative thereof, n is an integer from 1 to 3;

$R^1$, $R^2$, $R^3$, and $R^4$ are as defined in formula I; and $R^{5'}$ is selected from hydrogen, alkyl, cycloalkyl, alkoxyalkyl, optionally substituted arylalkyl, optionally substituted heterocyclyl or optionally substituted heterocyclylalkyl, and optionally substituted aminoalkyl.

In one embodiment of the compounds of formulae (I) or (II), A is —$CO_2R^5$; where $R^5$ is selected from hydrogen, alkyl, cycloalkyl, alkoxyalkyl, optionally substituted arylalkyl, heterocyclyl, heterocyclyl($C_1$-$C_4$ alkyl), and $R^6R^7N$—($C_2$-$C_4$ alkyl). In another embodiment of the compounds of formulae (I) or (II), A is monosubstituted amido, disubstituted amido, or an optionally substituted nitrogen-containing heterocyclylamido.

It is to be understood that in each occurrence of the various embodiments described herein, heterocyclyl is independently selected in each instance. In one illustrative embodiment, heterocyclyl is independently selected from tetrahydrofuryl, morpholinyl, pyrrolidinyl, piperidinyl, piperazinyl, homopiperazinyl, or quinuclidinyl; where said morpholinyl, pyrrolidinyl, piperidinyl, piperazinyl, homopiperazinyl, or quinuclidinyl is optionally N-substituted with $C_1$-$C_4$ alkyl or optionally substituted aryl($C_1$-$C_4$ alkyl).

It is also to be understood that in each occurrence of the various embodiments described herein, $R^6$ and $R^7$ are each independently selected in each instance. In another illustrative aspect, $R^6$ is independently selected from hydrogen or alkyl; and $R^7$ is independently selected in each instance from alkyl, cycloalkyl, optionally substituted aryl, or optionally substituted arylalkyl. In another illustrative aspect, $R^6$ and $R^7$ are taken together with the attached nitrogen atom to form an optionally substituted heterocycle, such as pyrrolidinyl, piperidinyl, morpholinyl, piperazinyl, and homopiperazinyl; where said piperazinyl or homopiperazinyl is also optionally N-substituted with $R^{13}$; where $R^{13}$ is independently selected in each instance from hydrogen, alkyl, cycloalkyl, alkoxycarbonyl, optionally substituted aryloxycarbonyl, optionally substituted arylalkyl, and optionally substituted aryloyl.

In another embodiment, compounds of formula (I) are described where A and/or A' is an amide. In another embodiment, A and A' are amides. In another embodiment, A and/or A' is an amide of a secondary amine, also referred to herein as a secondary amide. In another embodiment, A and A' are both secondary amides. It is to be understood that secondary amides include amides of cyclic amines attached at nitrogen.

In another embodiment, compounds of formula (II) are described where A is an amide. In another embodiment, A is an amide of a secondary amine, also referred to herein as a secondary amide.

In another embodiment, compounds of formula (I) are described that are diesters, acid-esters, or diacids, including pharmaceutically acceptable salts thereof, where each of A and A' is independently selected. In another embodiment, compounds of formula (I) are described that are esteramides, where one of A and A' is an ester, and the other is an amide. In another embodiment, compounds of formula (I) are described that are diamides, where each of A and A' are independently selected from monosubstituted amido, disubstituted amido, and optionally substituted nitrogen-containing heterocyclylamido.

In one variation of the compounds of formula (I), A and/or A' is an independently selected monosubstituted amido of the formula C(O)NHX—, where X is selected from alkyl, cycloalkyl, alkoxyalkyl, optionally substituted aryl, optionally substituted arylalkyl, heterocyclyl, heterocyclyl-($C_1$-$C_4$ alkyl), $R^6R^7N$—, and $R^6R^7N$—($C_2$-$C_4$ alkyl), where each heterocyclyl is independently selected.

In another variation, A and/or A' is an independently selected disubstituted amido of the formula C(O)NR$^{14}$X—, where $R^{14}$ is selected from hydroxy, alkyl, alkoxycarbonyl, and benzyl; and X is selected from alkyl, cycloalkyl, alkoxyalkyl, optionally substituted aryl, optionally substituted arylalkyl, heterocyclyl, heterocyclyl-($C_1$-$C_4$ alkyl), $R^6R^7N$—, and $R^6R^7N$—($C_2$-$C_4$ alkyl), where each heterocyclyl is independently selected.

In another variation, A and/or A' is an amide of an independently selected optionally substituted nitrogen-containing heterocycle attached at a nitrogen. Illustrative nitrogen-containing heterocycles include but are not limited to pyrrolidinyl, piperidinyl, piperazinyl, homopiperazinyl, triazolidinyl, triazinyl, oxazolidinyl, isoxazolidinyl, thiazolidinyl, isothiazolidinyl, 1,2-oxazinyl, 1,3-oxazinyl, morpholinyl, oxadiazolidinyl, and thiadiazolidinyl; each of which is optionally substituted. Such optional substitutions include the groups $R^{10}$, $R^{12}$, $R^6R^7N$—, and $R^6R^7N$—($C_1$-$C_4$ alkyl), as defined herein. In one embodiment, A and/or A' is independently selected from pyrrolidinonyl, piperidinonyl, 2-(pyrrolidin-1-ylmethyl)pyrrolidin-1-yl, or 1,2,3,4-tetrahydroisoquinolin-2-yl, each of which is optionally substituted, and attached at a nitrogen.

In another variation, A and/or A' is an independently selected amide of an optionally substituted piperidinyl attached at the nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))-($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl). In one embodiment, A and/or A' is an independently selected piperidinyl substituted at the 4-position and attached at the nitrogen.

In another variation, A and/or A' is an independently selected amide of an optionally substituted piperazinyl attached at a nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))-($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl). In one embodiment, A and/or A' is an independently selected piperazinyl substituted at the 4-position and attached at a nitrogen.

In another variation, A and/or A' is an independently selected amide of an optionally substituted homopiperazinyl attached at a nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))-($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl). In one embodiment, A and/or A' is an independently selected homopiperazinyl substituted at the 4-position and attached at a nitrogen. In another embodiment, A and/or A' is an independently selected homopiperazinyl substituted at the 4-position with alkyl, aryl, aryl($C_1$-$C_4$ alkyl), and attached at a nitrogen.

In another embodiment of the compounds of formula (I), A' is monosubstituted amido, disubstituted amido, or an optionally substituted nitrogen-containing heterocyclylamido. In another embodiment of the compounds of formula (I), A' is —$CO_2R^{5'}$; where $R^{5'}$ is selected from hydrogen, alkyl, cycloalkyl, alkoxyalkyl, optionally substituted arylalkyl, heterocyclyl, heterocyclyl($C_1$-$C_4$ alkyl), and $R^6R^7N$—($C_2$-$C_4$ alkyl); where heterocyclyl is in each occurrence independently selected from tetrahydrofuryl, morpholinyl, pyrrolidinyl, piperidinyl, piperazinyl, homopiperazinyl, or quinuclidinyl; where said morpholinyl, pyrrolidinyl, piperidinyl, piperazinyl, homopiperazinyl, or quinuclidinyl is optionally N-substituted with $C_1$-$C_4$ alkyl or optionally substituted aryl($C_1$-$C_4$ alkyl). In one variation, $R^{5'}$ is optionally substituted heterocyclylalkyl or optionally substituted aminoalkyl, including $R^6R^7N$—($C_2$-$C_4$ alkyl).

In another embodiment of the compounds of formulae (I) or (II), A is of the formula

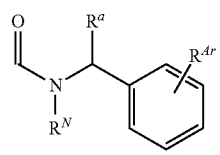

where $R^N$ is hydrogen or optionally substituted alkyl, or an amide prodrug forming group; $R^a$ is hydrogen or optionally substituted alkyl; and $R^{Ar}$ is hydrogen or one or more aryl substituents, such as but not limited to halo, hydroxy, optionally substituted alkyl, optionally substituted alkoxy, nitro, and the like. In another embodiment, at least one of $R^N$, $R^a$, and $R^{Ar}$ is not hydrogen. In another embodiment, at least one of $R^N$ and $R^a$ is not hydrogen. In another embodiment, A is of the formula

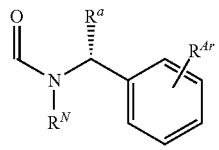

where $R^N$, $R^a$, and $R^{Ar}$ are as defined herein.

In another embodiment, compounds of formula (II) are described wherein A is selected from monosubstituted amido, disubstituted amido, and optionally substituted nitrogen-containing heterocyclylamido. In another embodiment, A is an amide of optionally substituted 1-tetrahydronaphthylamine.

In one variation, A and/or A' is a monosubstituted amido of the formula C(O)NHX, where X is selected from alkyl, cycloalkyl, alkoxyalkyl, optionally substituted aryl, optionally substituted arylalkyl, heterocyclyl, heterocyclyl-($C_1$-$C_4$ alkyl), $R^6R^7N-$, and $R^6R^7N-(C_2$-$C_4$ alkyl), where each heterocyclyl is independently selected.

In another variation, A and/or A' is a disubstituted amido of the formula C(O)NR$^{14}$X, where R$^{14}$ is selected from hydroxy, alkyl, alkoxycarbonyl, and benzyl; and X is selected from alkyl, cycloalkyl, alkoxyalkyl, optionally substituted aryl, optionally substituted arylalkyl, heterocyclyl, heterocyclyl-($C_1$-$C_4$ alkyl), $R^6R^7N-$, and $R^6R^7N-(C_2$-$C_4$ alkyl), where each heterocyclyl is independently selected.

In another variation, A and/or A' is an amide of an optionally substituted nitrogen-containing heterocycle attached at a nitrogen. Illustrative nitrogen-containing heterocycles include but are not limited to pyrrolidinyl, piperidinyl, piperazinyl, homopiperazinyl, triazolidinyl, triazinyl, oxazolidinyl, isoxazolidinyl, thiazolidinyl, isothiazolidinyl, 1,2-oxazinyl, 1,3-oxazinyl, morpholinyl, oxadiazolidinyl, and thiadiazolidinyl; each of which is optionally substituted. Such optional substitutions include the groups $R^{10}$, $R^{12}$, $R^6R^7N-$, and $R^6R^7N-(C_1$-$C_4$ alkyl), as defined herein. In one embodiment, A is pyrrolidinonyl, piperidinonyl, 2-(pyrrolidin-1-ylmethyl)pyrrolidin-1-yl, or 1,2,3,4-tetrahydroisoquinolin-2-yl, each of which is optionally substituted, and attached at a nitrogen.

In another variation, A and/or A' is an amide of an optionally substituted piperidinyl attached at the nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))-($C_2$-$C_4$ alkyl), $R^6R^7N-$, $R^6R^7N$-alkyl, including $R^6R^7N-(C_1$-$C_4$ alkyl), diphenylmethyl, optionally substituted aryl, optionally substituted aryl($C_1$-$C_4$ alkyl), and piperidin-1-yl($C_1$-$C_4$ alkyl). In one embodiment, A and/or A' is piperidinyl substituted at the 4-position and attached at the nitrogen.

In another variation, A and/or A' is an amide of an optionally substituted piperazinyl attached at a nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))-($C_2$-$C_4$ alkyl), $R^6R^7N-$, $R^6R^7N$-alkyl, including $R^6R^7N-(C_1$-$C_4$ alkyl), diphenylmethyl, optionally substituted aryl, optionally substituted aryl($C_1$-$C_4$ alkyl), and piperidin-1-yl($C_1$-$C_4$ alkyl). In one embodiment, A and/or A' is piperazinyl substituted at the 4-position and attached at a nitrogen.

In another variation, A and/or A' is an amide of an optionally substituted homopiperazinyl attached at a nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))-($C_2$-$C_4$ alkyl), $R^6R^7N-$, $R^6R^7N$-alkyl, including $R^6R^7N-(C_1$-$C_4$ alkyl), diphenylmethyl, optionally substituted aryl, optionally substituted aryl($C_1$-$C_4$ alkyl), and piperidin-1-yl($C_1$-$C_4$ alkyl). In one embodiment, A and/or A' is homopiperazinyl substituted at the 4-position and attached at a nitrogen. In another embodiment, A and/or A' is homopiperazinyl substituted at the 4-position with alkyl, aryl, aryl($C_1$-$C_4$ alkyl), and attached at a nitrogen.

In another variation, A and/or A' is an amide of a heterocycle attached at a nitrogen, where the heterocycle is substituted with heterocyclyl, heterocyclylalkyl, cycloalkyl, cycloalkylalkyl, aryl, arylalkyl.

In another embodiment, A and/or A' in formula (I) or (II) is an amide of an optionally substituted benzyl, optionally substituted 1-naphthylmethyl, or optionally substituted 2-naphthylmethyl amine. Optional substitutions include, but are not limited to, 2,3-dichloro, 2,5-dichloro, 2,5-dimethoxy, 2-trifluoromethyl, 2-fluoro-3-trifluoromethyl, 2-fluoro-5-trifluoromethyl, 2-methyl, 2-methoxy, 3,4-dichloro, 3,5-ditrifluoromethyl, 3,5-dichloro, 3,5-dimethyl, 3,5-difluoro, 3,5-dimethoxy, 3-bromo, 3-trifluoromethyl, 3-chloro-4-fluoro, 3-chloro, 3-fluoro-5-trifluoromethyl, 3-fluoro, 3-methyl, 3-nitro, 3-trifluoromethoxy, 3-methoxy, 3-phenyl, 4-trifluoromethyl, 4-chloro-3-trifluoromethyl, 4-fluoro-3-trifluoromethyl, 4-methyl, and the like.

In another embodiment, A and/or A' in formula (I) or (II) is an amide of an optionally substituted benzyl-N-methylamine. In another embodiment, A in formula (I) or (II) is an amide of an optionally substituted benzyl-N-butylamine, including n-butyl, and t-butyl. In another embodiment, A in formula (I) or (II) is an amide of an optionally substituted benzyl-N-benzylamine. Optional substitutions include, but are not limited to, 2,3-dichloro, 3,5-dichloro, 3-bromo, 3-trifluoromethyl, 3-chloro, 3-methyl, and the like.

In another embodiment, A and/or A' in formula (I) or (II) is an amide of an optionally substituted 1-phenylethyl, 2-phenylethyl, 2-phenylpropyl, or 1-phenylbenzylamine. In another embodiment, A and/or A' in formula (I) or (II) is an amide of an optionally substituted 1-phenylethyl, 2-phenylethyl, 2-phenylpropyl, 1-phenylbenzylamine-N-methylamine. In another embodiment, A and/or A' in formula (I) or (II) is an amide of an optionally substituted 2-phenyl-3-alanine, or derivative thereof, 1-phenylpropanolamine, and the like. Optional substitutions include, but are not limited to, 3-trifluoromethoxy, 3-methoxy, 3,5-dimethoxy, 2-methyl, and the like.

In another embodiment, A and/or A' in formula (I) or (II) is an amide of an optionally substituted 1-phenylcyclopropyl, 1-phenylcyclopentyl, or 1-phenylcyclohexylamine. Optional substitutions include, but are not limited to, 3-fluoro, 4-methoxy, 4-methyl, 4-chloro, 2-fluoro, and the like.

In another embodiment, A and/or A' in formula (I) or (II) is an amide of an optionally substituted heteroarylmethylamine, including but not limited to 2-furyl, 2-thienyl, 2-pyridyl, 3-pyridyl, 4-pyridyl, and the like. Optional substitutions include, but are not limited to, 5-methyl, 3-chloro, 2-methyl, and the like.

In another embodiment, A and/or A' in formula (I) or (II) is an amide of a partially saturated bicyclic aryl, including but not limited to 1-, 2-, 4-, and 5-indanylamine, 1- and 2-tetrahydronaphthylamine, indolinyl, tetrahydroquinolinyl, tetrahydroisoquinolinyl, and the like, each of which is optionally substituted.

In another embodiment, A and/or A' in formula (I) or (II) is an amide of a substituted piperidine or piperazine. Substituents on the piperidine or piperazine include heterocyclyl, heterocyclylalkyl, optionally substituted aryl, and optionally substituted arylalkyl. Illustrative piperidines and piperazines include the formulae:

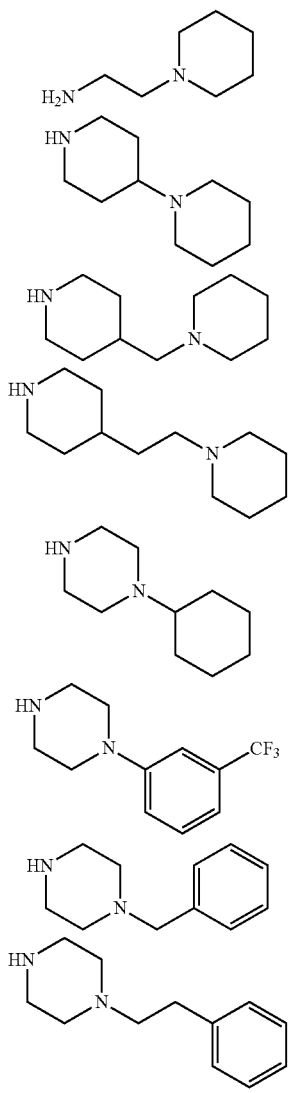

In another embodiment, A' in formula (I) is an amide of a substituted heterocycle attached at nitrogen. Substituents include alkyl, cycloalkyl, cycloalkylalkyl, heterocyclyl, heterocyclylalkyl, aryl, and arylalkyl. In one variation embodiment, A' in formula (I) is an amide of a heterocycle attached at nitrogen substituted with alkyl, cycloalkyl, cycloalkylalkyl, heterocyclyl, or heterocyclylalkyl.

In another embodiment, A' in formula (I) is an amide of an optionally substituted arylheterocyclylamine, arylalkylheterocyclylamine, heterocyclylalkylamine, or heteroarylalkylamine. In another embodiment, A' is an amide of piperidin-1-ylpiperidine or piperidin-1-ylalkylpiperidine. In another embodiment, alkyl is $C_1$-$C_2$-alkyl.

It is appreciated that in the foregoing illustrative examples of A and/or A' that include a chiral center, either of the optically pure enantiomers may be included in the compounds described herein; alternatively, the racemic form may be used. For example, either or both of the following enatiomers may be included in the compounds described herein (R)-1-(3-methoxyphenyl)ethylamine, (R)-1-(3-trifluoromethylphenyl)ethylamine, (R)-1,2,3,4-tetrahydro-1-naphtylamine, (R)-1-indanylamine, (R)-α,N-dimethylbenzylamine, (R)-α-methylbenzylamine, (S)-1-(3-methoxyphenyl)ethylamine, (S)-1-(3-trifluoromethylphenyl)ethylamine, (S)-1,2,3,4-tetrahydro-1-naphtylamine, (S)-1-indanylamine, and (S)-α-methylbenzylamine, and the like.

In another embodiment of the compounds of formula (II), Q is oxygen or sulfur. In another embodiment of the compounds of formula (II), R" is optionally substituted arylalkyl. In another embodiment of the compounds of formula (II), A is an amide of a substituted piperidine or piperazine.

In another embodiment of the compounds of formula (I), n is 1 or 2. In another embodiment of the compounds of formula (I), n is 1. In another embodiment of the compounds of formula (II), n is 1 or 2. In another embodiment of the compounds of formula (II), n is 1.

In another embodiment of the compounds of formulae (I) or (II), $R^2$ is hydrogen, alkyl, alkoxy, alkylthio, cyano, formyl, alkylcarbonyl, or a substituent selected from the group consisting of —$CO_2R^8$ and —$CONR^8R^{8'}$, where $R^8$ and $R^{8'}$ are each independently selected from hydrogen and alkyl. In another embodiment of the compounds of formulae (I) or (II), $R^2$ is hydrogen or alkyl. In another embodiment of the compounds of formulae (I) or (II), $R^2$ is hydrogen.

In another embodiment of the compounds of formulae (I) or (II), $R^1$ is hydrogen. In another embodiment of the compounds of formulae (I) or (II), $R^1$ is methyl. In another embodiment of the compounds of formulae (I) or (II), both $R^1$ and $R^2$ are hydrogen.

In another embodiment of the compounds of formulae (I) or (II), $R^3$ is of the formulae:

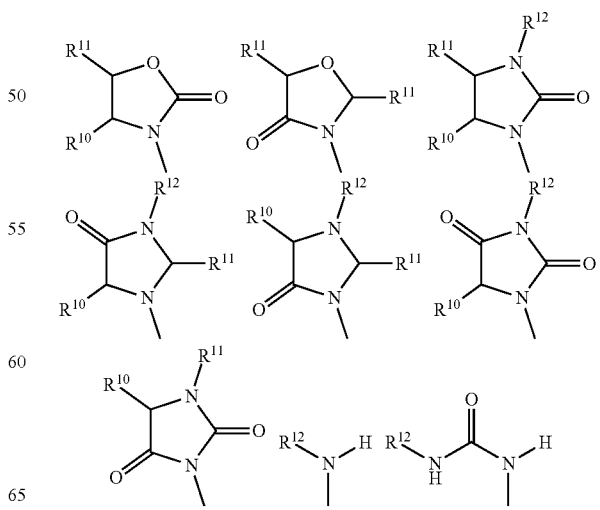

wherein $R^{10}$ and $R^{11}$ are each independently selected from hydrogen, optionally substituted alkyl, optionally substituted cycloalkyl, alkoxycarbonyl, alkylcarbonyloxy, optionally substituted aryl, optionally substituted arylalkyl, optionally substituted arylalkyloxy, optionally substituted arylalkylcarbonyloxy, diphenylmethoxy, triphenylmethoxy, and the like; and $R^{12}$ is selected from hydrogen, alkyl, cycloalkyl, alkoxycarbonyl, optionally substituted aryloxycarbonyl, optionally substituted arylalkyl, optionally substituted aryloyl, and the like.

In another embodiment of the compounds of formulae (I) or (II), $R^3$ is of the formulae:

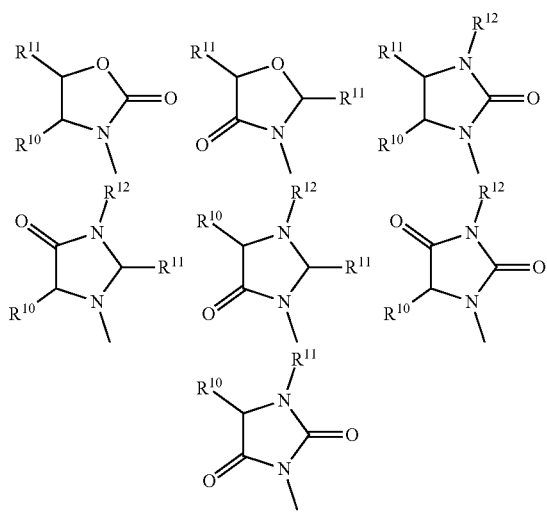

wherein $R^{10}$, $R^{11}$, and $R^{12}$ are as defined herein.

In another embodiment of the compounds of formulae (I) or (II), $R^3$ is of the formulae:

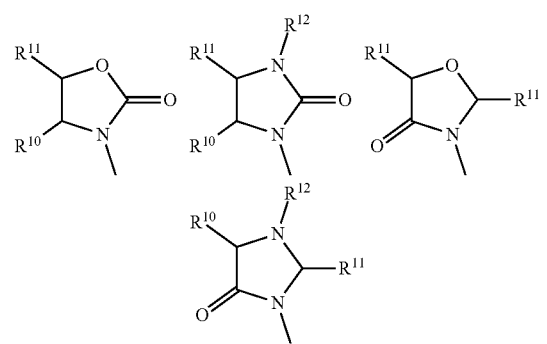

wherein $R^{10}$, $R^{11}$, and $R^{12}$ are as defined herein.

In another embodiment of the compounds of formulae (I) or (II), $R^3$ is of the formula:

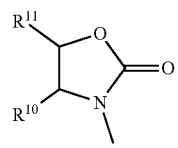

wherein $R^{10}$ and $R^{11}$ are as defined herein.

In another embodiment of the compounds of formulae (I) or (II), $R^4$ is of the formulae:

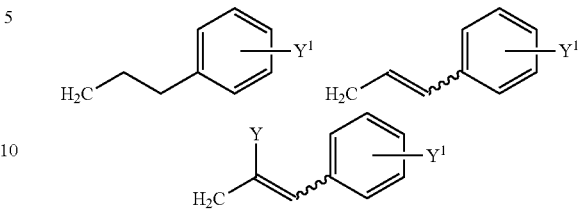

wherein Y an electron withdrawing group, such as halo, and $Y^1$ is hydrogen or one or more aryl substituents, such as but not limited to halo, hydroxy, amino, nitro, optionally substituted alkyl, optionally substituted alkoxy, and the like. It is to be understood that the double bond in the formulae may be all or substantially all (E), all or substantially all (Z), or a mixture thereof. In another embodiment, the double bond in the formulae is all or substantially all (E). In another embodiment of the compounds of formulae (I) or (II), $R^4$ is of the formulae:

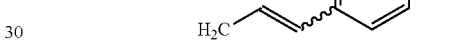

wherein $Y^1$ is as defined herein. In another embodiment, $Y^1$ is not hydrogen.

It is appreciated that the compounds of formulae (I) and (II) are chiral at the α-carbon, except when A=A', and n=0. In one embodiment of the compounds of formula (I), when n is 1, the stereochemistry of the α-carbon is (S) or (R), or is an epimeric mixture. In another embodiment of the compounds of formula (I), when n is 1, the stereochemistry of the α-carbon is (R). In another embodiment of the compounds of formula (I), when n is 2, the stereochemistry of the α-carbon is (S). In one embodiment of the compounds of formula (II), when n is 1 and Q is oxygen, the stereochemistry of the α-carbon is (R). In another embodiment of the compounds of formula (II), when n is 1 and Q is sulfur, the stereochemistry of the α-carbon is (S).

In another embodiment, compounds of formula (II) are described wherein $R^{5'}$ is optionally substituted aryl($C_2$-$C_4$ alkyl). In another embodiment, $R^{5'}$ is optionally substituted aryl($C_1$-$C_2$ alkyl). In another embodiment, $R^{5'}$ is optionally substituted benzyl. In another embodiment, $R^{5'}$ is optionally substituted alkyl.

It is to be understood that each of the foregoing embodiments of formula (I), the various genera, subgenera, and species of each of A, A', Y, $Y^1$, n, $R^1$, $R^2$, $R^3$, $R^4$, $R^5$, and the like, may be combined without limitation, and therefore each such additional embodiment of the invention is thereby described by the combination. It is also to be understood that each of the foregoing embodiments of formula (II), the various genera, subgenera, and species of each of A, Q, Y, $Y^1$, n, $R^1$, $R^2$, $R^3$, $R^4$, $R^5$, $R^{5''}$, and the like may be combined without limitation, and therefore each such additional embodiment of the invention is thereby described by the combination. For example, in another embodiment, compounds of formula (I) are described where (a) A is of the formula

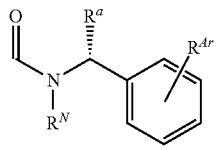

where $R^N$, $R^a$, and $R^{Ar}$ are as defined herein; and n is 1;

(b) n is 1, and $R^1$ is hydrogen;

(c) A is of the formula

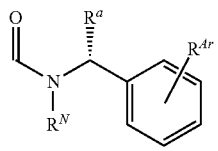

where $R^N$, $R^a$, and $R^{Ar}$ are as defined herein; n is 1; and $R^1$ is hydrogen;

(d) $R^1$ and $R^3$ are both hydrogen;

(e) $R^1$ and $R^2$ are both hydrogen; and $R^3$ is of the formula

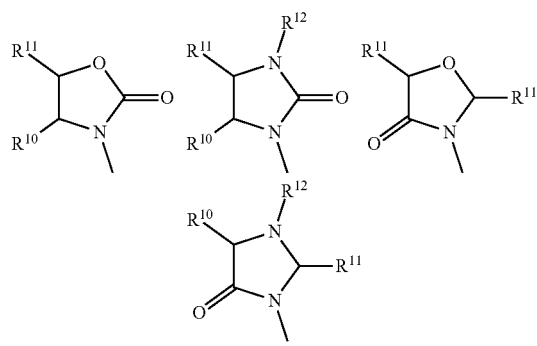

wherein $R^{10}$, $R^{11}$, and $R^{12}$ are as defined herein;

(f) A is of the formula

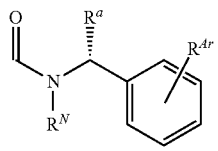

where $R^N$, $R^a$, and $R^{Ar}$ are as defined herein; n is 1; $R^1$ and $R^2$ are both hydrogen; and $R^3$ is of the formula

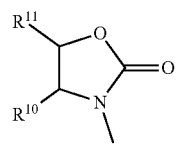

wherein $R^{10}$ and $R^{11}$ are as defined herein;

(g) A is of the formula

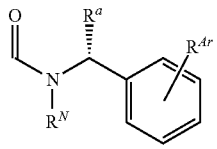

where $R^N$, $R^a$, and $R^{Ar}$ are as defined herein; n is 1; $R^1$ and $R^2$ are both hydrogen; and A' is of the formula

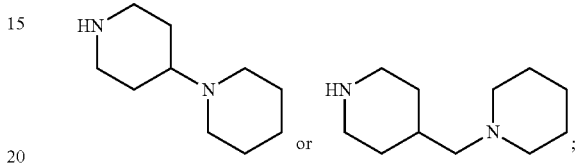

and the like.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carboxylate and derivatives thereof" includes the group $CO_2H$ and salts thereof, and esters and amides thereof, and CN.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical $-(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl) alkylcarbonylaminoalkyl, cyano, and nitro; or $Z^X$ is selected from $-CO_2R^4$ and $-CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

The term "protected amino" refers to amine protected by a protecting group that may be used to protect the nitrogen, such as the nitrogen in the β-lactam ring, during preparation or subsequent reactions. Examples of such groups are benzyl, 4-methoxybenzyl, 4-methoxyphenyl, trialkylsilyl, for example trimethylsilyl, and the like.

The term "protected carboxy" refers to the carboxy group protected or blocked by a conventional protecting group commonly used for the temporary blocking of the acidic carboxy. Examples of such groups include lower alkyl, for example tert-butyl, halo-substituted lower alkyl, for example 2-iodoethyl and 2,2,2-trichloroethyl, benzyl and substituted benzyl, for example 4-methoxybenzyl and 4-nitrobenzyl, diphenylmethyl, alkenyl, for example allyl, trialkylsilyl, for example trimethylsilyl and tert-butyldiethylsilyl and like carboxy-protecting groups.

It is to be understood that in the embodiments described herein, an illustrative variation of alkyl is $C_1$-$C_6$ alkyl, such as methyl, ethyl, propyl, prop-2-yl, and the like; an illustrative variation of alkenyl is $C_2$-$C_6$ alkenyl, such as vinyl, allyl, and the like; an illustrative variation of alkynyl is $C_2$-$C_6$ alkynyl, such as ethynyl, propynyl, and the like; an illustrative variation of alkoxy is $C_1$-$C_4$ alkoxy, such as methoxy, pent-3-oxy, and the like; an illustrative variation of alkylthio is $C_1$-$C_4$ alkylthio, such as ethylthio, 3-methylbuty-2-ylthio, and the like; an illustrative variation of alkylcarbonyl is $C_1$-$C_3$ alkylcarbonyl, such as acetyl, propanoyl, and the like; an illustrative variation of cycloalkyl is $C_3$-$C_8$ cycloalkyl; an illustrative variation of cycloalkenyl is $C_3$-$C_9$ cycloalkenyl, such as limonenyl, pinenyl, and the like; an illustrative variation of optionally substituted arylalkyl is optionally substituted aryl($C_1$-$C_4$ alkyl); an illustrative variation of optionally substituted arylalkenyl is optionally substituted aryl($C_2$-$C_4$ alkenyl); an illustrative variation of optionally substituted arylalkynyl is optionally substituted aryl($C_2$-$C_4$ alkynyl); an illustrative variation of alkoxyalkyl is ($C_1$-$C_4$ alkoxy)-($C_1$-$C_4$ alkyl); an illustrative variation of optionally substituted heteroarylalkyl is optionally substituted heteroaryl($C_1$-$C_4$ alkyl); and an illustrative variation of alkoxycarbonyl is $C_1$-$C_4$ alkoxycarbonyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO$_2$H, —NR$_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$)alkoxy, each of which is optionally further substituted with one or more of 1 to 3 halogen atoms; optionally substituted aryl($C_2$-$C_{16}$)alkanoyl and optionally substituted heteroaryl($C_2$-$C_{16}$)alkanoyl, such as the aryl or heteroaryl radical being unsubstituted or substituted by 1 to 3 substituents selected from the group consisting of halogen, ($C_1$-$C_3$)alkyl and ($C_1$-$C_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "antagonist," as used herein, refers to a full or partial antagonist. While a partial antagonist of any intrinsic activity may be useful, the partial antagonists illustratively show at least about 50% antagonist effect, or at least about 80% antagonist effect. The term also includes compounds that are full antagonists of one or more vasopressin receptors. It is appreciated that illustrative methods described herein require therapeutically effective amounts of vasopressin receptor antagonists; therefore, compounds exhibiting partial antagonism at one or more vasopressin receptors may be administered in higher doses to exhibit sufficient antagonist activity to inhibit the effects of vasopressin or a vasopressin agonist.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustrative routes of oral administration include tablets, capsules, elixirs, syrups, and the like. Illustrative routes for parenteral administration include intravenous, intraarterial, intraperitoneal, epidurial, intraurethral, intrastemal, intramuscular and subcutaneous, as well as any other art recognized route of parenteral administration.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

Without being bound by theory, it is believed herein that AVP and related peptides represent a family of chemical signals in vertebrates and serve an important function in the control of social behaviors and emotions. AVP is synthesized in neurons in the hypothalamus of all mammals. It is released from nerve endings in the median eminence and transported to the pituitary gland, where it enhances the release of adrenocorticotrophic hormone (ACTH) and ultimately the level of stress hormones in the circulation through its actions at pituitary AVP receptors. From nerve endings in the pituitary, AVP also enters the general blood stream where it acts on the heart and blood vessels to affect cardiac performance and on the kidneys to decrease urine volume. AVP neurons and nerve fibers also are found throughout the limbic system of the brain. AVP exerts its physiological and behavioral effects by binding to specific G-Protein Coupled Receptors (GPCRs) in the central nervous system and certain peripheral tissues/sites. Three distinct AVP receptor subtypes have been identified—V1a, V1b, and V2. V1a is the predominant AVP receptor found in the limbic system and cortex, V1b receptor is located in limbic system and pituitary gland, although it is less widespread than V1a. The V2 receptor is localized in kidney, where it mediates the antidiuretic effects of vasopressin. It is generally believed that V2 is not expressed in the nervous systems of adult animals or humans. These findings have led to widespread interest in V1a and V1b receptors as potential targets for CNS therapeutics.

It has been discovered herein that a common thread in PTSD and co-morbidities of PTSD is HPA axis disturbance and altered vasopressin signaling, such as by and between the the limbic system, cerebral cortex, anterior pituitary, and adrenal cortex, and/or delayed feedback signaling of certain neurotransmitters (CRH, AVP, and the like), rate sensitive feedback of certain neurotransmitters and other signaling molecules (plasma ACTH, plasma corticosterone, and the like), and dysfunctions thereof.

Without being bound by theory, it is believed herein that the poor performance of current treatment options and the dearth of new options may each be due to the complexity of PTSD and the differences in the underlying neurobiology of the disorder. For example, though without being bound by theory, PTSD is believed herein to be a constellation of disorders. Illustrative co-morbidities include, but are not limited to major depression, anxiety disorders, impulsivity and anger disorders, intermittent explosive disorder, substance abuse, and the like.

In another embodiment, compounds, compositions, medicaments, and methods are described herein for treating a patient in need of relief from PTSD (DSM-IV: 309.81). In another embodiment, compounds, compositions, medicaments, and methods are described herein for treating a patient in need of relief from PTSD with common co-morbidities, such as other anxiety disorders, including one or more of general anxiety disorder or related anxiety disorders, and the like. In another embodiment, compounds, compositions, medicaments, and methods are described herein for treating a patient in need of relief from PTSD with co-morbid intermittent explosive disorder, such as DSM-IV: 312.34, and the like. In another embodiment, compounds, compositions, medicaments, and methods are described herein for treating a patient in need of relief from PTSD co-morbid with one or more depression disorders, including major depression and treatment-resistant depression, such as DSM-IV: 296.33, and the like. In another embodiment, compounds, compositions, medicaments, and methods are described herein for treating a patient in need of relief from PTSD co-morbid with one or more impulse control/anger disorders, such as DSM-IV: 301.7, 301.83, 312.82, and the like. In another embodiment, compounds, compositions, medicaments, and methods are described herein for treating a patient in need of relief from combinations of such co-morbidities.

Intermittent explosive disorder, and PTSD & other anxiety disorders are recognized as a major medical issue by the Department of Defense and the National Institute of Mental Health. These conditions have been observed at high rates in active duty soldiers and returning veterans. In addition, the emotional, social, and medical consequences are understood to extend beyond the soldiers suffering from these disorders to their families as well. Current treatment options include repurposed antidepressants and anxiolytics, but those regimens have not shown sufficient efficacy, have the potential to produce undesirable and unwanted side effects, and reportedly offer limited relief. In particular, such currently utilized medications, which are not specific for intermittent explosive disorder, have been reported to be minimally effective and may produce unwanted side effects including sexual dysfunction, sleep disturbances, and in some cases, suicidal thoughts. Improved treatments are needed that are more efficacious and also have fewer side effects. Accordingly, there is a need for treatments for intermittent explosive disorder, and other stress-related mental health conditions. In another embodiment, methods, uses, compositions, and compounds are described herein for treating PTSD, including PTSD with co-morbid diseases and disorders, without or without substantial sexual dysfunction.

Compounds described herein that target vasopressin receptors in the brain represent a novel therapeutic approach for the treatment of Intermittent Explosive Disorder and other stress-related mental health conditions. The potential utility of vasopressin (AVP) antagonists is based on preclinical and clinical observations. Without being bound by theory, it is believed herein that elevated levels of AVP are a clinical indicator of individuals that display inappropriate aggression and anger, and may be combined with disturbances in the stress response.

In another embodiment, compounds described herein are active at the V1a AVP receptor. In another embodiment, compounds described herein are selectively active at the V1a AVP receptor, and are less active, substantially less active, and/or inactive at other AVP receptor, such as the V1b and/or V2 subtypes of AVP receptors. In another embodiment, compounds described herein are 10-fold selective for the V1a receptor compared to the V1b and/or V2 receptor. In another embodiment, compounds described herein are 100-fold selective for the V1a receptor compared to the V1b and/or V2 receptor. In another embodiment, compounds described herein are 1000-fold selective for the V1a receptor compared to the V1b and/or V2 receptor. In another embodiment, compounds described herein are 10,000-fold selective for the V1a receptor compared to the V1b and/or V2 receptor.

In another embodiment, compounds described herein cross the blood-brain-barrier (BBB) and show high CNS permeability. In another embodiment, compounds described herein show efficacious dose levels in the brain for treating PTSD. In another embodiment, compounds described herein show efficacious dose levels in the brain for treating intermittent explosive disorder. In another embodiment, compounds described herein show efficacious dose levels in the brain for treating PTSD co-morbid with intermittent explosive disorders. In another embodiment, compounds described herein exhibit plasma levels at or in excess of those necessary for clinical efficacy in treating PTSD and PTSD co-morbid with other disorders, including but not limited to one or more of intermittent explosive disorder, major depressive disorder, anxiety, and/or other stress-related mood disorders. In another embodiment, compounds described herein exhibit pharmacokinetics consistent with twice per day (b.i.d.) dosing. In another embodiment, compounds described herein exhibit pharmacokinetics consistent with once per day (q.d.) dosing. It is appreciated herein that both b.i.d. and q.d. dosing may be an important feature in improving patient compliance, leading to overall enhanced clinical effectiveness. In another embodiment, compounds described herein are metabolically stable in stomach and blood. In another embodiment, compounds described herein exhibit cardiovascular safety profiles both in vivo and in vitro consistent with the treatment of PTSD, and PTSD co-morbid with other disorders, including but not limited to one or more of intermittent explosive disorder, major depressive disorder, anxiety disorders, impulse control and anger disorders, and/or other stress-related mood disorders. In another embodiment, compounds described herein exhibit respiratory safety in vivo.

In another embodiment, compounds described herein, and pharmaceutical compositions and medicaments containing them, exhibit high plasma levels and high brain levels, including with oral administration. In another embodiment, compounds described herein, and pharmaceutical compositions and medicaments containing them, capable of crossing the blood brain barrier (BBB), including with oral administration. In another embodiment, compounds described herein, and pharmaceutical compositions and medicaments containing them, exhibit high CNS bioavailability and high affinity without significant or competitive binding to other predetermined GPCRs, or other predetermined receptors, including but not limited to neurotransmitter related receptors, steroid receptors, ion channels, second messenger receptors, prostaglandin receptors, growth factor and hormone receptors, other brain and gastrointestinal tract peptide receptors, other enzymes, and the like. In one aspect, compounds described herein, and pharmaceutical compositions and medicaments containing them, are inactive or substantially inactive at 100 nM against a standard panel of 64 receptors including 35 GPCRs (Novascreen panel), including neurotransmitter related receptors, steroidal receptors, ion channels, second messenger receptors, prostaglandin receptors, growth factor receptors, hormonal receptors, brain/gut peptides (not including vasopressin 1), and enzymes.

In another embodiment, compounds described herein, and pharmaceutical compositions and medicaments containing them, have specific behavioral effects that are context dependent (see, for example, Ferris & Potegal (1988)). For example, in another embodiment, compounds described herein, and pharmaceutical compositions and medicaments containing them, block aggression, but have little or no effect on sexual behavior. In another embodiment, compounds described herein, and pharmaceutical compositions and medicaments containing them, block the recall of fear, but have little or no effect on the recognition of fear under appropriate circumstances.

EXAMPLES

Method Examples

Example

Human vasopression $V_{1a}$ receptor binding assay. A cell line expressing the human $V_{1a}$ receptor in CHO cells (henceforth referred to as the h$V_{1a}$ cell line) was obtained from Dr. Michael Brownstein, NIMH, Bethesda, Md., USA. The h$V_{1a}$ cDNA sequence is described by Thibonnier et al., Journal of Biological Chemistry, 269, 3304-3310 (1994), and the expression method was the same as described by Morel et al. (1992). The h$V_{1a}$ cell line was grown in alpha-MEM with 10% fetal bovine serum and 250 ug/ml G418 (Gibco, Grand Island, N.Y., USA). For competitive binding assay, hV1a cells were plated into 6-well culture plate at 1:10 dilution from a confluency flask, and maintained in culture for at least two days. Culture medium was then removed, cells were washed with 2 ml binding buffer (25 mM Hepes, 0.25% BSA, 1×DMEM, PH=7.0). To each well, 990 µl binding buffer containing 1 nM 3H-AVP was added, and followed by 10 µl series diluted Example compounds dissolved in DMSO. All incubations were in triplicate, and dose-inhibition curves consisted of total binding (DMSO) and 5 concentrations (0.1, 1.0, 10, 100, and 1000 nM) of test agents encompassing the $IC_{50}$. 100 nM cold AVP (Sigma) was used to assess non-specific binding. Cells were incubated for 45 minutes at 37° C., assay mixture was removed and each well was washed three times with PBS (pH=7.4). 1 ml 2% SDS was added per well and plates were let sit for 30 minutes. The whole content in a well was transferred to a scintillation vial. Each well was rinsed with 0.5 ml PBS which was then added to the corresponding vial. Scintillation fluid (Ecoscint, National Diagnostics, Atlanta, Ga.) was then added at 3 ml per vial. Samples were counted in a liquid scintillation counter (Beckman LS3801). $IC_{50}$ values were calculated by Prism Curve fitting software.

All of the alkanedioic esters and amides exemplified in the foregoing examples dissolved in DMSO were tested in this assay. Binding curves were generated according to methods described by Thibonnier et al. (1994). [$^3$H]-AVP was added to the hV1a cell cultures followed by 10-fold dilutions of each test compound. All active compounds showed a dose-dependent competitive binding curve, with $IC_{50}$ and $K_i$ values characteristic of high affinity binding to $V_{1a}$ receptors in CHO cells expressing the human $V_{1a}$ receptor (the hV1a cell line). For example, Example 225 showed a dose-dependent competitive binding curve, with $IC_{50}$ (1.86-2.13 nM) and $K_i$ (1.14-1.30 nM) values.

Binding affinities ($IC_{50}$) and inhibition constants ($K_i$) for illustrative compounds are shown in the following Table.

| Example | $V_{1a}$ Binding Affinity $IC_{50}$ (nM) | $V_{1a}$ $K_i$ (nM) |
|---|---|---|
| 18 | 35 | — |
| 19 | 35 | — |
| 20 | 35 | — |
| 35 | 1.9 | 1.17 |
| 37 | 5.5 | 3.39 |
| 38 | <25 | 85 |
| 39 | 23 | 13.3 |
| 40 | 11 | 6.5 |
| 41 | <20 | 18.2 |
| 42 | <20 | 26.4 |
| 42A | 1.77 | 1.17 |
| 44 | 3.1 | 1.89 |
| 47 | ~50 | — |
| 59 | <100 | — |
| 63 | 1.84 | 1.13 |
| 66 | ~50 | — |
| 77 | <100 | — |
| 78 | <100 | — |
| 81 | <100 | — |
| 82 | <50 | 5.12 |
| 85 | 5.87 | 3.6 |
| 86A | 9.79 | 6 |
| 87 | 15 | — |
| 88 | 2.4 | 1.45 |
| 91 | 3.24 | 1.99 |
| 95 | 1.76 | 1.08 |
| 96 | 4.35 | 2.66 |
| 100 | <100 | — |
| 101 | ~100 | — |
| 102 | <100 | — |
| 103 | 0.81 | 0.49 |
| 104 | 1.85 | 1.13 |
| 106 | ~100 | — |
| 107 | <50 | — |
| 108 | ~100 | — |
| 109 | ~100 | — |
| 110 | 0.49 | 0.27 |
| 111 | 1.31 | 0.82 |
| 112 | 1.34 | 0.8 |
| 120 | 0.75 | 0.46 |
| 120A | 16.2 | 9.9 |
| 120B | 2.93 | 1.79 |
| 120E | 3.2 | 1.95 |
| 120H | 2.75 | 1.68 |
| 132D | 6.3 | 3.9 |
| 132F | 4.8 | 3 |
| 133 | 2.43 | 1.49 |
| 134A | 12.9 | 7.9 |
| 134B | 44.8 | 27.5 |
| 134C | 9.1 | 5.58 |
| 134G | 6 | 3.7 |
| 134J | 5.29 | 3.25 |
| 135 | ~50 | — |
| 136 | 11 | 33 |

| Example | V$_{1a}$ Binding Affinity IC$_{50}$ (nM) | V$_{1a}$ K$_i$ (nM) |
|---|---|---|
| 137 | 17 | 10.5 |
| 138 | 21 | 13 |
| 139 | 9.5 | 5.84 |
| 172 | 4.5 | 2.78 |
| 173 | <100 | — |
| 174 | 1.46 | 0.89 |
| 175 | 4.56 | 2.79 |
| 176 | 0.61 | 0.38 |
| 177 | 0.67 | 0.41 |
| 178 | <50 | — |
| 179 | 0.81 | 0.51 |
| 180 | 0.33 | 0.2 |
| 181 | <50 | — |
| 182 | 1.52 | 0.93 |
| 183 | <10 | — |
| 184 | <10 | — |
| 185 | 1.27 | 0.82 |
| 186 | <10 | — |
| 187 | 1 | 0.66 |
| 188 | 7.26 | 4.45 |
| 189 | 1.7 | 1.04 |
| 190 | 0.88 | 0.54 |
| 191 | 2.92 | 1.79 |
| 192 | <10 | — |
| 193 | 1.17 | 0.72 |
| 194 | <100 | — |
| 195 | <50 | — |
| 196 | <100 | — |
| 198 | ~100 | — |
| 199 | <10 | — |
| 200 | 5.08 | 3.11 |
| 201 | 10.5 | 6.43 |
| 203 | 2.46 | 1.5 |
| 204 | 6 | 3.7 |
| 205 | 0.34 | 0.21 |
| 206 | 1.58 | 0.97 |
| 207 | 4.48 | 2.74 |
| 208 | 16.3 | 10 |
| 209 | 16 | 9.8 |
| 210 | 29.5 | 18.1 |
| 211 | 5.37 | 3.29 |
| 212 | 0.95 | 0.58 |
| 213 | 0.78 | 0.48 |
| 214 | 1.86 | 1.14 |
| 215 | 0.61 | 0.38 |
| 216 | 1.83 | 1.12 |
| 217 | 3.17 | 1.94 |
| 218 | 7.7 | 4.7 |
| 219 | 0.63 | 0.39 |
| 220 | 5.3 | 3.26 |
| 221 | 5.1 | 3.1 |
| 221A | 2.71 | 1.66 |
| 221B | 0.59 | 0.36 |
| 221C | 3 | 1.84 |
| 221D | 2.41 | 1.48 |
| 221E | 20.2 | 12.4 |
| 221F | 1.7 | 1.04 |
| 221G | 1.5 | 0.93 |
| 221H | 4 | 2.5 |
| 221I | 12 | 7.4 |
| 221K | ~5 | — |
| 221O | 8.4 | 5.1 |
| 221P | 1.7 | 1.1 |
| 221Q | 18.1 | 11.1 |
| 221R | 5.13 | 3.14 |
| 221S | 5.03 | 3.08 |
| 221X | 11.6 | 7.2 |
| 221Y | 7.6 | 4.7 |
| 221AB | <10 | — |
| 221AC | <10 | — |
| 221AD | ~50 | — |
| 221AE | ~50 | — |
| 221AI | ~50 | — |
| 221AL | ~100 | — |
| 221AM | — | 2.7 |
| 221AP | — | 3.8 |
| 221AO | ~100 | — |
| 221AQ | ~50 | — |
| 221AS | ~20 | — |
| 221AX | 83 | 51 |
| 221AY | ~30 | — |
| 221BD | 2.7 | 1.66 |
| 221BI | 56 | 35 |
| 222 | 1.83 | 1.13 |
| 224 (AVN246) | 0.49 | 0.3 |
| 225 (AVN251) | 1.08 | 0.66 |
| 225-HCl | — | 1.36 |
| 225-MeI | 4.8 | 3 |
| 226 | 0.49 | 0.3 |
| 227 | 11 | 6.71 |
| 228 | 13.6 | 8.35 |
| 229 | 1.53 | 0.94 |
| 230 | 7.07 | 4.33 |
| 230F | ~100 | — |
| 230L | 12.7 | 7.8 |
| 231 | 6.12 | 3.75 |
| 232 | 1.37 | 0.84 |
| 232D | 2.04 | 1.25 |
| 232E | 0.28 | 0.17 |
| 233 | 0.56 | 0.34 |
| 233A | — | 11.6 |
| 234 | 2.37 | 1.45 |
| 234A | 8.6 | 5.25 |
| 235 | 37 | 23 |
| 236 | 1.68 | 1.03 |
| 236A | 9 | 5.5 |
| 238 | 0.11 | 0.07 |
| 239 | 6.6 | 4 |
| 240 | 25 | 15.5 |
| 241 | 2.0 | 1.24 |
| 242 | 2.2 | 1.36 |
| 243 | 0.5 | 0.3 |
| 244 | 3.4 | 2.1 |
| 245 | 1.1 | 0.68 |
| 246 | 2.1 | 1.3 |
| 247 | 0.6 | 0.39 |
| 248 | 5.3 | 3.3 |
| 249 | 1.7 | 1 |
| 250 | 6.5 | 4 |
| 251 | 0.5 | 0.3 |
| 252 | 1.8 | 1.1 |
| 253 | 9.5 | 5.8 |
| 254 | 10 | 6.2 |
| 255 | 1.9 | 1.2 |
| 256 | 2.8 | 1.7 |
| 266 (AVN576) | 1.8 | 1.1 |
| 559 | 0.12 | 0.073 |
| 594 | — | 19 |
| 597 | 6.2 | 3.8 |
| 599 | 1.2 | 0.73 |
| 600 | 14.4 | 8.8 |
| 601 | 1 | 0.62 |
| 606 | 0.53 | 0.32 |
| 617 | — | 0.69 |
| 623 | — | 0.85 |
| 626 | — | 0.27 |
| 670 | — | 3.1 |
| 672 | — | 1.1 |
| 677 | — | 3 |
| 682 | — | 0.9 |
| 778 | — | 0.63 |

Example

Human vasopression V1b receptor-expressing cells. Human vasopressin receptor 1b (hV1b) cDNA (see, Lolait et al., "Extrapituitary expression of the rat V1b vasopressin receptor gene" Proc. Natl. Acad. Sci. USA. 92:6783-7

(1995); de Keyzer et al., "Cloning and characterization of the human V3(V1b) pituitary vasopressin receptor" FEBS Lett. 356:215-20 (1994); Sugimoto et al., "Molecular cloning and functional expression of a cDNA encoding the human V1b vasopressin receptor" J. Biol. Chem. 269: 27088-92 (1994)) was inserted into a mammalian cell expression vector PCI-neo (Promega) at EcoR1 site. The recombinant plasmid carrying hV1b cDNA was identified from transformed E. Coli clones and used for the transfection of Chinese hamster ovary cell (CHO-Kl, ATCC). Two micrograms of hV1b receptor DNA was introduced into $10^5$ CHO cells cultured in 6-well plate, using Fugene-6 mediated transfection technique (Boehringer Mannheim). Twenty-four hrs post transfection, Cells were then cultured under selection of G-418 (0.25 mg/ml) supplemented to the culture medium. Three days later, limited dilution was carried out to obtain single cell clones in 96-well plates. After a period of 2-weeks of growth, monoclones were expanded into two sets of 12-well plates. When confluence was reached, one set of wells were assayed for their ability to bind tritium-labeled arginine-vasopressin (NEN). Nine positive clones were initially identified out of 60 clones screened, and clones that demonstrated highest AVP binding were saved as permanent cell lines for hV1b affinity screening.

Example

Human or rat vasopression V1b cell-based receptor binding assay. The V1b cell lines (cells expressing either the human or rat V1b receptor) were grown in alpha-MEM medium supplemented with 10% fetal bovine serum and 250 ug/ml G418 (Gibco, Grand Island, N.Y.) in 75 $cm^2$ flask. For competitive binding assay, hV1b cells were dissociated with enzyme-free, PBS based cell dissociation solution (Specialty Media, Phillipursburg, N.J.), following the manufacturer's protocol. Cells were plated into 12-well culture plates at a rate of one flask to 18 plates (rate should be adjusted according to the extent of confluency), and maintained in culture for 2-3 days. Culture medium was then removed, cells were washed once with 2 ml binding buffer (25 mM Hepes, 0.25% BSA, 1x DMEM, PH=7.0) at room temperature. To each well, 990 ul binding buffer containing 1 nM $^3$H-AVP was added, and followed by the addition of 10 ul series diluted testing compounds or cold AVP, all dissolved in DMSO. All incubations were in triplicate, and dose-inhibition curves consisted of total binding (DMSO only) and 5 concentrations (0.1, 1.0, 10, 100, and 1000 nm) of test agent, or cold AVP, encompassing the IC50. Cells were incubated for 30 min at 37° C. in a moisturized incubator. Assay mixture was then removed and each well was washed three times with PBS (pH=7.4). After washing, 1 ml 2% SDS was added per well and plates were let sit for 15 min at RT. Gently pat the plate to make sure that lysed cells were detached. The whole content in a well was transferred to a scintillation vial. Each well was then rinsed with 0.5 ml PBS and added to the corresponding vial. Scintillation fluid (Ecoscint, National Diagnostics, Atlanta, Ga.) was then added at 3 ml per vial. Samples were counted in a liquid scintillation counter (Beckman LS3801). IC50 and Ki values were calculated using Prism Curve fitting software. Illustrative compounds shown in the previous table show a binding constant greater than 100 nM, or greater than 1000 nM. Illustrative inhibition data (Ki, nM) are shown in the following table for selected Example compounds.

| Receptor | Example 33I (AVN246) | Example 34A (AVN251) | Example 266 (AVN576) |
| --- | --- | --- | --- |
| V1a | 0.30 | 0.66 | 1.1 |
| V1b | >1000 | >1000 | >100 |
| V2 | >1000 | >1000 | >1000 |

Example

Inhibition of phosphatidylinositol turnover ($V_{1a}$). The physiological effects of vasopressin are mediated through specific G-protein coupled receptors. The vasopressin $V_{1a}$ receptor is coupled to the $G_q/G_{11}$ family of G proteins and mediates phosphatidylinositol turnover. The agonist or antagonist character of the compounds of the invention may be determined by their ability to inhibit vasopressin-mediated turnover of phosphatidylinositol by the procedure described in the following paragraphs. Illustrative compounds, Examples 35, 44, 88, 110, and 133, were tested in this assay and found to be vasopressin $V_{1a}$ antagonists.

Example

Inhibition of vasopressin V1b-mediated phosphatidylinositol turnover, a functional assay for antagonist activity. The physiological effects of vasopressin are mediated through specific G-protein coupled receptors. The vasopressin V1b receptor is coupled to a G protein, which is coupled to cAMP. The agonist or antagonist character of the compounds described herein may be determined by their ability to inhibit vasopressin-mediated turnover of phosphatidylinositol by using conventional methods, including the procedure described in the following paragraphs.

Cell culture and labeling of cells. Three days prior to the assay, near-confluent cultures of hV1a or hV1b cells were dissociated and seeded in 6-well tissue culture plates, about 100 wells being seeded from each 75 $cm^2$ flask (equivalent to 12:1 split ratio). Each well contained 1 mL of growth medium with 2 μCi of [$^3$H]myo-inositol (American Radiolabeled Chemicals, St. Louis, Mo., USA).

Cells expressing the human or rat $V_{1b}$ receptors are grown in alpha-modified minimal essential medium containing 10% fetal bovine serum and 0.25 mg/ml G418. Three days prior to the assay, near-confluent cultures are dissociated and seeded in 6-well tissue culture plates, about 100 wells being seeded from each 75 $cm^2$ flask (equivalent to 12:1 split ratio). Each well contains 1 ml of growth medium with 2 μCi of [$^3$H] myo-inositol (American Radiolabeled Chemicals, St. Louis, Mo.).

Incubations ($V_{1a}$ and $V_{1b}$). All assays were in triplicate except for basal and 10 nM AVP (both n=6). AVP ((arginine vasopressin), Peninsula Labs, Belmont, Calif., USA (#8103)) was dissolved in 0.1N acetic acid. Test agents were dissolved in DMSO and diluted in DMSO to 200 times the final test concentration. Test agents and AVP (or corresponding volumes of DMSO) were added separately as 5 μL in DMSO to 12×75 mm glass tubes containing 1 mL of assay buffer (Tyrode's balanced salt solution containing 50 mM glucose, 10 mM LiCl, 15 mM HEPES pH 7.4, 10 μM phosphoramidon, and 100 μM bacitracin). The order of incubations was randomized. Incubations were initiated by removing the prelabeling medium, washing the monolayer once with 1 mL of 0.9% NaCl, and transferring the contents of the assay tubes to corresponding wells. The plates were incubated for 1 hour at 37° C. Incubations were terminated by removing the incubation medium and adding 500 μL of ice cold 5% (w/v) trichloroacetic acid and allowing the wells to stand for 15 min.

Measurement of [$^3$H]inositol phosphates ($V_{1a}$ and $V_{1b}$). BioRad Poly-Prep Econo-Columns were packed with 0.3 mL of AG 1 X-8 100-200 formate form resin. Resin was mixed 1:1 with water and 0.6 mL added to each column. Columns were then washed with 10 mL water. Scintillation vials (20 mL) were placed under each column. For each well, the contents were transferred to a minicolumn, after which the well was washed with 0.5 mL distilled water, which was also added to the minicolumn. The columns were then washed twice with 5 mL of 5 mM myo-inositol to elute free inositol. Aliquots (1 mL) were transferred to 20 mL scintillation vials and 10 mL of Beckman Ready Protein Plus added. After the myo-inositol wash was complete, empty scintillation vials were placed under the columns, and [$^3$H] inositol phosphates were eluted with three additions of 1 mL 0.5 M ammonium formate containing 0.1 N formic acid. Elution conditions were optimized to recover inositol mono-, bis-, and trisphosphates, without eluting the more metabolically inert tetrakis-, pentakis-, and hexakis-phosphates. To each sample was added 10 mL of a high salt capacity scintillation fluid such as Tru-Count High Salt Capacity or Packard Hionic-Fluor. Inositol lipids were measured by adding 1 mL of 2% sodium dodecyl sulfate (SDS) to each well, allowing the wells to stand for at least 30 min., and transferring the solution to 20 mL scintillation vials, to which 10 mL Beckman Ready Protein Plus scintillation fluid was then added. Samples were counted in a Beckman LS 3801 liquid scintillation counter for 10 min. Total inositol incorporation for each well was calculated as the sum of free inositol, inositol phosphates, and inositol lipids.

Data analysis ($V_{1a}$ and V1b): concentration-inhibition experiments. Concentration-response curves for AVP and concentration-inhibition curves for test agents versus 10 nM AVP were analyzed by nonlinear least-squares curve-fitting to a 4-parameter logistic function. Parameters for basal and maximal inositol phosphates, $EC_{50}$ or $IC_{50}$, and Hill coefficient were varied to achieve the best fit. The curve-fitting was weighted under the assumption that the standard deviation was proportional to dpm of radioactivity. Full concentration-response curves for AVP were run in each experiment. $IC_{50}$ values were converted to $K_i$ values, which reflect the antagonistic activities against AVP in the production of signaling molecule IP3, by application of the Cheng-Prusoff equation, based on the $EC_{50}$ for AVP in the same experiment. Inositol phosphates were expressed as dpm per $10^6$ dpm of total inositol incorporation.

Data analysis ($V_{1a}$ and $V_{1b}$): competitivity experiments. Experiments to test for $V_{1a}$ competitivity of test agents consisted of concentration-response curves for AVP in the absence and presence of two or more concentrations of test agent. Experiments to test for V1b competition by test agents consist of concentration-response curves for AVP in the absence and presence of at least five concentrations of test agent. Data were fit to a competitive logistic equation $$Y = B + \frac{M \times \{A/[E+(D/K)]\}^Q}{1 + \{A/[E+(D/K)]\}^Q}$$

where Y is dpm of inositol phosphates, B is concentration of basal inositol phosphates, M is the maximal increase in concentration of inositol phosphates, A is the concentration of agonist (AVP), E is the $EC_{50}$ for agonist, D is the concentration of antagonist (test agent), K is the $K_i$ for antagonist, and Q is the cooperativity (Hill coefficient).

Compound Example 225 produces a dose-dependent suppression of the action of AVP with $IC_{50}$ (2.68 nM) and $K_i$ (0.05 nM). These values are consistent with high affinity binding of Example 225 and its inhibition of inositol lipid synthesis via the human $V_{1a}$ receptor.

Example

The use of the compounds and compositions described herein for treating PTSD and stress-related affective illness is established using a model of predatory fear conditioning. The model uses fMRI data of rats exposed to a ferret, a natural predator, as the unconditioned stimulus while experiencing the taste of sucrose, which is highly rewarding, as the conditioned stimulus. The taste of sucrose becomes associated with the traumatic memory of the ferret. The rats exhibit a hyperarousal pattern of brain activity in the limbic cortex and hippocampus in response to the taste of sucrose alone weeks later. This hyperarousal pattern of brain activty in response to a stimulus associated with a traumatic memory is characteristic of PTSD. The data show that the brain activity associated with the memory of fear triggered by exposure to sucrose is greater than the initial exposure to the predator. Thus, the memory of fear is worse than fear itself. Treatment with compounds and compositions described herein block the hyperarousal seen with the sucrose-associated traumatic memory in untreated animals. The compounds described herein are efficacious in a this new preclinical model of PTSD in rats that utilized predatory fear as the unconditioned stimulus and the taste of sucrose as the conditioned stimulus. Pretreatment with V1a receptor antagonist AVN576 blocked the hyperarousal brain activation pattern elicited by the taste of sucrose weeks after exposure to the predator. Compounds described herein are also efficacious in established models of depression (social interaction test), anxiety (Elevated Plus Maze, Light:Dark Shuttle Box), and aggression (resident:intruder test).

The predatory fear conditioning juxtaposes an aversive unconditioned stimulus (threat of predation), with the taste of sucrose as the conditioned stimulus. During an imaging session, awake rats are exposed to a live, sable ferret placed into the bore of the magnet. This presentation of the predator is done with and without the application of sucrose to the tongue of the rat. Retrieval of the memory weeks later by the application of sucrose alone (as a Conditioned Stimulus) in the absence of the ferret elicits a robust increase in brain activity that far exceeds the initial presentation of the predator. This hyperarousal pattern of brain activity is focused on the limbic cortex, hippocampus and amygdala—neural circuits involved in emotional experience, learning, and memory, and which have been implicated in PTSD and other neuropsychiatric disorders, including those frequently co-morbid with PTSD, see, for example, (Ferris et al., Imaging the Neural Circuitry and Chemical Control of Aggressive Motivation. BMC Neurosci, 9(1):111 (2008); Shin & Liberzon, The neurocircuitry of fear, stress, and anxiety disorders. Neuropsychopharmacology. 35(1):169-91 (2010); Price and Drevets, 2009; Rodriguez et al, 2009). This model is unique for several reasons, but most importantly it associates predatory fear with a highly rewarding, hedonic stimulus, sucrose. Without being bound by theory, it is believed herein that the model parallels the emotional dilemma that may well reflect the complex associations underpinning PTSD in soldiers returning from combat areas.

Functional MRI Protocol. Experiments are conducted in a Bruker Biospec 7.0T/20-cm USR horizontal magnet (Bruker, Billerica, Mass. U.S.A) and a 20-G/cm magnetic field gradient insert (ID=12 cm) capable of a 120-µs rise time (Bruker). Radiofrequency signals are sent and received with the dual coil electronics built into the animal restrainer (Ludwig et al., 2004). At the beginning of each imaging session a high resolution anatomical data set is collected using the RARE pulse sequence (14 slice; 1.2 mm; FOV 3.0 cm; 256×256; TR 2.1 sec; TE 12.4 msec; NEX 6; 6.5 min acquisition time). Functional images are acquired using a multi-slice fast spin echo sequence. A single scanning session acquires fourteen slices every 6 sec (TR=2108 msec, TEeff=53.2 msec, RARE factor=16, NEX 1) repeated 100 times for a 10 min scan. After 5 minutes of baseline functional image collection, the ferret/sucrose or sucrose alone is introduced and 5 more minutes of functional images acquired.

Scanning Session. During an imaging session, male Long Evans rats are exposed to an adult male sable ferret confined to a vivarium or an empty vivarium placed into the bore of the magnet. A line of PE 10 tubing is passed through the opening in the front of the restraining system and positioned in the mouth of the rat. The rat's mouth is held slightly ajar by a bite bar built into the head holder. With the introduction of the ferret or empty vivarium comes the administration of 0.1 ml of a 10% sucrose solution or water through the tubing. Changes in heart rate, respiration, and temperature are non-invasively monitored throughout the 10 min scanning session. After an imaging session, rats are returned to their home cage and remain undisturbed until their next imaging session 14 days later. Animals are single housed in a 12:12 light dark cycle, and provided food and water ad libitum. 3D representations of Papez circuit (limbic cortex involved in emotional experience), along with amygdala and hippocampus of the rat were collected. Areas of the cortical circuit of Papez included the prelimbic cortex, $2^{nd}$ motor cortex, anterior cingulate cortex, primary somatosensory cortex, entorhinal cortex, anterior thalamus, mammillary bodies, retrosplenial cortex, insular cortex, and supraorbital cortex. Areas of the amygdala included the bed nucleus stria terminalis, anterior nucleus, basal nucleus, posterior nucleus, medial nucleus, cortical nucleus, lateral nucleus, and central nucleus. Areas of the hippocampus included the dentate, subiculum, CA1 and CA3. Referring to FIG. 1, areas in black denote the average significant BOLD activation of eight animals for each condition.

All animals were fully conscious during the 10 min imaging session (5 control vs 5 stimulus). (A) shows the unconditioned pattern of activation for the ferret alone. (B) shows unconditioned pattern of activation for the ferret alone following pretreatment with AVN576 (5 mg/kg body weight). (C) shows the conditioned activation pattern when the animals are re-exposed to sucrose alone in the magnet two weeks later. (D) shows the conditioned activation pattern when the animals are pretreated with AVN576 (5 mg/kg body weight), and re-exposed to sucrose alone in the magnet two weeks later. Data were also collected for unconditioned pattern of activation for the ferret alone+sucrose (not shown). All areas of the cortical circuit of Papez, amygdala, and hippocampus showed increases in activation when animals were re-exposed to sucrose alone (C) compared to ferret (A) or ferret and sucrose (not shown). All increases were significant (p<0.05), except for the entorhinal cortex, anterior cingulate cortex, cortical nucleus, and central nucleus. The data in (D) show that pretreating rats with the compounds described herein significantly reduces brain activation in the neural circuits associated with emotional experience, learning and memory when the animals are re-exposed to sucrose alone after conditioning. The data in (C) show that the predatory fear response in the unconditioned test animal is retained.

AVN576 (Example 266), was effective in blocking retrieval of predatory fear memory. Without being bound by theory, it is believed herein that vasopressin is involved in the memory of fear but not the fear response itself. Compounds described herein attenuate the hyperarousal brain activity pattern associated with the retrieval of aversive memories. A pattern of hyperarousal in fear circuits has been reported in patients having PTSD (see, for example, Shin et al., Regional cerebral blood flow in the amygdala and medial prefrontal cortex during traumatic imagery in male and female vietnam veterans with PTSD. Arch Gen Psychiatry February; 61(2):168-76 (2004); Shin and Liberzon, 2010).

Example

Resident-Intruder Model of Stress and Aggression in Rats. Neuroimaging is used to assess the blockade of stress/arousal with test compound compared to control. The effect of AVN251-HCl on functional circuitry was examined using the imaging method for awake rats. Additional details of the assay are described in Ferris et al. (2008). The study provided a representation of CNS effects of AVN251-HCl and differentiated neurobiological changes produced by AVN251-HCl compared to fluoxetine (AVN251-HCl left sexual motivation intact while fluoxetine markedly diminished activation of this circuit).

Male rats in the company of a female cage mate will piloerect in the presence of a male intruder. This piloerection is a sign of stress and aggressive intent and is associated with activation of stress/arousal circuits in the brain. AVN251-HCl treatment (5 mg/kg) blocks activation of this stress circuit. Importantly, the effect appears to be specific because mesocorticolimbic dopamine reward system function in response to a sexually motivating stimulus (an estrogen-progesterone primed female) remained intact in the presence of AVN251-HCl. Resident male rats from six male:female pairs were imaged while fully awake. During a single imaging session, these males were treated with vehicle or AVN251-HCl (5 mg/kg).

The total volume of brain activation for resident males confronted with their mate alone, mate plus intruder, and mate plus intruder in the presence of AVN251-HCl can be viewed as 3D models. While there appears to be a general decrease in BOLD signal in major regions with AVN251-HCl treatment, sexual motivation, as assessed by the presentation of a novel receptive female, was unaffected by V1a receptor blockade. Imaging shows robust activation of the different brain regions when the novel female is presented as a stimulus. Further, male residents treated with AVN251-HCl show normal sexual behavior toward receptive females (estrogen/progesterone treated ovariectomized novel females) in their home cage environment.

Stress circuit activation in response to an intruder male is assessed by obtaining brain scans viewed from a caudal/dorsal perspective as translucent shells. The localization of activated voxels is mapped as 3D volumes of activation, which are composed of 10 subjects each. Once fully registered and segmented, the statistical responses for each subject are averaged on a voxel-by-voxel basis. Those averaged voxels exceeding a 2.0% threshold are shown in their appropriate spatial location. Functional images are acquired on awake rats at 4.7 T.

Oral administration of Example 34A (AVN251) or Example 331 (AVN246) each blocked stress and aggressive motivation compared to controls. The test compounds attenuate the stress/arousal circuit activity normally occurring in response to an intruder stimulus.

Sexual motivation also activates reward circuitry in the presence of AVN251. AVN251-HCl selectively blocks aggressive motivation (Mate/Intruder) but not sexual motivation (novel female) as is seen in 3D models of activity in the primary olfactory system and reward (mesocorticolimbic dopaminergic system) pathways. The 3D volumes of activation are composed from results obtained with 10 subjects in each condition. Substantial decreases on a voxel-by-voxel basis were observed in both systems in the mate/intruder scenario in the treatment group. However, in the novel female scenario, both systems showed retained activity. Particular olfactory systems measured included the anterior olfactory nucleus, olfactory tubercle, piriform cortex, n. laterial olfactory tract, and entrorhinal cortex. Particular dopaminergic systems measured included the prelimbic cortex, accumbens, ventral pallidum, medial dorsal thalamus, and ventral tegmentum.

Example

Neuroimaging shows Blockade of Stress in Important Brain Regions. Awake rats were imaged when presented with their mate+an intruder, a highly stressful stimulus. Pretreatment with AVN251 (5 mg/kg) 90 minutes before the test session blocked the stress/arousal response. Sexual motivation and behavior remained intact. Separate areas of the brain were evaluated, including amygdala, cortex, hippocampus, and thalamus, each showing similar results.

Example

Resident-Intruder Model in Hamster. Placing an unfamiliar male hamster into the home cage of another male hamster elicits a well-defined sequence of agonistic behaviors from the resident that includes offensive aggression.

Male Syrian golden hamsters (*Mesocricetus auratus*) (140-150 g) obtained from Harlan Sprague-Dawley Laboratories (Indianapolis, Ind.) are housed individually in Plexiglas cages (24 cm×24 cm×20 cm), maintained on a reverse light:dark cycle (14L:10D; lights on at 19:00 hr) and provided food and water ad libitum. Animals are acclimated to the reverse light:dark cycle for at least two weeks before testing. All behavioral tests are conducted during the dark phase of the circadian cycle.

Behavioral Measures and Analysis. Hamsters are nocturnal and as such behavioral tests are performed during the first four hours of the dark phase under dim red illumination. The resident is scored for stress, e.g., latency to bite the intruder, total contact time with the intruder, the total number of bites, and flank marking, over a 10 minute test period (Ferris, C. F., Potegal, M. Physiology and Behavior, 44, 235-239 (1988)). Flank marking is a form of olfactory communication in which a hamster arches its back and rubs pheromone producing flank glands against objects in the environment (Johnston, R. E. Communication, In: THE HAMSTER REPRODUCTION AND BEHAVIOR. Ed Siegel, H. I. Plenum Press, New York, pp 121-154 (1985)). Flank marking frequency is greatly enhanced during aggressive encounters and is particularly robust in dominant animals initiating and winning fights (Ferris, C. F., et al., Physiology and Behavior, 40, 661-664 (1987)).

The compounds described herein are tested using five groups of five animals each over a range of doses (100 ng/kg, 10 μg/kg, 1 mg/kg, 10 mg/kg, and saline vehicle as control). Ninety min after oral gavage an intruder is placed into the home cage and the resident scored for offensive aggression. Following aggression testing, animals are screened for motor activity in an open field paradigm and sexual motivation.

Parametric data, i.e., latencies and contact time, are analyzed with a one-way ANOVA followed by Newman-Keuls post hoc tests. Non-parametric data, i.e., number of bites and flank marks, are analyzed with Kruskal-Wallis tests followed by Mann-Whitney U tests to determine differences between groups.

The latency to bite is increased and the number of bites decreased by the administration of compounds described herein, indicating a lower stress level in treated animals. Contact time may also be increased.

Example

Mouse Chronic Subordination Model of Depression. Social stress is a factor in the etiology of several psychopathologies, with individuals differing in vulnerability. Adult male mice are subjected to a model of chronic psychosocial stress in which resident/intruder dyads live chronically in sensory contact and physically interact on a daily basis. The intruder animals chronically subordinated by this procedure exhibit behaviors characteristic of depression and depression-related disorders.

Example

Anti-depressant Effect in the Social Interaction Test. Chronic social subjugation is a standard method for producing animals that exhibit depression-like physiological and behavioral profiles. A rapid subjugation paradigm in mice lead to diminished social interaction behavior, where the dependent measures are distance traveled and time in the Interaction Zone. A 28-day treatment regimen with fluoxetine, a standard antidepressant, reversed deficits produced by chronic subordination while the same regimen with chlordiazepoxide (CDP), a standard anxiolytic, had no effect. These observations are consistent with the subordination/social interaction model as a rapid behavioral screen for potential antidepressants. Additional details are described in Berton et al. (2006).

Briefly, C57B1/6J males were defeated daily for 10 days by resident, highly aggressive CF-1 males. After 5 minutes of direct exposure, a perforated plastic partition was inserted into the cage that allowed olfactory and visual contact without physical defeat for the remaining 23 hr 55 min each day. The C57 males were exposed to a different resident male in a different cage each day to increase the stress of the procedure (it was observed that all CF-1 males attacked the intruder each day). At the end of the 10 day defeat procedure, the C57 males were tested in an open field apparatus during the dark phase. A dominant male was caged in an area of the open field apparatus termed the "social interaction zone." Time and distance traveled in the zone were recorded. The C57 males were then divided randomly among the following treatments: AVN246-HCl (2 mg/kg), saline vehicle (0.45%), or chlordiazepoxide (10 mg/kg). Treatments were given daily (i.p.) for 28 days and the animals were retested. Behavioral changes were determined by calculating difference scores (Post-Pretest) and these scores were analyzed.

As shown in the Table, AVN246-HCl treatment significantly increased both distance traveled and time in the interaction zone, indicating that the compounds described herein reverse deficits in social interaction behaviors after social subjugation.

| Example | Time | Distance |
|---|---|---|
| AVN246-HCl | 35 ± 10 | 22 ± 6 |
| CDP | 0.0 ± 5 | 1.0 ± 5 |
| Saline | 10 ± 10 | −15 ± 8 |

A statistically significant difference (p<0.05) was observed between the test compound and both the untreated control (saline) and negative control (CDP). Fluoxetine, an antidepressant produced comparable improvements; chlordiazepoxide (CDP), a standard anxiolytic, had no effect. The results confirm that deficits in the social interaction induced by chronic subordination are responsive to antidepressants but not anxiolytics. AVN246 is observed to give similar results.

Example

Figure 2A:
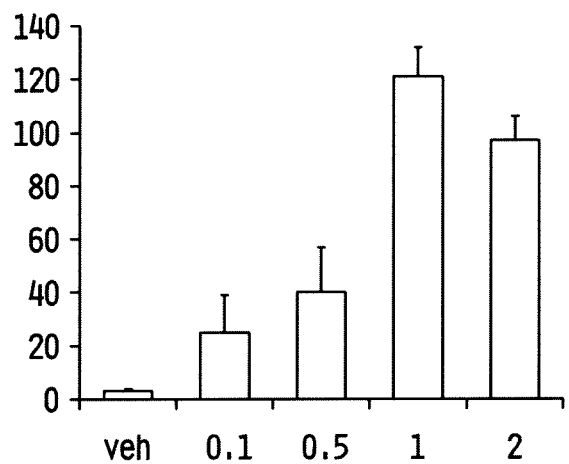
FIG. 2A shows average time spent in the light.
Figure 2B:
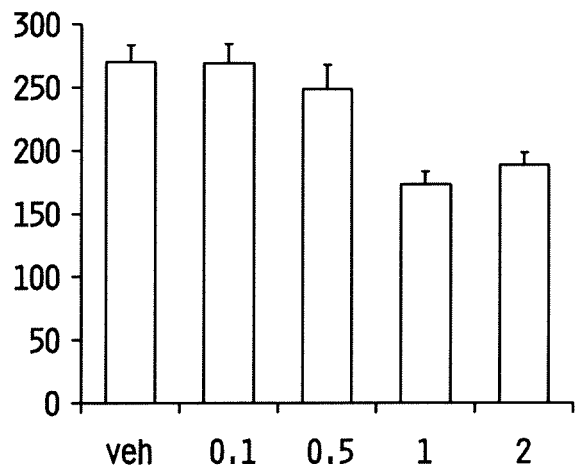
FIG. 2B shows the average time spent in the dark.
Figure 2C:
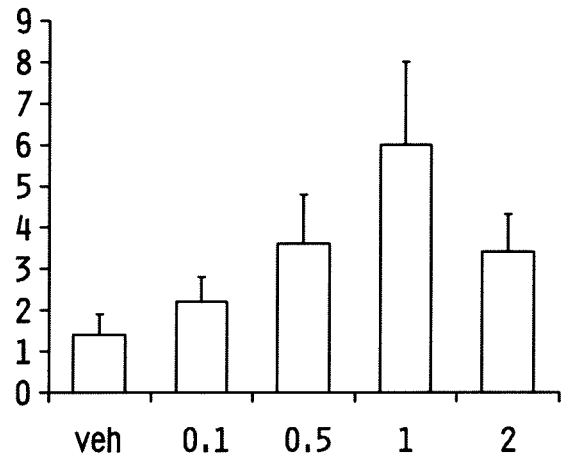
FIG. 2C shows the number of light-dark entries; for animals dosed with vehicle, 0.1, 0.5, 1, or 2 mg/kg of AVN 251.

Anxiolytic Effect in the Light:Dark Shuttle Box. The light:dark shuttle box is a standard and well characterized assay for anxiolytic effects of a test compound. Rats naturally avoid the light side of the box because it is stressful. Increased time on the light side by the treatment group compared to control reflects an anxiolytic effect (Bourin and Hascoet, 2003). Adult male Long Evans rats were administered AVN251 (0.1-2 mg/kg) by oral gavage 90 min prior to testing in a light:dark shuttle box. A dose dependent decrease in anxiety was observed in response to AVN251 vs. vehicle. In a dose dependent manner, test animals spent significantly more time in the light (FIG. 2A), less time in the dark (FIG. 2B), and made more light-dark entries (FIG. 2C) following treatment with 1 or 2 mg/kg AVN251.

Example

General Synthetic Routes. Proximal amide approach which permits synthetic variation at the distal amide site; proximal amide is set first, followed by distal amide diversity by parallel synthesis.

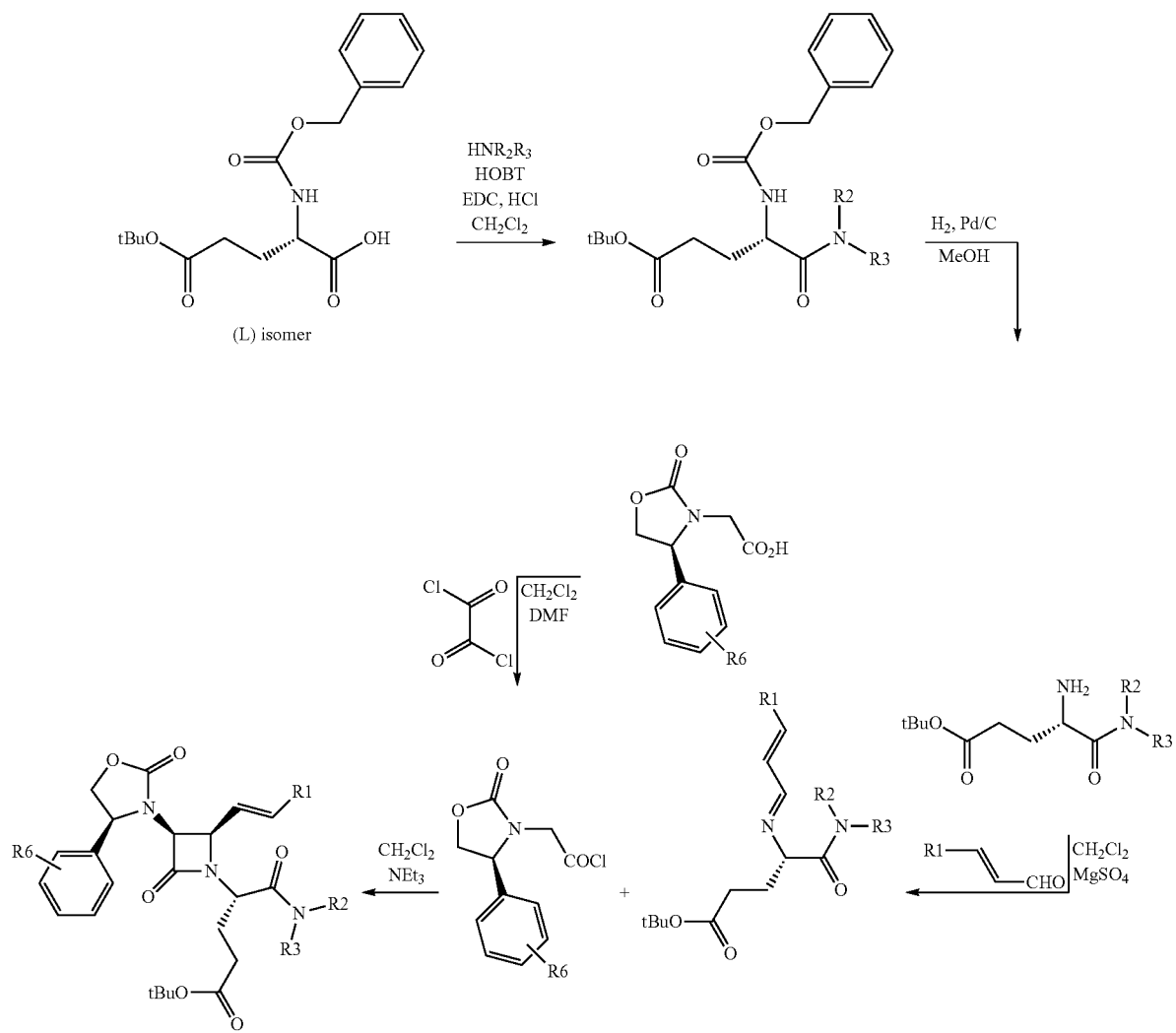

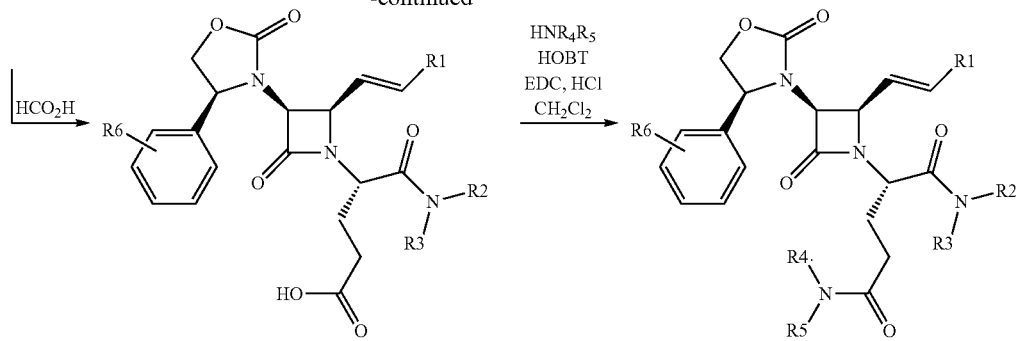
Diversity Platform
Distal amide approach which permits synthetic variations at the proximal site; distal amide is set first, followed by proximal amide diversity by parallel synthesis.
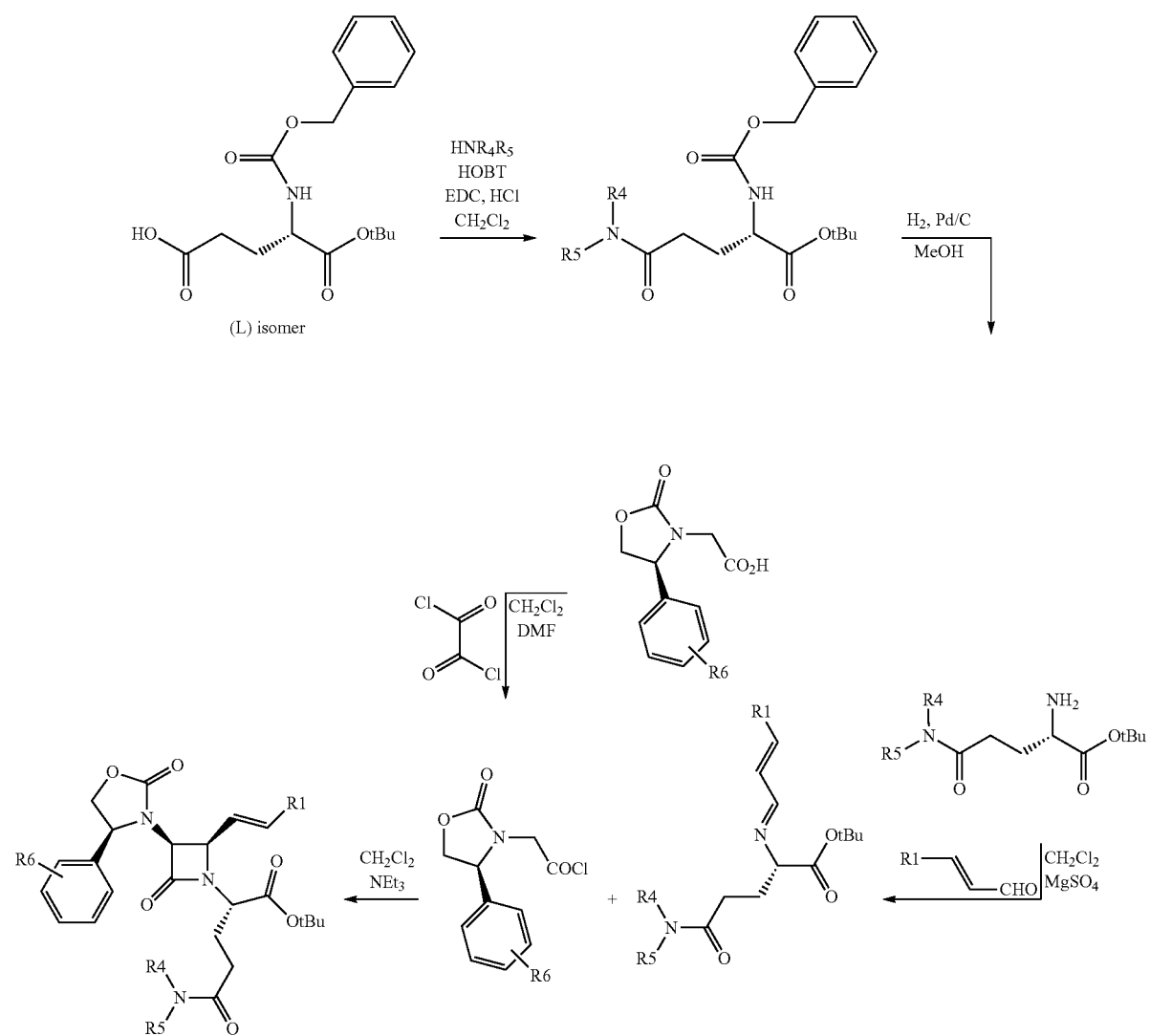

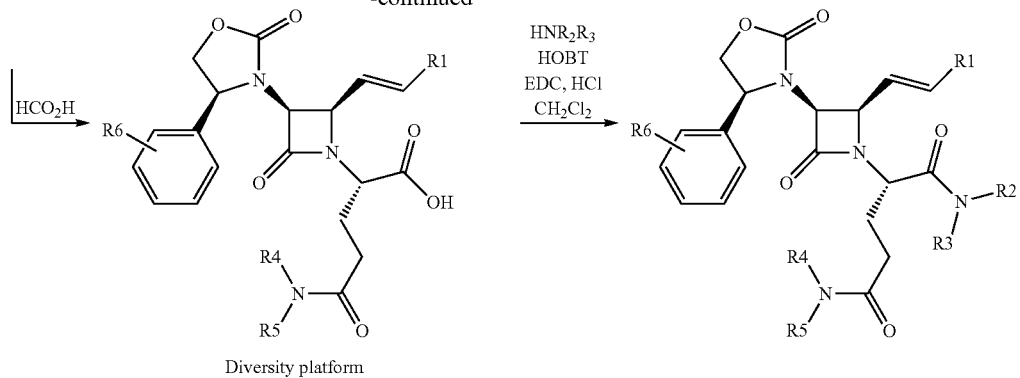
Diversity platform
Synthesis of AVN251 is shown below. All other compounds are prepared in an analogous manner with the appropriate selection of starting materials.
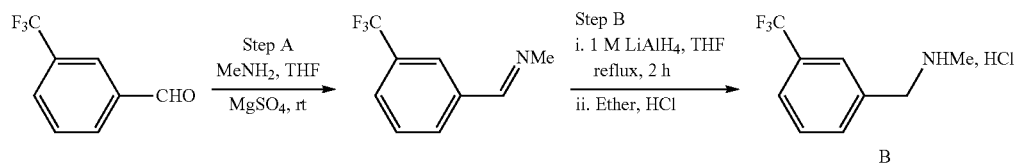
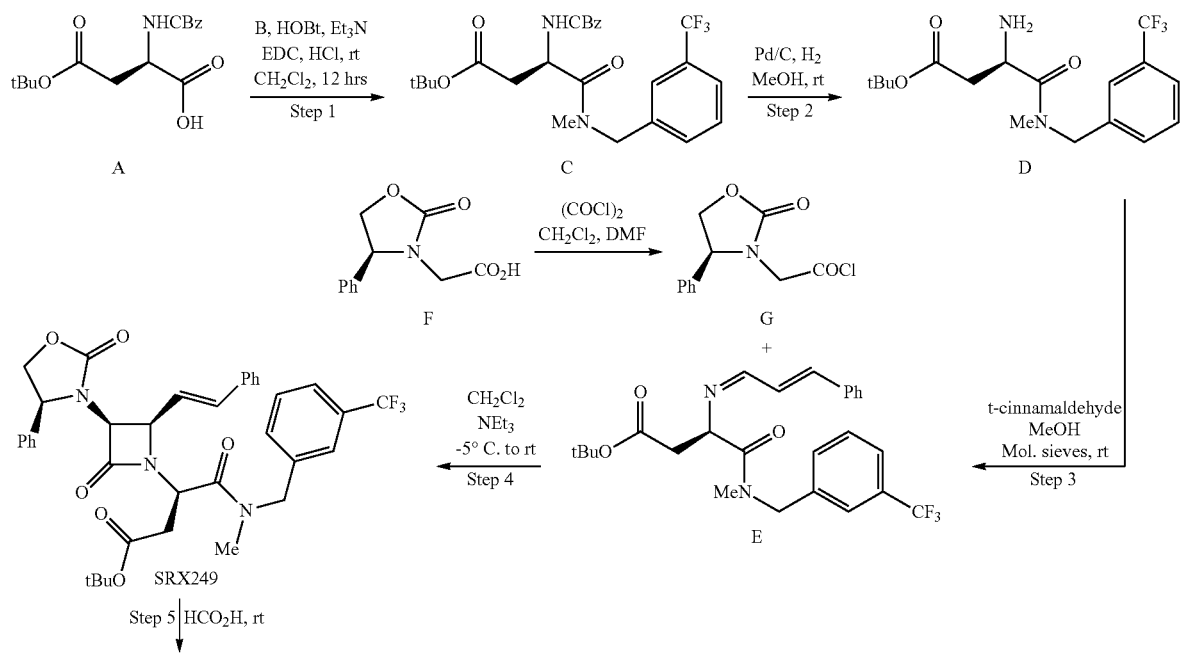

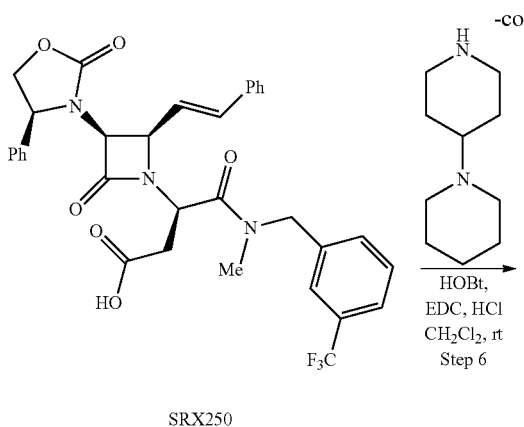

SRX250

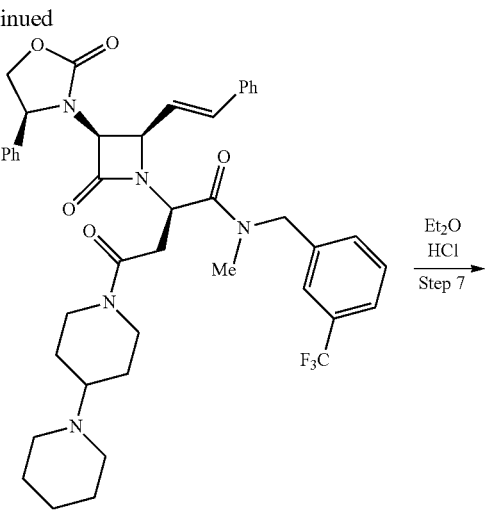

SRX251

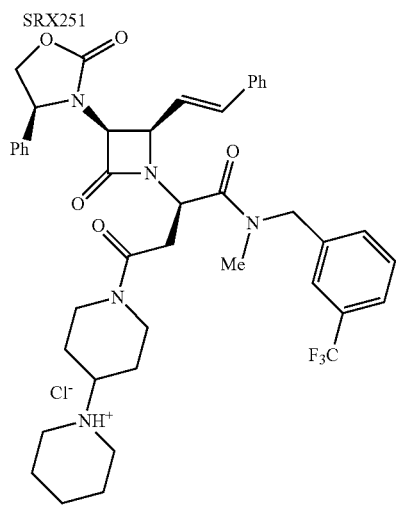

SRX251·HCl

Additional details and alternative syntheses for preparing compounds described herein are described in U.S. Pat. No. 7,119,083, the disclosure of which are incorporated herein by reference in their entirety. The compounds described herein may be formulated and administered according to the processes described in U.S. Pat. No. 7,119,083. Additoinal details are described in Guillon, C. D., et al., Azetidinones as vasopressin V1a antagonists. Bioorg Med Chem, 15(5): 2054-80 (2007).

COMPOUND EXAMPLES

Example 1

(4(S)-phenyloxazolidin-2-on-3-yl)acetyl chloride. A solution of 1.0 equivalent of (4(S)-phenyloxazolidin-2-on-3-yl) acetic acid (Evans, U.S. Pat. No. 4,665,171) and 1.3 equivalent of oxalyl chloride in 200 mL dichloromethane was treated with a catalytic amount of anhydrous dimethylformamide (85 μL/milliequivalent of acetic acid derivative) resulting in vigorous gas evolution. After 45 minutes all gas evolution had ceased and the reaction mixture was concentrated under reduced pressure to provide the title compound as an off-white solid after drying for 2 h under vacuum.

Example 1A (4(R)-phenyloxazolidin-2-on-3-yl)acetyl chloride. Example 1A was prepared following the procedure of Example 1, except that (4(R)-phenyloxazolidin-2-on-3-yl) acetic acid was used instead of (4(S)-phenyloxazolidin-2-on-3-yl)acetic acid (see, Evans & Sjogren, Tetrahedron Lett. 26:3783 (1985)).

Example 1B

Methyl (4(S)-phenyloxazolidin-2-on-3-yl)acetate. A solution of (4(S)-phenyloxazolidin-2-on-3-yl)acetic acid (1 g, 4.52 mmol) (prepared according to Evans in U.S. Pat. No. 4,665,171) in 20 mL of anhydrous methanol was treated hourly with 5 equivalents of acetyl chloride, for a total of 20 equivalents. The resulting solution was stirred overnight. The residue obtained after evaporation of the MeOH was redissolved in 30 mL of $CH_2Cl_2$ and treated with 50 mL of saturated aqueous $Na_2CO_3$. The organic layer was evaporated and dried ($MgSO_4$) to yield the title compound as a colorless oil (1.001 g, 94%); $^1H$ NMR ($CDCl_3$) δ 3.37 (d, J=18.0 Hz, 1H), 3.69 (s, 3H), 4.13 (t, J=8.3 Hz, 1H), 4.28 (d, J=18.0 Hz, 1H), 4.69 (t, J=8.8 Hz, 1H), 5.04 (t, J=8.4 Hz, 1H), 7.26-7.29 (m, 2H), 7.36-7.42 (m, 3H).

Example 1C

Methyl 2-(4(S)-phenyloxazolidin-2-on-3-yl)propanoate. A solution of methyl (4(S)-phenyloxazolidin-2-on-3-yl)acetate (1 g, 4.25 mmol) in 10 mL of anhydrous THF at −78° C. was treated with 4.68 mL (4.68 mmol) of a 1 M solution of lithium bis(trimethylsilyl)amide in THF. The reaction mixture was stirred for 1 h. at about −70° C. before adding MeI (1.59 mL, 25.51 mmol). Upon complete conversion of the azetidinone, the reaction was quenched with saturated aqueous $NH_4C_1$ and partitioned between EtOAc and water. The organic layer was washed sequentially with saturated aqueous sodium bisulfite, and saturated aqueous NaCl. The resulting organic layer was dried ($MgSO_4$) and evaporated to afford the title compound (a mixture of diasteromers) as a white solid (1.06 g, 93%); $^1$H NMR ($CDCl_3$) δ 1.07/1.53 (d/d, J=7.5 Hz, 3H), 3.59/3.74 (s/s, 3H), 3.85/4.48 (q/q, J=7.5 Hz, 1H), 4.10-4.14 (m, 1H), 4.60-4.64/4.65-4.69 (m/m, 1H), 4.88-4.92/4.98-5.02 (m/m, 1H), 7.24-7.40 (m, 5H).

Example 1D 2-(4(S)-Phenyloxazolidin-2-on-3-yl)propanoic acid. To a solution of methyl 2-(4(S)-phenyloxazolidin-2-on-3-yl)propanoate (1 g, 4.01 mmol) in 35 mL of MeOH was added, at 0° C., 14.3 mL (12.04 mmol) of a 0.84 M solution of LiOH in water. The reaction mixture was then stirred for 3 h. at ambient temperature. Upon complete hydrolysis of the azetidinone, the MeOH was removed by evaporation, the crude residue dissolved in $CH_2Cl_2$ and treated with saturated aqueous NaCl. The resulting organic layer was dried ($MgSO_4$) and evaporated to afford the title compound (racemic mixture) as a white solid (0.906 g, 96%); $^1$H NMR ($CDCl_3$) δ 1.13/1.57 (d/d, J=7.5 Hz, 3H), 3.75/4.50 (q/q, J=7.5 Hz, 1H), 4.10-4.16 (m, 1H), 4.62-4.72 (m, 1H), 4.92-5.03 (m, 1H), 7.32-7.43 (m, 5H).

Example 1E 2-(4(S)-Phenyloxazolidin-2-on-3-yl)propanoyl chloride. A solution of 1 equivalent of Example 1D and 1.3 equivalent of oxalyl chloride in 200 mL $CH_2Cl_2$ (150 mL/g of propanoic acid derivative) was treated with a catalytic amount of anhydrous DMF (85 μL/mmole of propanoic acid derivative) resulting in vigorous gas evolution. After 45 min., all gas evolution had ceased and the reaction mixture was concentrated under reduced pressure to provide the title compound as an off-white solid after drying for 2 h. under vacuum.

Example 2

General procedure for amide formation from an activated ester derivative. N-Benzyloxycarbonyl-L-aspartic acid β-t-butyl ester α-(3-trifluoromethyl)benzylamide. A solution of N-benzyloxycarbonyl-L-aspartic acid β-t-butyl ester α-N-hydroxysuccinimide ester (1.95 g, 4.64 mmol, Advanced ChemTech) in 20 mL of dry tetrahydrofuran was treated with 0.68 mL (4.74 mmol) of 3-(trifluoromethyl)benzyl amine. Upon completion (TLC, 60:40 hexanes/ethyl acetate), the mixture was evaporated, and the resulting oil was partitioned between dichloromethane and a saturated aqueous solution of sodium bicarbonate. The organic layer was evaporated to give 2.23 g (quantitative yield) of the title compound as a white solid; $^1$H NMR ($CDCl_3$) δ 1.39 (s, 9H), 2.61 (dd, J=6.5 Hz, J=17.2 Hz, 1H), 2.98 (dd, J=3.7 Hz, J=17.0 Hz, 1H), 4.41 (dd, J=5.9 Hz, J=15.3 Hz, 1H), 4.50-4.57 (m, 2H), 5.15 (s, 2H), 5.96-5.99 (m, 1H), 6.95 (s, 1H), 7.29-7.34 (m, 5H), 7.39-7.43 (m, 2H), 7.48-7.52 (m, 2H).

Examples 2A-2C and 3-5 were prepared according to the procedure of Example 2, except that N-benzyloxycarbonyl-L-aspartic acid β-t-butyl ester α-N-hydroxysuccinimide ester was replaced by the appropriate amino acid derivative, and 3-(trifluoromethyl)benzyl amine was replaced with the appropriate amine.

Example 2A

N-Benzyloxycarbonyl-L-aspartic acid β-t-butyl ester α-[4-(2-phenylethyl)]piperazinamide. N-benzyloxycarbonyl-L-aspartic acid β-t-butyl ester α-N-hydroxysuccinimide ester (5.0 g, 12 mmol, Advanced ChemTech) and 4-(phenylethyl)piperazine 2.27 mL (11.9 mmol) gave 5.89 g (quantitative yield) of the title compound as an off-white oil; $^1$H NMR ($CDCl_3$) δ 1.40 (s, 9H), 2.45-2.80 (m, 10H), 3.50-3.80 (m, 4H), 4.87-4.91 (m, 1H), 5.08 (s, 2H), 5.62-5.66 (m, 1H), 7.17-7.33 (m, 10H).

Example 2B

N-Benzyloxycarbonyl-L-glutamic acid γ-t-butyl ester α-(3-trifluoromethyl)benzylamide. N-benzyloxycarbonyl-L-glutamic acid β-t-butyl ester α-N-hydroxysuccinimide ester (4.83 g, 11.1 mmol, Advanced ChemTech) and 3-(trifluoromethyl)benzylamine) 1.63 mL (11.4 mmol) gave 5.41 g (98%) of the title compound as an off-white solid; $^1$H NMR ($CDCl_3$) δ 1.40 (s, 9H), 1.88-1.99 (m, 1H), 2.03-2.13 (m, 1H), 2.23-2.33 (m, 1H), 2.38-2.47 (m, 1H), 4.19-4.25 (s, 1H), 4.46-4.48 (m, 2H), 5.05-5.08 (m, 2H), 5.67-5.72 (m, 1H), 7.27-7.34 (m, 5H), 7.39-7.43 (m, 2H), 7.48-7.52 (m, 2H).

Example 2C

N-Benzyloxycarbonyl-L-glutamic acid γ-t-butyl ester α-[4-(2-phenylethyl)]piperazinamide. N-benzyloxycarbonyl-L-glutamic acid γ-t-butyl ester α-N-hydroxysuccinimide ester (5.0 g, 12 mmol, Advanced ChemTech) and 4-(phenylethyl)piperazine 2.19 mL (11.5 mmol) gave 5.87 g (quantitative yield) of the title compound as an off-white oil; $^1$H NMR ($CDCl_3$) δ 1.43 (s, 9H); 1.64-1.73 (m, 1H); 1.93-2.01 (m, 1H); 2.23-2.40 (m, 2H); 2.42-2.68 (m, 6H); 2.75-2.85 (m, 2H); 3.61-3.74 (m, 4H); 4.66-4.73 (m, 1H); 5.03-5.12 (m, 2H); 5.69-5.72 (m, 1H); 7.16-7.34 (m, 10H).

Example 3

N-Benzyloxycarbonyl-L-aspartic acid β-t-butyl ester α-[4-(2-phenylethyl)]piperazinamide. N-benzyloxycarbonyl-L-aspartic acid β-t-butyl ester α-N-hydroxysuccinimide ester (5.0 g, 12 mmol, Advanced ChemTech) and 4-(phenylethyl)piperazine 2.27 mL (11.9 mmol) gave 5.89 g (quantitative yield) of the title compound as an off-white oil; $^1$H NMR ($CDCl_3$) δ 1.40 (s, 9H), 2.45-2.80 (m, 10H), 3.50-3.80 (m, 4H), 4.87-4.91 (m, 1H), 5.08 (s, 2H), 5.62-5.66 (m, 1H), 7.17-7.33 (m, 10H).

Example 4

N-Benzyloxycarbonyl-L-glutamic acid γ-t-butyl ester α-(3-trifluoromethyl)benzylamide. N-benzyloxycarbonyl-L-glutamic acid β-t-butyl ester α-N-hydroxysuccinimide ester (4.83 g, 11.1 mmol, Advanced ChemTech) and 3-(trifluoromethyl)benzylamine) 1.63 mL (11.4 mmol) gave 5.41 g (98%) of the title compound as an off-white solid; $^1$H NMR (CDCl$_3$) δ 1.40 (s, 9H), 1.88-1.99 (m, 1H), 2.03-2.13 (m, 1H), 2.23-2.33 (m, 1H), 2.38-2.47 (m, 1H), 4.19-4.25 (s, 1H), 4.46-4.48 (m, 2H), 5.05-5.08 (m, 2H), 5.67-5.72 (m, 1H), 7.27-7.34 (m, 5H), 7.39-7.43 (m, 2H), 7.48-7.52 (m, 2H).

Example 5

N-Benzyloxycarbonyl-L-glutamic acid γ-t-butyl ester α-[4-(2-phenylethyl)]piperazinamide. N-benzyloxycarbonyl-L-glutamic acid γ-t-butyl ester α-N-hydroxysuccinimide ester (5.0 g, 12 mmol, Advanced ChemTech) and 4-(phenylethyl)piperazine 2.19 mL (11.5 mmol) gave 5.87 g (quantitative yield) of the title compound as an off-white oil; $^1$H NMR (CDCl$_3$) δ 1.43 (s, 9H); 1.64-1.73 (m, 1H); 1.93-2.01 (m, 1H); 2.23-2.40 (m, 2H); 2.42-2.68 (m, 6H); 2.75-2.85 (m, 2H); 3.61-3.74 (m, 4H); 4.66-4.73 (m, 1H); 5.03-5.12 (m, 2H); 5.69-5.72 (m, 1H); 7.16-7.34 (m, 10H).

Example 5A

N-[(9H-Fluoren-9-yl)methoxycarbonyl]-O-(benzyl)-D-serine t-Butyl ester. N-[(9H-Fluoren-9-yl)methoxycarbonyl]-O-(benzyl)-D-serine (0.710 g, 1.70 mmole) in dichloromethane (8 mL) was treated with t-butyl acetate (3 mL) and concentrated sulfuric acid (40 µL) in a sealed flask at 0° C. Upon completion (TLC), the reaction was quenched with of dichloromethane (10 mL) and saturated aqueous potassium bicarbonate (15 mL). The organic layer was washed with distilled water, and evaporated. The resulting residue was purified by flash column chromatography (98:2 dichloromethane/methanol) to yield the title compound as a colorless oil (0.292 g, 77%); $^1$H NMR (CDCl$_3$) δ 1.44 (s, 9H); 3.68 (dd, J=2.9 Hz, J=9.3 Hz, 1H); 3.87 (dd, J=2.9 Hz, J=9.3 Hz, 1H); 4.22 (t, J=7.1 Hz, 1H); 4.30-4.60 (m, 5H); 5.64-5.67 (m, 1H); 7.25-7.39 (m, 9H); 7.58-7.61 (m, 2H); 7.73-7.76 (m, 2H).

Example 5B

O-(Benzyl)-D-serine t-Butyl ester. Example 5A (0.620 g, 1.31 mmol) in dichloromethane (5 mL) was treated with tris(2-aminoethyl)amine (2.75 mL) for 5 h. The resulting mixture was washed twice with a phosphate buffer (pH=5.5), once with saturated aqueous potassium bicarbonate, and evaporated to give 0.329 g (quantitative yield) of the title compound as an off-white solid; $^1$H NMR (CD$_3$OD) δ 1.44 (s, 9H); 3.48 (dd, J=J'=4.2 Hz, 1H); 3.61 (dd, J=4.0 Hz, J=9.2 Hz, 1H); 3.72 (dd, J=4.6 Hz, J=9.2 Hz, 1H); 4.47 (d, J=12.0 Hz, 1H); 4.55 (d, J=12.0 Hz, 1H); 7.26-7.33 (m, 5H).

Example 6

General procedure for amide formation from a carboxylic acid. N-Benzyloxycarbonyl-D-aspartic acid β-t-butyl ester o-(3-trifluoromethyl)benzylamide. A solution of 1 g (2.93 mmol) of N-benzyloxycarbonyl-D-aspartic acid β-t-butyl ester monohydrate (Novabiochem) in 3-4 mL of dichloromethane was treated by sequential addition of 0.46 mL (3.21 mmol) of 3-(trifluoromethyl)benzylamine, 0.44 g (3.23 mmol) of 1-hydroxy-7-benzotriazole, and 0.62 g (3.23 mmol) of 1-[3-(dimethylamino)propyl]-3-ethylcarbodiimide hydrochloride. After at least 12 hours at ambient temperature or until complete as determined by thin layer chromatography (95:5 dichloromethane/methanol eluent), the reaction mixture was washed sequentially with a saturated aqueous sodium bicarbonate solution and with distilled water. The organic layer was evaporated to give 1.41 g (quantitative yield) of the title compound as an off-white solid; $^1$H NMR (CDCl$_3$) δ 1.39 (s, 9H); 2.61 (dd, J=6.5 Hz, J=17.2 Hz, 1H); 2.98 (dd, J=4.2 Hz, J=17.2 Hz, 1H); 4.41 (dd, J=5.9 Hz, J=15.3 Hz, 1H); 4.50-4.57 (m, 2H); 5.10 (s, 2H); 5.96-6.01 (m, 1H); 6.91-7.00 (m, 1H); 7.30-7.36 (m, 5H); 7.39-7.43 (m, 2H); 7.48-7.52 (m, 2H).

Examples 7-7H were prepared according to the procedure of Example 6, except that N-benzyloxycarbonyl-D-aspartic acid β-t-butyl ester monohydrate was replaced by the appropriate amino acid derivative, and 3-(trifluoromethyl)benzyl amine was replaced with the appropriate amine.

Example 7

N-Benzyloxycarbonyl-D-glutamic acid γ-t-butyl ester α-(3-trifluoromethyl)benzylamide. N-benzyloxycarbonyl-D-glutamic acid γ-t-butyl ester (1.14 g, 3.37 mmol) and 0.53 mL (3.70 mmol, Novabiochem) of 3-(trifluoromethyl)benzylamine gave 1.67 g (quantitative yield) of Example 7 as an off-white solid. Example 7 exhibited an $^1$H NMR spectrum consistent with the assigned structure.

Example 7A

N-Benzyloxycarbonyl-L-glutamic acid α-t-butyl ester γ-(4-cyclohexyl)piperazinamide. N-benzyloxycarbonyl-L-glutamic acid α-t-butyl ester (1.36 g, 4.03 mmol) and 0.746 g (4.43 mmol) of 1-cyclohexylpiperazine gave 1.93 g (98%) of Example 7A as an off-white solid; $^1$H NMR (CDCl$_3$) δ 1.02-1.12 (n, 5H); 1.43 (s, 9H), 1.60-1.64 (m, 1H); 1.80-1.93 (m, 5H); 2.18-2.52 (m, 8H); 3.38-3.60 (m, 4H); 4.20-4.24 (m, 1H); 5.03-5.13 (m, 2H); 5.53-5.57 (m, 1H); 7.28-7.34 (m, 5H).

Example 7B

N-Benzyloxycarbonyl-D-aspartic acid β-t-butyl ester α-(2-fluoro-3-trifluoromethyl)benzylamide. N-benzyloxycarbonyl-D-aspartic acid β-t-butyl ester monohydrate (Novabiochem) (0.25 g, 0.73 mmol) and 0.12 mL of (2-fluoro-3-trifluoromethyl)benzylamine gave 0.365 g (quantitative yield) of Example 7B as an off-white solid; $^1$H NMR (CDCl$_3$) δ 1.38 (s, 9H); 2.59 (dd, J=6.5 Hz, J=17.0 Hz, 1H); 2.95 (dd, J=4.3 Hz, J=17.0 Hz, 1H); 4.46-4.56 (m, 3H); 5.11 (s, 2H); 5.94-5.96 (m, 1H); 7.15 (t, J=8.0 Hz, 1H); 7.30-7.36 (m, 5H); 7.47-7.52 (m, 2H).

Example 7C

N-Benzyloxycarbonyl-D-aspartic acid β-t-butyl ester α-[(S)-α-methylbenzyl]amide. N-benzyloxycarbonyl-D-aspartic acid β-t-butyl ester monohydrate (Novabiochem) (0.25 g, 0.73 mmol) and 0.094 mL of (S)-α-methylbenzylamine gave 0.281 g (90%) of Example 7C as an off-white solid; $^1$H NMR (CDCl$_3$) δ 1.41 (s, 9H); 1.44 (d, J=7.0 Hz, 3H); 2.61 (dd, J=7.0 Hz, J=17.0 Hz, 1H); 2.93 (dd, J=4.0 Hz, J=17.5 Hz, 1H); 4.50-4.54 (m, 1H); 5.04-5.14 (m, 3H); 5.94-5.96 (m, 1H); 6.76-6.80 (m, 1H); 7.21-7.37 (m, 10H).

Example 7D

N-Benzyloxycarbonyl-D-aspartic acid β-t-butyl ester α-[(R)-α-methylbenzyl]amide. N-benzyloxycarbonyl-D-aspartic acid β-t-butyl ester monohydrate (Novabiochem) (0.25 g, 0.73 mmol) and 0.094 mL of (R)-α-methylbenzylamine gave 0.281 g (90%) of Example 7D as an off-white solid; ¹H NMR (CDCl₃) δ 1.38 (s, 9H); 1.43 (d, J=6.9 Hz, 3H); 2.54 (dd, J=7.3 Hz, J=17.2 Hz, 1H); 2.87 (dd, J=4.1 Hz, J=17.3 Hz, 1H); 4.46-4.50 (m, 1H); 4.99-5.15 (m, 3H); 5.92-5.96 (m, 1H); 6.78-6.82 (m, 1H); 7.21-7.33 (m, 10H).

Example 7E

N-Benzyloxycarbonyl-D-aspartic acid γ-t-butyl ester α-[N-methyl-N-(3-trifluoromethylbenzyl)]amide. N-benzyloxycarbonyl-D-aspartic acid γ-t-butyl ester (0.303 g, 0.89 mmol, Novabiochem) and 0.168 g (0.89 mmol) of N-methyl-N-(3-trifluoromethylbenzyl)amine gave 0.287 g (65%) of Example 7E as an off-white solid; ¹H NMR (CDCl₃) δ 1.40 (s, 9H); 2.55 (dd, J=5.8 Hz, J=15.8 Hz, 1H); 2.81 (dd, J=7.8 Hz, J=15.8 Hz, 1H); 3.10 (s, 3H); 4.25 (d, J=15.0 Hz, 1H); 4.80 (d, J=15.5 Hz, 1H); 5.01-5.13 (m, 3H); 5.52-5.55 (m, 1H); 7.25-7.52 (m, 10H).

Example 7F

N-Benzyloxycarbonyl-D-aspartic acid β-t-butyl ester α-[(S)-1-(3-trifluoromethylphenyl)ethyl]amide. N-benzyloxycarbonyl-D-aspartic acid β-t-butyl ester monohydrate (Novabiochem) (84 mg, 0.25 mmol) and 47 mg of (S)-1-(3-trifluoromethylphenyl)ethylamine gave 122 mg (quantitative yield) of Example 7F as an off-white solid. Example 7F exhibited an ¹H NMR spectrum consistent with the assigned structure.

Example 7G

N-Benzyloxycarbonyl-D-aspartic acid β-t-butyl ester α-[(R)-1-(3-trifluoromethylphenyl)ethyl]amide. N-benzyloxycarbonyl-D-aspartic acid β-t-butyl ester monohydrate (Novabiochem) (150 mg, 0.44 mmol) and 83 mg of (R)-1-(3-trifluoromethylphenyl)ethylamine gave 217 mg (quantitative yield) of Example 7G as an off-white solid. Example 7G exhibited an ¹H NMR spectrum consistent with the assigned structure.

Example 7H

N-Benzyloxycarbonyl-D-glutamic acid α-methyl ester γ-(3-trifluoromethyl)benzylamide. N-benzyloxycarbonyl-D-glutamic acid α-methyl ester (508 mg, 1.72 mmol) and 317 mg (1.81 mmol) of 3-(trifluoromethyl)benzylamine gave 662 mg (85%) of Example 7H as an off-white solid. Example 7H exhibited an ¹H NMR spectrum consistent with the assigned structure.

Example 8

General procedure for hydrogenation of a benzyloxycarbonyl amine. L-aspartic acid β-t-butyl ester α-(3-trifluoromethyl)benzylamide. A suspension of 2.23 g (4.64 mmol) of N-benzyloxycarbonyl-L-aspartic acid β-t-butyl ester α-(3-trifluoromethyl)benzylamide and palladium (5% wt. on activated carbon, 0.642 g) in 30 mL of methanol was held under an atmosphere of hydrogen until complete conversion as determined by thin layer chromatography (95:5 dichloromethane/methanol eluent). The reaction was filtered to remove the palladium over carbon and the filtrate was evaporated to give 1.52 g (96%) of the title compound as an oil; ¹H NMR (CDCl₃) δ 1.42 (s, 9H); 2.26 (brs, 2H); 2.63-2.71 (m, 1H); 2.82-2.87 (m, 1H); 3.75-3.77 (m, 1H); 4.47-4.50 (m, 2H); 7.41-7.52 (m, 4H); 7.90 (brs, 1H).

Examples 9-13P were prepared according to the procedure of Example 8, except that N-benzyloxycarbonyl-L-aspartic acid β-t-butyl ester α-(3-trifluoromethyl)benzylamide was replaced by the appropriate amino acid derivative.

Example 9

L-aspartic acid β-t-butyl ester α-[4-(2-phenylethyl)]piperazinamide. N-benzyloxycarbonyl-L-aspartic acid β-t-butyl ester α-[4-(2-phenylethyl)]piperazinamide (5.89 g, 11.9 mmol) gave 4.24 g (98%) of Example 9 as an off-white oil; ¹H NMR (CDCl₃): δ 1.42 (s, 9H); 2.61-2.95 (m, 10H); 3.60-3.90 (m, 4H); 4.35-4.45 (m, 1H); 7.17-7.29 (m, 5H).

Example 10

D-aspartic acid β-t-butyl ester α-(3-trifluoromethyl)benzylamide. N-benzyloxycarbonyl-D-aspartic acid β-t-butyl ester α-(3-trifluoromethyl)benzylamide (1.41 g, 2.93 mmol) gave 0.973 g (96%) of Example 10 as an off-white oil; ¹H NMR (CDCl₃): δ 1.42 (s, 9H); 2.21 (brs, 2H); 2.67 (dd, J=7.1 Hz, J=16.8 Hz, 1H); 2.84 (dd, J=3.6 Hz, J=16.7 Hz, 1H); 3.73-3.77 (m, 1H); 4.47-4.50 (m, 2H); 7.41-7.52 (m, 4H); 7.83-7.87 (m, 1H).

Example 11

L-glutamic acid γ-t-butyl ester α-(3-trifluoromethyl)benzylamide. N-benzyloxycarbonyl-L-glutamic acid γ-t-butyl ester α-(3-trifluoromethyl)benzylamide (5.41 g, 10.9 mmol) gave 3.94 g (quantitative yield) of Example 11 as an off-white oil; ¹H NMR (CDCl₃) δ 1.41 (s, 9H); 1.73-1.89 (m, 3H); 2.05-2.16 (m, 1H); 2.32-2.38 (m, 2H); 3.47 (dd, J=5.0 Hz, J=7.5 Hz, 1H); 4.47-4.49 (m, 2H); 7.36-7.54 (m, 4H); 7.69-7.77 (m, 1H).

Example 12

L-glutamic acid γ-t-butyl ester α-[4-(2-phenylethyl)]piperazinamide. N-benzyloxycarbonyl-L-glutamic acid γ-t-butyl ester α-[4-(2-phenylethyl)]piperazinamide (5.86 g, 11.50 mmol) gave 4.28 g (99%) of Example 12 as an off-white oil; ¹H NMR (CDCl₃) δ 1.39 (s, 9H); 2.00-2.08 (m, 1H); 2.38-2.46 (m, 1H); 2.55-2.90 (m, 9H); 3.61-3.82 (m, 4H); 4.48-4.56 (m, 1H); 7.17-7.26 (m, 5H).

Example 13

D-glutamic acid γ-t-butyl ester α-(3-trifluoromethyl)benzylamide. N-benzyloxycarbonyl-D-glutamic acid γ-t-butyl ester α-(3-trifluoromethyl)benzylamide (1.667 g, 3.37 mmol) gave 1.15 g (94%) of Example 13 as an off-white oil; ¹H NMR (CDCl₃) δ 1.41 (s, 9H); 1.80-2.20 (m, 4H); 2.31-2.40 (m, 2H); 3.51-3.59 (m, 1H); 4.47-4.49 (m, 2H); 7.39-7.52 (m, 4H); 7.71-7.79 (m, 1H).

Example 13A

L-glutamic acid α-t-butyl ester γ-(4-cyclohexyl)piperazinamide. N-Benzyloxycarbonyl-L-glutamic acid α-t-butyl ester γ-(4-cyclohexyl)piperazinamide (1.93 g, 3.96 mmol) gave 1.30 g (93%) of Example 13A as an off-white oil; ¹H NMR (CDCl₃) δ 1.02-1.25 (m, 5H); 1.41 (s, 9H); 1.45-1.50

(m, 1H); 1.56-1.60 (m, 1H); 1.69-1.80 (m, 6H); 3.30 (dd, J=4.8 Hz, J=8.5 Hz, 1H); 3.44 (t, J=9.9 Hz, 2H); 3.56 (t, J=9.9 Hz, 2H).

Example 13B

D-aspartic acid β-t-butyl ester α-(2-fluoro-3-trifluoromethyl)benzylamide. N-benzyloxycarbonyl-D-aspartic acid β-t-butyl ester α-(2-fluoro-3-trifluoromethyl)benzylamide (0.36 g, 0.72 mmol) gave 0.256 g (92%) of Example 13B as an off-white oil; $^1$H NMR (CDCl$_3$) δ 1.39 (s, 9H); 2.50 (brs, 2H); 2.74 (dd, J=7.0 Hz, J=16.5 Hz, 1H); 2.86 (dd, J=4.8 Hz, J=16.8 Hz, 1H); 3.89 (brs, 2H); 4.47-4.57 (m, 2H); 7.16 (t, J=7.8 Hz, 1H); 7.48 (t, J=7.3 Hz, 1H); 7.56 (t, J=7.3 Hz, 1H); 7.97-8.02 (m, 1H).

Example 13C

D-aspartic acid β-t-butyl ester α-[(S)-α-methyl]benzylamide. N-benzyloxycarbonyl-D-aspartic acid β-t-butyl ester α-[(S)-α-methylbenzyl]amide (0.275 g, 0.65 mmol) gave 0.17 g (90%) of Example 13C as an off-white oil; $^1$H NMR (CDCl$_3$) δ 1.40 (s, 9H); 1.47 (d, J=6.9 Hz, 3H); 1.98 (brs, 2H); 2.49 (dd, J=7.9 Hz, J=17.7 Hz, 1H); 2.83 (dd, J=3.6 Hz, J=16.7 Hz, 1H); 3.69 (brs, 1H); 4.99-5.10 (m, 1H); 7.19-7.33 (m, 5H); 7.65-7.68 (m, 1H).

Example 13D

D-aspartic acid β-t-butyl ester α-[(R)-α-methylbenzyl]amide. N-benzyloxycarbonyl-D-aspartic acid β-t-butyl ester α-[(R)-α-methylbenzyl]amide (0.273 g, 0.64 mmol) gave 0.187 g (quantitative yield) of Example 13D as an off-white oil; $^1$H NMR (CDCl$_3$) δ 1.38 (s, 9H); 1.46 (d, J=6.9 Hz, 3H); 1.79 (brs, 2H); 2.51 (dd, J=7.8 Hz, J=17.5 Hz, 1H); 2.87 (dd, J=3.6 Hz, J=16.9 Hz, 1H); 4.19 (brs, 1H); 4.99-5.11 (m, 1H); 7.18-7.34 (m, 5H); 7.86-7.90 (m, 1H).

Example 13E

D-aspartic acid β-t-butyl ester α-[N-methyl-N-(3-trifluoromethylbenzyl)]amide. N-benzyloxycarbonyl-D-aspartic acid β-t-butyl ester α-[N-methyl-N-(3-trifluoromethylbenzyl)]amide (0.282 g, 0.57 mmol) gave 0.195 g (95%) of Example 13E as an off-white oil. Example 13E exhibited an $^1$H NMR spectrum consistent with the assigned structure.

Example 13F

L-aspartic acid β-t-butyl ester α-[4-(2-phenylethyl)]piperazinamide. N-benzyloxycarbonyl-L-aspartic acid β-t-butyl ester α-[4-(2-phenylethyl)]piperazinamide (5.89 g, 11.9 mmol) gave 4.24 g (98%) of Example 13F as an off-white oil; $^1$H NMR (CDCl$_3$): δ 1.42 (s, 9H); 2.61-2.95 (m, 10H); 3.60-3.90 (m, 4H); 4.35-4.45 (m, 1H); 7.17-7.29 (m, 5H).

Example 13G

D-aspartic acid β-t-butyl ester α-(3-trifluoromethyl)benzylamide. N-benzyloxycarbonyl-D-aspartic acid β-t-butyl ester α-(3-trifluoromethyl)benzylamide (1.41 g, 2.93 mmol) gave 0.973 g (96%) of Example 13G as an off-white oil; $^1$H NMR (CDCl$_3$): δ 1.42 (s, 9H); 2.21 (brs, 2H); 2.67 (dd, J=7.1 Hz, J=16.8 Hz, 1H); 2.84 (dd, J=3.6 Hz, J=16.7 Hz, 1H); 3.73-3.77 (m, 1H); 4.47-4.50 (m, 2H); 7.41-7.52 (m, 4H); 7.83-7.87 (m, 1H).

Example 13H

L-glutamic acid γ-t-butyl ester α-(3-trifluoromethyl)benzylamide. N-benzyloxycarbonyl-L-glutamic acid γ-t-butyl ester α-(3-trifluoromethyl)benzylamide (5.41 g, 10.9 mmol) gave 3.94 g (quantitative yield) of Example 13H as an off-white oil; $^1$H NMR (CDCl$_3$): δ 1.41 (s, 9H); 1.73-1.89 (m, 3H); 2.05-2.16 (m, 1H); 2.32-2.38 (m, 2H); 3.47 (dd, J=5.0 Hz, J=7.5 Hz, 1H); 4.47-4.49 (m, 2H); 7.36-7.54 (m, 4H); 7.69-7.77 (m, 1H).

Example 13I

L-glutamic acid γ-t-butyl ester α-[4-(2-phenylethyl)]piperazinamide. N-benzyloxycarbonyl-L-glutamic acid γ-t-butyl ester α-[4-(2-phenylethyl)]piperazinamide (5.86 g, 11.50 mmol) gave 4.28 g (99%) of Example 13I as an off-white oil; $^1$H NMR (CDCl$_3$) δ 1.39 (s, 9H); 2.00-2.08 (m, 1H); 2.38-2.46 (m, 1H); 2.55-2.90 (m, 9H); 3.61-3.82 (m, 4H); 4.48-4.56 (m, 1H); 7.17-7.26 (m, 5H).

Example 13J

D-glutamic acid γ-t-butyl ester α-(3-trifluoromethyl)benzylamide. N-benzyloxycarbonyl-D-glutamic acid γ-t-butyl ester α-(3-trifluoromethyl)benzylamide (1.667 g, 3.37 mmol) gave 1.15 g (94%) of Example 13J as an off-white oil; $^1$H NMR (CDCl$_3$) δ 1.41 (s, 9H); 1.80-2.20 (m, 4H); 2.31-2.40 (m, 2H); 3.51-3.59 (m, 1H); 4.47-4.49 (m, 2H); 7.39-7.52 (m, 4H); 7.71-7.79 (m, 1H).

Example 13K

L-glutamic acid α-t-butyl ester γ-(4-cyclohexyl)piperazinamide. N-Benzyloxycarbonyl-L-glutamic acid α-t-butyl ester γ-(4-cyclohexyl)piperazinamide (1.93 g, 3.96 mmol) gave 1.30 g (93%) of Example 13K as an off-white oil; $^1$H NMR (CDCl$_3$) δ 1.02-1.25 (m, 5H); 1.41 (s, 9H); 1.45-1.50 (m, 1H); 1.56-1.60 (m, 1H); 1.69-1.80 (m, 6H); 3.30 (dd, J=4.8 Hz, J=8.5 Hz, 1H); 3.44 (t, J=9.9 Hz, 2H); 3.56 (t, J=9.9 Hz, 2H).

Example 13L

D-aspartic acid β-t-butyl ester α-(2-fluoro-3-trifluoromethyl)benzylamide. N-benzyloxycarbonyl-D-aspartic acid β-t-butyl ester α-(2-fluoro-3-trifluoromethyl)benzylamide (0.36 g, 0.72 mmol) gave 0.256 g (92%) of Example 13L as an off-white oil; $^1$H NMR (CDCl$_3$) δ 1.39 (s, 9H); 2.50 (brs, 2H); 2.74 (dd, J=7.0 Hz, J=16.5 Hz, 1H); 2.86 (dd, J=4.8 Hz, J=16.8 Hz, 1H); 3.89 (brs, 2H); 4.47-4.57 (m, 2H); 7.16 (t, J=7.8 Hz, 1H); 7.48 (t, J=7.3 Hz, 1H); 7.56 (t, J=7.3 Hz, 1H); 7.97-8.02 (m, 1H).

Example 13M

D-aspartic acid β-t-butyl ester α-[(S)-1-(3-trifluoromethylphenyl)ethyl]amide. N-benzyloxycarbonyl-D-aspartic acid β-t-butyl ester α-[(S)-1-(3-trifluoromethylphenyl)ethyl]amide (120 mg, 0.24 mmol) gave 91 mg (91%) of Example 13M as an off-white oil, and exhibited an $^1$H NMR spectrum consistent with the assigned structure.

Example 13N

D-aspartic acid β-t-butyl ester α-[(R)-1-(3-trifluoromethylphenyl)ethyl]amide. N-benzyloxycarbonyl-D-aspartic acid β-t-butyl ester α-[(R)-1-(3-trifluoromethylphenyl)ethyl]amide (217 mg, 0.44 mmol) gave 158 mg (quantitative yield) of Example 13N as an off-white oil, and exhibited an $^1$H NMR spectrum consistent with the assigned structure.

Example 130

D-aspartic acid β-t-butyl ester α-[N-methyl-N-(3-trifluoromethylbenzyl)]amide. N-benzyloxycarbonyl-D-aspartic acid β-t-butyl ester α-[N-methyl-N-(3-trifluoromethylbenzyl)]amide (0.282 g, 0.57 mmol) gave 0.195 g (95%) of Example 130 as an off-white oil, and exhibited an $^1$H NMR spectrum consistent with the assigned structure.

Example 13P

D-glutamic acid α-methyl ester γ-(3-trifluoromethyl)benzylamide. N-Benzyloxycarbonyl-D-glutamic acid α-methyl ester γ-(3-trifluoromethyl)benzylamide (764 mg, 1.69 mmol) gave g (516 mg, 96%) of Example 13P as an off-white oil, and exhibited an $^1$H NMR spectrum consistent with the assigned structure.

Example 14

General procedure for formation of a 2-azetidinone from an imine and an acetyl chloride.
Step 1: General procedure for formation of an imine from an amino acid derivative. A solution of 1 equivalent of an α-amino acid ester or amide in dichloromethane is treated sequentially with 1 equivalent of an appropriate aldehyde, and a dessicating agent, such as magnesium sulfate or silica gel, in the amount of about 2 grams of dessicating agent per gram of starting α-amino acid ester or amide. The reaction is stirred at ambient temperature until all of the reactants are consumed as measured by thin layer chromatography. The reactions are typically complete within an hour. The reaction mixture is then filtered, the filter cake is washed with dichloromethane, and the filtrate concentrated under reduced pressure to provide the desired imine that is used as is in the subsequent step. Step 2: General procedure for the 2+2 cycloaddition of an imine and an acetyl chloride. A dichloromethane solution of the imine (10 mL dichloromethane/1 gram imine) is cooled to 0° C. To this cooled solution is added 1.5 equivalents of an appropriate amine, typically triethylamine, followed by the dropwise addition of a dichloromethane solution of 1.1 equivalents of an appropriate acetyl chloride, such as that described in Example 1 (10 mL dichloromethane/1 gm appropriate acetyl chloride). The reaction mixture is allowed to warm to ambient temperature over 1 h and is then quenched by the addition of a saturated aqueous solution of ammonium chloride. The resulting mixture is partitioned between water and dichloromethane. The layers are separated and the organic layer is washed successively with 1N hydrochloric acid, saturated aqueous sodium bicarbonate, and saturated aqueous sodium chloride. The organic layer is dried over magnesium sulfate and concentrated under reduced pressure. The residue may be used directly for further reactions, or purified by chromatography or by crystallization from an appropriate solvent system if desired. In each case, following the 2+2 reaction, the stereochemistry of the β-lactam may be confirmed by circular dichroism/optical rotary dispersion (CD/ORD). Illustratively, examples of the (αR,3S,4R) and (αS,3S,4R) β-lactam platform stereochemical configurations from prior syntheses may be used as CD/ORD standards.

Example 15 tert-Butyl [3(S)-(4(S)-phenyloxazolidin-2-on-3-yl)-4(R)-(2-styryl)azetidin-2-on-1-yl]acetate. Using the procedure of Example 14, the imine prepared from 4.53 g (34.5 mmol) glycine tert-butyl ester and cinnamaldehyde was combined with 2-(4(S)-phenyloxazolidin-2-on-3-yl) acetyl chloride (Example 1) to give 5.5 g (30%) of Example 15 as colorless crystals (recrystallized, n-chlorobutane); mp 194-195° C.

Example 16

General procedure for acylation of an azetidin-2-on-1-ylacetate. A solution of (azetidin-2-on-1-yl)acetate in tetrahydrofuran (0.22 M in azetidinone) is cooled to −78° C. and is with lithium bis(trimethylsilyl)amide (2.2 equivalents). The resulting anion is treated with an appropriate acyl halide (1.1 equivalents). Upon complete conversion of the azetidinone, the reaction is quenched with saturated aqueous ammonium chloride and partitioned between ethyl acetate and water. The organic phase is washed sequentially with 1N hydrochloric acid, saturated aqueous sodium bicarbonate, and saturated aqueous sodium chloride. The resulting organic layer is dried (magnesium sulfate) and evaporated. The residue is purified by silica gel chromatography with an appropriate eluent, such as 3:2 hexane/ethyl acetate.

Example 17. 2,2,2-Trichloroethyl 2(RS)-(tert-butoxycarbonyl)-2-[3(S)-(4(S)-phenyloxazolidin-2-on-3-yl)-4(R)-(2-styryl)azetidin-2-on-1-yl]acetate Using the procedure of Example 16, 9.0 g (20 mmol) of Example 15 was acylated with 4.2 g (20 mmol) of trichloroethylchloroformate to give 7.0 g (56%) of Example 17; mp 176-178° C.

Example 18

2(RS)-(tert-Butoxycarbonyl)-2-[3(S)-(4(S)-phenyloxazolidin-2-on-3-yl)-4(R)-(2-styryl)azetidin-2-on-1-yl]acetic acid N-(3-trifluoromethylbenzyl)amide. A solution of 0.20 g (0.32 mmol) of Example 17 and 52 µL (0.36 mmol) of (3-trifluoromethylbenzyl)amine in THF was heated at reflux. Upon complete conversion (TLC), the solvent was evaporated and the residue was recrystallized (chloroform/hexane) to give 0.17 g (82%) of Example 18 as a white solid; mp 182-184° C.

Example 18A

2(RS)-(tert-Butoxycarbonyl)-2-[3(S)-(4(S)-phenyloxazolidin-2-on-3-yl)-4(R)-(2-styryl)azetidin-2-on-1-yl]acetic acid N-(2-fluoro-3-trifluoromethylbenzyl)amide. Example 18A was prepared according to the procedure of Example 18, using 2-fluoro-3-(trifluoromethyl)benzylamine instead of (3-trifluoromethylbenzyl)amine. Example 18A was obtained as a white solid (140 mg, 41%), and exhibited an $^1$H NMR spectrum consistent with the assigned structure.

Examples 19-25AF were prepared according to the procedure of Example 14, where the appropriate amino acid derivative and aldehyde were used in Step 1, and the appropriate acetyl chloride was used in Step 2.

Example 19

2(S)-(tert-Butoxycarbonylmethyl)-2-[3(S)-(4(S)-phenyloxazolidin-2-on-3-yl)-4(R)-(2-styryl)azetidin-2-on-1-yl]

acetic acid N-(3-trifluoromethylbenzyl)amide. The imine prepared from 1.52 g (4.39 mmol) of L-aspartic acid β-t-butyl ester t-(3-trifluoromethyl)benzylamide and cinnamaldehyde was combined with 2-(4(S)-phenyloxazolidin-2-on-3-yl) acetyl chloride (Example 1) to give 2.94 g of an orange-brown oil that gave, after flash column chromatography purification (70:30 hexanes/ethyl acetate), 2.06 g (70%) of Example 19 as a white solid; $^1$H NMR (CDCl$_3$) δ 1.39 (s, 9H); 2.46 (dd, J=11.1 Hz, J=16.3 Hz, 1H); 3.18 (dd, J=3.8 Hz, J=16.4 Hz, 1H); 4.12-4.17 (m, 1H); 4.26 (d, J=5.0 Hz, 1H); 4.45 (dd, J=6.0 Hz, J=14.9 Hz, 1H); 4.54 (dd, J=5.3 Hz, J=9.8 Hz, 1H); 4.58-4.66 (m, 3H); 4.69-4.75 (m, 1H); 4.81 (dd, J=3.8 Hz, J=11.1 Hz, 1H); 6.25 (dd, J=9.6 Hz, J=15.8 Hz, 1H); 6.70 (d, J=15.8 Hz, 1H); 7.14-7.17 (m, 2H); 7.28-7.46 (m, 11H); 7.62 (s, 1H); 8.27-8.32 (m, 1H).

Example 19A

2(S)-(tert-Butoxycarbonylmethyl)-2-[3(R)-(4(R)-phenyloxazolidin-2-on-3-yl)-4(S)-(2-styryl)azetidin-2-on-1-yl] acetic acid N-(3-trifluoromethylbenzyl)amide. Example 19A was prepared according to the method of Example 19 except that 2-(4(R)-phenyloxazolidin-2-on-3-yl) acetyl chloride (Example 1A) was used instead of 2-(4(S)-phenyloxazolidin-2-on-3-yl) acetyl chloride. Example 19A was obtained as a white solid (41 mg, 13%); $^1$H NMR (CDCl$_3$) δ 1.37 (s, 9H); 3.11 (dd, J=3.7 Hz, J=17.8 Hz, 1H); 3.20 (dd, J=10.6 Hz, J=17.8 Hz, 1H); 4.02 (dd, J=3.7 Hz, J=10.6 Hz, 1H); 4.10-4.17 (m, 1H); 4.24 (d, J=4.9 Hz, 1H); 4.4652-4.574 (dd, J=5.9 Hz, J=15.1 Hz, 1H); 4.58-4.76 (m, 4H); 6.27 (dd, J=9.6 Hz, J=15.8 Hz, 1H); 6.79 (d, J=15.8 Hz, 1H); 7.23-7.53 (m, 13H); 7.63 (s, 1H); 8.51-8.55 (m, 1H).

Example 20

2(S)-(tert-Butoxycarbonylethyl)-2-[3(S)-(4(S)-phenyloxazolidin-2-on-3-yl)-4(R)-(2-styryl)azetidin-2-on-1-yl] acetic acid N-(3-trifluoromethylbenzyl)amide. The imine prepared from 3.94 g (10.93 mmol) of L-glutamic acid γ-t-butyl ester α-(3-trifluoromethyl)benzylamide and cinnamaldehyde was combined with 2-(4(S)-phenyloxazolidin-2-on-3-yl) acetyl chloride (Example 1) to give 5.53 g (75%) of Example 20 after flash column chromatography purification (70:30 hexanes/ethyl acetate); $^1$H NMR (CDCl$_3$) δ 1.36 (s, 9H); 1.85-1.96 (m, 1H); 2.18-2.49 (m, 3H); 4.14-4.19 (m, 1H); 4.30 (d, J=4.9 Hz, 2H); 4.44 (dd, J=6.1 Hz, J=14.9 Hz, 1H); 4.56-4.67 (m, 4H); 4.71-4.75 (m, 1H); 6.26 (dd, J=9.6 Hz, J=15.8 Hz, 1H); 6.71 (d, J=15.8 Hz, 1H); 7.16-7.18 (m, 2H); 7.27-7.49 (m, 11H); 7.60 (s, 1H); 8.08-8.12 (m, 1H).

Example 21

2(S)-(tert-Butoxycarbonylmethyl)-2-[3(S)-(4(S)-phenyloxazolidin-2-on-3-yl)-4(R)-(2-styryl)azetidin-2-on-1-yl] acetic acid N-[4-(2-phenylethyl)]piperazinamide. The imine prepared from 4.20 g (11.6 mmol) of L-aspartic acid β-t-butyl ester α-[4-(2-phenylethyl)]piperazinamide and cinnamaldehyde was combined with 2-(4(S)-phenyloxazolidin-2-on-3-yl) acetyl chloride (Example 1) to give 4.37 g (55%) of Example 21 after flash column chromatography purification (50:50 hexanes/ethyl acetate); $^1$H NMR (CDCl$_3$) δ 1.34 (s, 9H); 2.26-2.32 (m, 1H); 2.46-2.63 (m, 4H); 2.75-2.89 (m, 4H); 3.24-3.32 (m, 1H); 3.49-3.76 (m, 3H); 4.07-4.13 (m, 1H); 4.30 (d, J=4.6 Hz, 1H); 4.22-4.48 (m, 1H); 4.55-4.61 (m, 1H); 4.69-4.75 (m, 1H); 5.04-5.09 (m, 1H); 6.15 (dd, J=9.3 Hz, J=15.9 Hz, 1H); 6.63 (d, J=15.8 Hz, 1H); 7.18-7.42 (m, 15H).

Example 22

2(S)-(tert-Butoxycarbonylethyl)-2-[3(S)-(4(S)-phenyloxazolidin-2-on-3-yl)-4(R)-(2-styryl)azetidin-2-on-1-yl] acetic acid N-[4-(2-phenylethyl)]piperazinamide. The imine prepared from 2.54 g (6.75 mmol) of L-glutamic acid γ-t-butyl ester α-[4-(2-phenylethyl)]piperazinamide and cinnamaldehyde was combined with 2-(4(S)-phenyloxazolidin-2-on-3-yl) acetyl chloride (Example 1) to give 3.55 g (76%) of Example 22 after flash column chromatography purification (50:50 hexanes/ethyl acetate); $^1$H NMR (CDCl$_3$) δ 1.32 (s, 9H); 1.96-2.07 (m, 1H); 2.15-2.44 (m, 6H); 2.54-2.62 (m, 2H); 2.69-2.81 (m, 3H); 3.28-3.34 (m, 1H); 3.59-3.68 (m, 1H); 4.08-4.13 (m, 1H); 4.33-4.44 (m, 2H); 4.48-4.60 (m, 2H); 4.67-4.77 (m, 1H); 6.14 (dd, J=8.9 Hz, J=16.0 Hz, 1H); 6.62 (d, J=16.0 Hz, 1H); 7.16-7.42 (m, 15H).

Example 23

2(R)-(tert-Butoxycarbonylmethyl)-2-[3(S)-(4(S)-phenyloxazolidin-2-on-3-yl)-4(R)-(2-styryl)azetidin-2-on-1-yl] acetic acid N-(3-trifluoromethylbenzyl)amide. The imine prepared from 0.973 g (2.81 mmol) of D-aspartic acid 3-t-butyl ester α-(3-trifluoromethyl)benzylamide and cinnamaldehyde was combined with 2-(4(S)-phenyloxazolidin-2-on-3-yl) acetyl chloride (Example 1) to give 1.53 g (82%) of Example 23 after flash column chromatography purification (70:30 hexanes/ethyl acetate); $^1$H NMR (CDCl$_3$) δ 1.37 (s, 9H); 3.10 (dd, J=3.7 Hz, J=17.8 Hz, 1H); 3.20 (dd, J=10.7 Hz, J=17.8 Hz, 1H); 4.02 (dd, J=3.6 Hz, J=10.6 Hz, 1H); 4.11-4.17 (m, 1H); 4.24 (d, J=4.9 Hz, 1H); 4.46 (dd, J=5.8 Hz, J=15.1 Hz, 1H); 4.58-4.67 (m, 3H); 4.70-4.76 (m, 1H); 6.27 (dd, J=9.5 Hz, J=15.8 Hz, 1H); 6.79 (d, J=15.8 Hz, 1H); 7.25-7.50 (m, 13H); 7.63 (s, 1H); 8.50-8.54 (m, 1H).

Example 23A

2(R)-(tert-Butoxycarbonylmethyl)-2-[3(R)-(4(R)-phenyloxazolidin-2-on-3-yl)-4(S)-(2-styryl)azetidin-2-on-1-yl] acetic acid N-(3-trifluoromethylbenzyl)amide. Example 23A was prepared according to the method of Example 23 except that 2-(4(R)-phenyloxazolidin-2-on-3-yl) acetyl chloride (Example 1A) was used instead of 2-(4(S)-phenyloxazolidin-2-on-3-yl) acetyl chloride. Example 23A was obtained as a white solid (588 mg, 49%); $^1$H NMR (CDCl$_3$) δ 1.39 (s, 9H); 2.47 (dd, J=11.2 Hz, J=16.3 Hz, 1H); 3.18 (dd, J=3.8 Hz, J=16.3 Hz, 1H); 4.15 (t, J=8.25, Hz 1H); 4.26 (d, J=5.0 Hz, 1H); 4.45 (dd, J=6.0 Hz, J=15.0 Hz, 1H); 4.52-4.57 (m, 3H); 4.63 (t, J=9 Hz, 1H); 4.70 (t, J=8 Hz, 1H); 4.81 (dd, J=3.8 Hz, J=10.8 Hz, 1H); 6.25 (dd, J=9.8 Hz, J=15.8 Hz, 1H); 6.70 (d, J=15.8 Hz, 1H); 7.15-7.17 (m, 2H); 7.27-7.51 (m, 11H); 7.62 (s, 1H); 8.27-8.32 (m, 1H).

Example 24

2(R)-(tert-Butoxycarbonylethyl)-2-[3(S)-(4(S)-phenyloxazolidin-2-on-3-yl)-4(R)-(2-styryl)azetidin-2-on-1-yl] acetic acid N-(3-trifluoromethylbenzyl)amide. The imine prepared from 1.15 g (3.20 mmol) of D-glutamic acid γ-t-butyl ester α-(3-trifluoromethyl)benzylamide and cinnamaldehyde was combined with 2-(4(S)-phenyloxazolidin-2-on-3-yl) acetyl chloride (Example 1) to give 1.84 g (85%) of Example 24 after flash column chromatography purification (70:30 hexanes/ethyl acetate); $^1$H NMR (CDCl$_3$) δ 1.37 (s, 9H); 2.23-2.39 (m, 4H); 3.71-3.75 (m, 1H); 4.13-4.18 (m, 1H); 4.31 (d, J=4.9 Hz, 1H); 4.44-4.51 (m, 2H); 4.56-4.68

(m, 2H); 4.71-4.76 (m, 1H); 6.26 (dd, J=9.5 Hz, J=15.8 Hz, 1H); 6.71 (d, J=15.8 Hz, 1H); 7.25-7.52 (m, 13H); 7.63 (s, 1H); 8.25-8.30 (m, 1H).

Example 25

2(S)-(tert-Butoxycarbonylethyl)-2-[3(S)-(4(S)-phenyloxazolidin-2-on-3-yl)-4(R)-(2-styryl)azetidin-2-on-1-yl] acetic acid N-(4-cyclohexyl)piperazinamide. The imine prepared from 2.58 g (5.94 mmol) of L-glutamic acid γ-t-butyl ester α-(4-cyclohexyl)piperazinamide and cinnamaldehyde was combined with 2-(4(S)-phenyloxazolidin-2-on-3-yl) acetyl chloride (Example 1) to give 3.27 g (94%) of Example 25 after flash column chromatography purification (95:5 dichloromethane/methanol); $^1$H NMR (CDCl$_3$) δ 1.32 (s, 9H); 1.10-1.18 (m, 1H); 1.20-1.31 (m, 2H); 1.38-1.45 (m, 2H); 1.61-1.66 (m, 1H); 1.84-1.89 (m, 2H); 1.95-2.01 (m, 1H); 2.04-2.14 (m, 3H); 2.20-2.24 (m, 1H); 2.29-2.35 (m, 1H); 2.85-2.92 (m, 1H); 3.24-3.32 (m, 1H); 3.36-3.45 (m, 2H); 3.80-3.86 (m, 1H); 4.08 (t, J=8.3 Hz, 1H); 4.27 (d, J=5.0 Hz, 1H); 4.31-4.55 (m, 4H); 4.71 (t, J=8.3 Hz, 1H); 4.83-4.90 (m, 1H); 6.18 (dd, J=9.1 Hz, J=15.9 Hz, 1H); 6.67 (d, J=15.9 Hz, 1H); 7.25-7.44 (m, 10H); 8.22 (brs, 1H).

Example 25A tert-Butyl 2(S)-(2-(4-cyclohexylpiperazinylcarbonyl) ethyl)-2-[3(S)-(4(S)-phenyloxazolidin-2-on-3-yl)-4(R)-(2-styryl)azetidin-2-on-1-yl]acetate. The imine prepared from 1.282 g (3.63 mmol) of L-glutamic acid α-t-butyl ester γ-(4-cyclohexyl)piperazinamide and cinnamaldehyde was combined with 2-(4(S)-phenyloxazolidin-2-on-3-yl) acetyl chloride (Example 1) to give 1.946 g (80%) of Example 25A after flash column chromatography purification (50:50 hexanes/ethyl acetate); $^1$H NMR (CDCl$_3$) δ 1.15-1.26 (m, 6H); 1.39 (s, 9H); 1.55-1.64 (m, 2H); 1.77-1.83 (m, 3H); 2.22-2.35 (m, 2H); 2.40-2.50 (m, 6H); 2.75-2.79 (m, 1H); 3.43-3.48 (m, 1H); 3.56-3.60 (m, 2H); 3.75-3.79 (m, 1H); 4.10 (t, J=8.3 Hz, 1H); 4.31-4.35 (m, 2H); 4.58 (t, J=8.8 Hz, 1H); 4.73 (t, J=8.4 Hz, 1H); 6.17 (dd, J=8.6 Hz, J=16.0 Hz, 1H); 6.65 (d, J=16.0 Hz, 1H); 7.27-7.42 (m, 10H).

Example 25B

2(R)-(tert-Butoxycarbonylmethyl)-2-[3(S)-(4(S)-phenyloxazolidin-2-on-3-yl)-4(R)-(2-styryl)azetidin-2-on-1-yl] acetic acid N-(2-fluoro-3-trifluoromethylbenzyl)amide. The imine prepared from 0.256 g (0.70 mmol) of D-aspartic acid 3-t-butyl ester α-(2-fluoro-3-trifluoromethyl)benzylamide and cinnamaldehyde was combined with 2-(4(S)-phenyloxazolidin-2-on-3-yl) acetyl chloride (Example 1) to give 0.287 g (60%) of Example 25B after flash column chromatography purification (70:30 hexanes/ethyl acetate); $^1$H NMR (CDCl$_3$) δ 1.38 (s, 9H); 3.12 (dd, J=4.0 Hz, J=17.8 Hz, 1H); 3.20 (dd, J=10.4 Hz, J=17.8 Hz, 1H); 4.05 (dd, J=3.9 Hz, J=10.4 Hz, 1H); 4.14 (dd, J=J'=8.2 Hz, 1H); 4.25 (d, J=4.9 Hz, 1H); 4.59-4.67 (m, 4H); 4.74 (t, J=8.3 Hz, 1H); 6.36 (dd, J=9.6 Hz, J=15.8 Hz, 1H); 6.83 (d, J=15.8 Hz, 1H); 7.02-7.07 (m, 1H); 7.28-7.55 (m, 12H); 8.44-8.48 (m, 1H).

Example 25C

2(R)-(tert-Butoxycarbonylmethyl)-2-[3(S)-(4(S)-phenyloxazolidin-2-on-3-yl)-4(R)-(2-styryl)azetidin-2-on-1-yl] acetic acid N—[(S)-α-methylbenzyl]amide. The imine prepared from 0.167 g (0.57 mmol) of D-aspartic acid β-t-butyl ester [(S)-α-methylbenzyl]amide and cinnamaldehyde was combined with 2-(4(S)-phenyloxazolidin-2-on-3-yl) acetyl chloride (Example 1) to give 0.219 g (63%) of Example 25C after flash column chromatography purification (70:30 hexanes/ethyl acetate); $^1$H NMR (CDCl$_3$) δ 1.35 (s, 9H); 1.56 (d, J=7.0 Hz, 3H); 2.97 (dd, J=3.5 Hz, J=18.0 Hz, 1H); 3.15 (dd, J=11.0 Hz, J=17.5 Hz, 1H); 4.01 (dd, J=3.0 Hz, J=11.0 Hz, 1H); 4.14 (t, J=8.5 Hz, 1H); 4.24 (d, J=5.0 Hz, 1H); 4.57 (dd, J=5.0 Hz, J=9.5 Hz, 1H); 4.64 (t, J=8.8 Hz, 1H); 5.07 (t, J=8.5 Hz, 1H); 5.03-5.09 (m, 1H); 6.43 (dd, J=9.5 Hz, J=16.0 Hz, 1H); 6.83 (d, J=16.0 Hz, 1H); 7.16-7.20 (m, 1H); 7.27-7.49 (m, 14H); 8.07-8.10 (m, 1H).

Example 25D

2(R)-(tert-Butoxycarbonylmethyl)-2-[3(S)-(4(S)-phenyloxazolidin-2-on-3-yl)-4(R)-(2-styryl)azetidin-2-on-1-yl] acetic acid N—[(R)-α-methylbenzyl]amide. The imine prepared from 0.187 g (0.46 mmol) of D-aspartic acid β-t-butyl ester [(R)-α-methylbenzyl]amide and cinnamaldehyde was combined with 2-(4(S)-phenyloxazolidin-2-on-3-yl) acetyl chloride (Example 1) to give 0.25 g (64%) of Example 25D after flash column chromatography purification (70:30 hexanes/ethyl acetate); $^1$H NMR (CDCl$_3$) δ 1.36 (s, 9H); 1.59 (d, J=7.1 Hz, 3H); 3.10 (dd, J=3.5 Hz, J=17.8 Hz, 1H); 3.22 (dd, J=10.9 Hz, J=17.8 Hz, 1H); 3.93 (dd, J=3.5 Hz, J=10.8 Hz, 1H); 4.14 (t, J=8.1 Hz, 1H); 4.24 (d, J=5.0 Hz, 1H); 4.58 (dd, J=5.0 Hz, J=9.5 Hz, 1H); 4.65 (t, J=8.7 Hz, 1H); 4.74 (t, J=8.2 Hz, 1H); 5.06-5.14 (m, 1H); 6.32 (dd, J=9.5 Hz, J=15.8 Hz, 1H); 6.74 (d, J=15.8 Hz, 1H); 7.19-7.43 (m, 15H); 8.15-8.18 (m, 1H).

Example 25E

2(R)-(tert-Butoxycarbonylmethyl)-2-[3(S)-(4(S)-phenyloxazolidin-2-on-3-yl)-4(R)-(2-styryl)azetidin-2-on-1-yl] acetic acid N-methyl-N-(3-trifluoromethylbenzyl)amide. The imine prepared from 0.195 g (0.41 mmol) of D-aspartic acid β-t-butyl ester α-[N-methyl-N-(3-trifluoromethylbenzyl)]amide and cinnamaldehyde was combined with 2-(4 (S)-phenyloxazolidin-2-on-3-yl) acetyl chloride (Example 1) to give 0.253 g (69%) of Example 25E after flash column chromatography purification (70:30 hexanes/ethyl acetate); $^1$H NMR (CDCl$_3$) δ 1.36 (s, 9H); 2.53 (dd, J=4.0 Hz, J=17.0 Hz, 1H); 3.06 (dd, J=10.8 Hz, J=16.8 Hz, 1H); 3.13 (s, 3H); 4.12 (dd, J=8.0 Hz, J=9.0 Hz, 1H); 4.26 (d, J=5.0 Hz, 1H); 4.38 (d, J=15.0 Hz, 1H); 4.46 (d, J=5.0 Hz, J=9.5 Hz, 1H); 4.56 (t, J=6.8 Hz, 1H); 4.70-4.79 (m, 2H); 5.27 (dd, J=4.0 Hz, J=11.0 Hz, 1H); 6.22 (dd, J=9.3 Hz, J=15.8 Hz, 1H); 6.73 (d, J=15.8 Hz, 1H); 7.33-7.45 (m, 14H).

Example 25F

2(S)-(tert-Butoxycarbonylethyl)-2-[3(S)-(4(S)-phenyloxazolidin-2-on-3-yl)-4(R)-(2-chlorostyr-2-yl)azetidin-2-on-1-yl]acetic acid N-(3-trifluoromethylbenzyl)amide. The imine prepared from 1.62 g (4.44 mmol) of L-glutamic acid γ-t-butyl ester α-(3-trifluoromethyl)benzylamide and α-chlorocinnamaldehyde was combined with 2-(4(S)-phenyloxazolidin-2-on-3-yl) acetyl chloride (Example 1) to give 0.708 g (22%) of Example 25F after flash column chromatography purification (70:30 hexanes/ethyl acetate); $^1$H NMR (CDCl$_3$) δ 1.35 (s, 9H); 1.68 (brs, 1H); 2.19-2.35 (m, 2H); 2.40-2.61 (m, 2H); 4.13 (dd, J=7.5 Hz, J=9.0 Hz, 1H); 4.22 (t, J=7.0 Hz, 1H); 4.34 (d, J=4.5 Hz, 1H); 4.45 (dd, J=5.5 Hz, J=15.0 Hz, 1H); 4.51-4.60 (m, 3H); 4.89 (dd, J=7.5 Hz, J=8.5 Hz, 1H); 6.89 (s, 1H); 7.28-7.54 (m, 14H).

Example 25G

2(R)-(tert-Butoxycarbonylmethyl)-2-[3(S)-(4(S)-phenyloxazolidin-2-on-3-yl)-4(R)-(2'-methoxystyr-2-yl)azetidin-2-on-1-yl]acetic acid N-(3-trifluoromethylbenzyl)amide. The imine prepared from 0.34 g (0.98 mmol) of D-aspartic acid 3-t-butyl ester α-(3-trifluoromethylbenzyl)amide and 2'-methoxycinnamaldehyde was combined with 2-(4(S)-phenyloxazolidin-2-on-3-yl) acetyl chloride (Example 1) to give 0.402 g (59%) of Example 25G after flash column chromatography purification (70:30 hexanes/ethyl acetate); $^1$H NMR (CDCl$_3$) δ 1.35 (s, 9H); 1.68 (brs, 1H); 2.19-2.35 (m, 2H); 2.40-2.61 (m, 2H); 4.13 (dd, J=7.5 Hz, J=9.0 Hz, 1H); 4.22 (t, J=7.0 Hz, 1H); 4.34 (d, J=4.5 Hz, 1H); 4.45 (dd, J=5.5 Hz, J=15.0 Hz, 1H); 4.51-4.60 (m, 3H); 4.89 (dd, J=7.5 Hz, J=8.5 Hz, 1H); 6.89 (s, 1H); 7.28-7.54 (m, 14H).

Example 25H tert-Butyl (2R)-(Benzyloxymethyl)-2-[3(S)-(4(S)-phenyloxazolidin-2-on-3-yl)-4(R)-(2-styryl)azetidin-2-on-1-yl]acetate. The imine prepared from 0.329 g (1.31 mmol) of O-(benzyl)-D-serine t-butyl ester (Example 5B) and cinnamaldehyde was combined with 2-(4(S)-phenyloxazolidin-2-on-3-yl) acetyl chloride (Example 1) to give 0.543 g (73%) of Example 25H after flash column chromatography purification (90:10 hexanes/ethyl acetate); $^1$H NMR (CDCl$_3$) δ 1.39 (s, 9H); 3.56 (dd, J=2.7 Hz, J=9.5 Hz, 1H); 3.82 (dd, J=4.8 Hz, J=9.5 Hz, 1H); 4.11 (t, J=8.3 Hz, 1H); 4.21-4.29 (m, 2H); 4.50-4.58 (m, 3H); 4.71-4.78 (m, 2H); 6.19 (dd, J=9.1 Hz, J=16.0 Hz, 1H); 6.49 (d, J=16.0 Hz, 1H); 7.07-7.11 (m, 1H); 7.19-7.40 (m, 14H).

Example 25I tert-Butyl 2(S)-(2-(4-cyclohexylpiperazinylcarbonyl)methyl)-2-[3(S)-(4(S)-phenyloxazolidin-2-on-3-yl)-4(R)-(2-styryl)azetidin-2-on-1-yl]acetate. The imine prepared from 0.3 g (0.88 mmol) of L-aspartic acid α-t-butyl ester γ-(4-cyclohexyl)piperazinamide and cinnamaldehyde was combined with 2-(4(S)-phenyloxazolidin-2-on-3-yl) acetyl chloride (Example 1) to give 464 mg (80%) of Example 25I as a white solid after flash column chromatography purification (50:50 hexanes/ethyl acetate). Example 25I exhibited an $^1$H NMR spectrum consistent with the assigned structure.

Example 25J tert-Butyl 3(R)-[3(S)-(4(S)-phenyloxazolidin-2-on-3-yl)-3-methyl-4(R)-(styr-2-yl)azetidin-2-on-1-yl]-3-[(3-trifluoromethyl)phenylmethylaminocarbonyl]propanoate. The imine prepared from 0.307 g (0.89 mmol) of D-aspartic acid β-t-butyl ester α-(3-trifluoromethyl)benzylamide (Example 20) and cinnamaldehyde was combined with 2-(4(S)-phenyloxazolidin-2-on-3-yl)propanoyl chloride (Example 1E) to give 120 mg (20%) after flash column chromatography purification (hexanes 70%/EtOAc 30%); $^1$H NMR (CDCl$_3$) δ 1.25 (s, 3H), 1.38 (s, 9H); 3.09 (dd, J=3.0 Hz, J=18.0 Hz, 1H); 3.33 (dd, J=12.5 Hz, J=18.0 Hz, 1H); 4.01 (dd, J=3.0 Hz, J=11.5 Hz, 1H); 4.04 (dd, J=3.5 Hz, J=8.8 Hz, 1H); 4.42 (d, J=9.0 Hz, 1H); 4.45-4.51 (m, 3H); 4.61-4.66 (m, 1H); 4.75 (dd, J=3.5 Hz, J=8.5 Hz, 1H); 6.23 (dd, J=9.0 Hz, J=15.5 Hz, 1H); 6.78 (d, J=15.5 Hz, 1H); 7.23-7.53 (m, 13H); 7.64 (s, 1H).

Example 25K

2(R)-(tert-Butoxycarbonylmethyl)-2-[3(S)-(4(S)-phenyloxazolidin-2-on-3-yl)-4(R)-(prop-1-enyl)azetidin-2-on-1-yl]acetic acid N-(3-trifluoromethylbenzyl)amide. The imine prepared from 0.289 g (0.83 mmol) of D-aspartic acid β-t-butyl ester α-(3-trifluoromethyl)benzylamide and crotonaldehyde was combined with 2-(4(S)-phenyloxazolidin-2-on-3-yl) acetyl chloride (Example 1) to give 381 mg (76%) of Example 25K after flash column chromatography purification (99:1 CH$_2$Cl$_2$/MeOH); $^1$H NMR (CDCl$_3$) δ 1.36 (s, 9H), 1.69 (dd, J=2 Hz, J=6.5 Hz, 3H); 3.08 (dd, J=3.3 Hz, J=17.8 Hz, 1H); 3.18 (dd, J=11 Hz, J=17.5 Hz, 1H); 3.94 (dd, J=3.5 Hz, J=11 Hz, 1H); 4.12 (d, J=5 Hz, 1H); 4.15 (dd, J=7 Hz, J=8 Hz, 1H); 4.35 (dd, J=4.8 Hz, J=9.8 Hz, 1H); 4.44 (dd, J=6 Hz, J=15 Hz, 1H); 4.61 (dd, J=6 Hz, J=15 Hz, 1H); 4.67-4.75 (m, 2H); 5.52-5.58 (m, 1H); 5.92-6.00 (m, 1H); 7.33-7.60 (m, 9H); 8.47-8.50 (m, 1H).

Example 25O

Methyl 2(S)-(tert-Butoxycarbonylethyl)-2-[3(S)-(4(S)-phenyloxazolidin-2-on-3-yl)-4(R)-(2-styryl)azetidin-2-on-1-yl]acetate. The imine prepared from 433 mg (1.99 mmol) of L-glutamic acid γ-t-butyl ester α-methyl ester and cinnamaldehyde was combined with 2-(4(S)-phenyloxazolidin-2-on-3-yl) acetyl chloride (Example 1) to give 682 mg (64%) of Example 25O after flash column chromatography purification (70:30 hexanes/ethyl acetate); $^1$H NMR (CDCl$_3$) δ 1.32 (s, 9H); 2.10-2.26 (m, 1H); 2.30-2.41 (m, 3H); 3.66 (s, 3H); 3.95-3.99 (m, 1H); 4.16 (dd, J=7.5 Hz, J=9 Hz, 1H); 4.38 (dd, J=5 Hz, J=9 Hz, 1H); 4.55 (d, J=5 Hz 1H); 4.61 (t, J=9 Hz, 1H); 4.86 (dd, J=7.5 Hz, J=9 Hz, 1H); 6.00 (dd, J=9 Hz, J=16 Hz, 1H); 6.60 (d, J=16 Hz, 1H); 7.26-7.43 (m, 10H).

Example 25M tert-Butyl 2(S)-(methoxycarbonylethyl)-2-[3(S)-(4(S)-phenyloxazolidin-2-on-3-yl)-4(R)-(2-styryl)azetidin-2-on-1-yl]acetate. The imine prepared from 428 mg (1.97 mmol) of L-glutamic acid γ-t-butyl ester α-methyl ester and cinnamaldehyde was combined with 2-(4(S)-phenyloxazolidin-2-on-3-yl) acetyl chloride (Example 1) to give 864 mg (82%) of Example 25M after flash column chromatography purification (70:30 hexanes/ethyl acetate); $^1$H NMR (CDCl$_3$) δ 1.40 (s, 9H); 2.12-2.27 (m, 1H); 2.32-2.55 (m, 3H); 3.50 (s, 3H); 3.72 (dd, J=4.6 Hz, J=10.4 Hz, 1H); 4.12-4.17 (m, 1H); 4.34 (dd, J=5 Hz, J=9 Hz, 1H); 4.50 (d, J=5 Hz, 1H); 4.60 (t, J=8.9 Hz, 1H); 4.81-4.86 (m, 1H); 6.06 (dd, J=9 Hz, J=16 Hz, 1H); 6.59 (d, J=16 Hz, 1H); 7.25-7.42 (m, 10H).

Example 25P

Methyl 2(S)-(tert-Butoxycarbonylmethyl)-2-[3(S)-(4(S)-phenyloxazolidin-2-on-3-yl)-4(R)-(2-styryl)azetidin-2-on-1-yl]acetate. The imine prepared from 424 mg (2.09 mmol) of L-aspartic acid γ-t-butyl ester α-methyl ester and cinnamaldehyde was combined with 2-(4(S)-phenyloxazolidin-2-on-3-yl) acetyl chloride (Example 1) to give 923 mg (85%) of Example 25P after after recrystallization from CH$_2$Cl$_2$/hexanes; $^1$H NMR (CDCl$_3$) δ 1.41 (s, 9H); 2.77 (dd, J=7.5 Hz, J=16.5 Hz, 1H); 3.00 (dd, J=7 Hz, J=16.5 Hz, 1H); 4.16 (dd, J=7.5 Hz, J=9 Hz, 1H); 4.41-48 (m, 2H); 4.55 (d, J=5 Hz, 1H); 4.60 (t, J=8.8 Hz, 1H); 4.86 (dd, J=7.5 Hz, J=9 Hz, 1H); 5.93 (dd, J=9.5 Hz, J=15.5 Hz, 1H); 6.61 (d, J=15.5 Hz, 1H); 7.25-7.43 (m, 10H).

Example 25L

2(R)-(tert-Butoxycarbonylmethyl)-2-[3(S)-(4(S)-phenyloxazolidin-2-on-3-yl)-4(R)-(2-styryl)azetidin-2-on-1-yl]

acetic acid N—[(R)-1-(3-trifluoromethylpheny)ethyl]amide. The imine prepared from 160 mg (0.44 mmol) of D-aspartic acid β-t-butyl ester α-[(R)-1-(3-trifluoromethylpheny)ethyl] amide and cinnamaldehyde was combined with 2-(4(S)-phenyloxazolidin-2-on-3-yl) acetyl chloride (Example 1) to give 166 mg (55%) of Example 25L after flash column chromatography purification (70:30 hexanes/EtOAc). Example 25L exhibited an $^1$H NMR spectrum consistent with the assigned structure.

Example 25N

2(R)-(tert-Butoxycarbonylmethyl)-2-[3(S)-(4(S)-phenyloxazolidin-2-on-3-yl)-4(R)-(2-styryl)azetidin-2-on-1-yl] acetic acid N—[(S)-1-(3-trifluoromethylpheny)ethyl]amide. The imine prepared from 120 mg (0.22 mmol) of D-aspartic acid 3-t-butyl ester α-[(S)-1-(3-trifluoromethylpheny)ethyl] amide and cinnamaldehyde was combined with 2-(4(S)-phenyloxazolidin-2-on-3-yl) acetyl chloride (Example 1) to give 75 mg (50%) of Example 25N after flash column chromatography purification (70:30 hexanes/EtOAc). Example 25N exhibited an $^1$H NMR spectrum consistent with the assigned structure.

Example 25Q

Methyl 2(R)-(2-(3-trifluoromethylbenzyl)aminocarbonyl)ethyl)-2-[3(S)-(4(S)-phenyloxazolidin-2-on-3-yl)-4(R)-(2-styryl)azetidin-2-on-1-yl]acetate. The imine prepared from 517 mg (1.62 mmol) of D-glutamic acid α-methyl ester γ-(3-trifluoromethyl)benzylamide and cinnamaldehyde was combined with 2-(4(S)-phenyloxazolidin-2-on-3-yl) acetyl chloride (Example 1) to give 527 mg (51%) of Example 25Q after flash column chromatography purification (50:50 hexanes/EtOAc). Example 25Q exhibited an $^1$H NMR spectrum consistent with the assigned structure.

The following compounds were prepared according to the processes described herein:

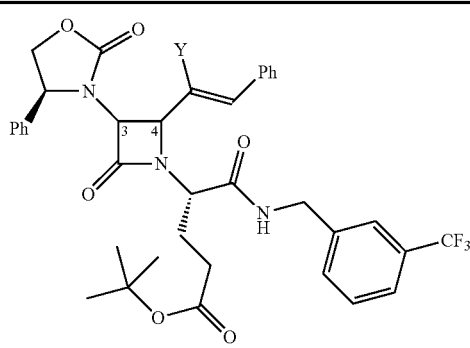

| Example | Y | C(3)-C(4) Stereochemistry |
|---|---|---|
| 25R | F | (3S,4R) |
| 25S | F | not determined |
| 25T | Br | not determined |
| 25U | Br | not determined |

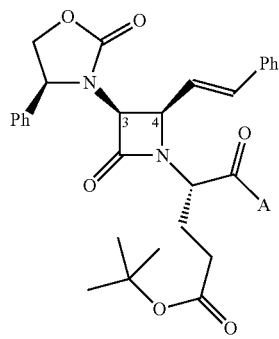

| Example | A |
|---|---|
| 25V | (R)-1,2,3,4-tetrahydro-1-naphtylamide |
| 25W | 1-phenyl-cyclopentylamide |

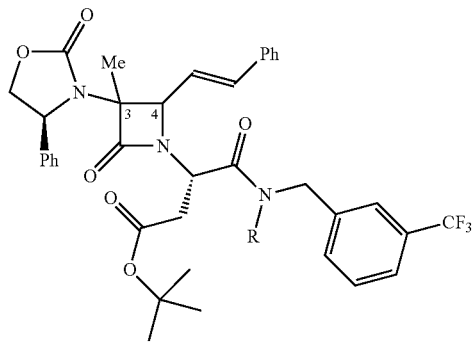

| Example | C(3)-C(4) Stereochemistry | R |
|---|---|---|
| 25X | (3S)-cis | Me |
| 25Y | not determined | H |

| Example | A |
|---|---|
| 25Z | 1-phenyl-cyclopent-1-ylamino |
| 25AA | (R)-1-phenylethy-1-amino |

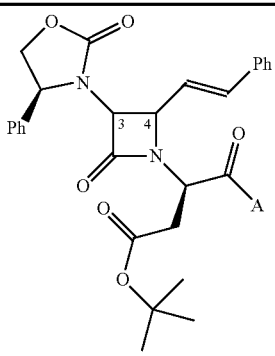

| Example | C(3)-C(4) Stereo-chemistry | A | A' |
|---|---|---|---|
| 25AB | (3S,4R) | α,α-dimethylbenzylamino | t-butyl ester |
| 25AC | not determined | N-methyl-3-CF3-benzylamino | t-butyl ester |
| 25AD | not determined | (R)-α-methylbenzylamino | t-butyl ester |
| 25AE | (3S,4R) | (R)-α,N-dimethylbenzylamino | t-butyl ester |

Example 25AF t-Butyl 2(S)-(2-(3-trifluoromethylbenzyl)aminocarbonyl)ethyl)-2-[3(S)-(4(S)-phenyloxazolidin-2-on-3-yl)-4(R)-(2-styryl)azetidin-2-on-1-yl]acetate.

Example 26

General procedure for hydrolysis of a tert-butyl ester. A solution of tert-butyl ester derivative in formic acid, typically 1 g in 10 mL, is stirred at ambient temperature until no more ester is detected by thin layer chromatography (dichloromethane 95%/methanol 5%), a typical reaction time being around 3 hours. The formic acid is evaporated under reduced pressure; the resulting solid residue is partitioned between dichloromethane and saturated aqueous sodium bicarbonate. The organic layer is evaporated to give an off-white solid that may be used directly for further reactions, or recrystallized from an appropriate solvent system if desired.

Examples 27-34AE were prepared from the appropriate tert-butyl ester according to the procedure used in Example 26.

Example 27

2(R,S)-(Carboxy)-2-[3(S)-(4(S)-phenyloxazolidin-2-on-3-yl)-4(R)-(2-styryl)azetidin-2-on-1-yl]acetic acid N-(3-trifluoromethylbenzyl)amide. Example 18 (0.30 g, 0.46 mmol) was hydrolyzed to give 0.27 g (quantitative yield) of Example 27 as an off-white solid; $^1$H NMR (CDCl$_3$) δ 4.17-5.28 (m, 9H); 6.21-6.29 (m, 1H), 6.68-6.82 (m, 1H); 7.05-7.75 (m, 13H); 9.12-9.18 (m, 1H).

Example 28

2(S)-(Carboxymethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide. Example 19 (1.72 g, 2.59 mmol) was hydrolyzed to give 1.57 g (quantitative yield) of Example 28 as an off-white solid; $^1$H NMR (CDCl$_3$) δ 2.61 (dd, J=9.3 Hz, J=16.6 Hz, 1H); 3.09-3.14 (m, 1H); 4.10-4.13 (m, 1H); 4.30 (d, J=4.5 Hz, 1H); 4.39-4.85 (m, 6H); 6.20 (dd, J=9.6 Hz, J=15.7 Hz, 1H); 6.69 (d, J=15.8 Hz, 1H); 7.12-7.15 (m, 2H); 7.26-7.50 (m, 11H); 7.61 (s, 1H); 8.41-8.45 (m, 1H).

Example 28A

2(S)-(Carboxymethyl)-2-[3(R)-(4(R)-phenyloxazolidin-2-on-3-yl)-4(S)-(2-styryl)azetidin-2-on-1-yl]acetic acid N-(3-trifluoromethylbenzyl)amide. Example 19A (41 mg, 0.06 mmol) was hydrolyzed to give 38 mg (quantitative yield) of Example 28A as an off-white solid; $^1$H NMR (CDCl$_3$) δ 2.26 (d, J=7 Hz, 1H); 4.03 (t, J=7 Hz, 1H); 4.16 (t, J=8 Hz, 1H); 4.26 (d, J=4.3 Hz, 1H); 4.46 (dd, J=5.7 Hz, J=15.1, 1H); 4.53-4.75 (m, 5H); 6.25 (dd, J=9.5 Hz, J=15.7 Hz, 1H); 6.77 (d, J=15.7 Hz, 1H); 7.28-7.53 (m, 13H); 7.64 (s, 1H); 8.65-8.69 (m, 1H).

Example 29

2(S)-(Carboxyethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide. Example 20 (4.97 g, 7.34 mmol) was hydrolyzed to give 4.43 g (97%) of Example 29 as an off-white solid; $^1$H NMR (CDCl$_3$) δ 1.92-2.03 (m, 1H); 2.37-2.51 (m, 3H); 4.13-4.19 (m, 1H); 3.32 (d, J=4.9 Hz, 1H); 4.35-4.39 (m, 1H); 4.44 (dd, J=5.9 Hz, J=14.9 Hz, 1H); 4.50-4.57 (m, 2H); 4.61-4.67 (m, 1H); 4.70-4.76 (m, 1H); 6.24 (dd, J=9.6 Hz, J=15.8 Hz, 1H); 6.70 (d, J=15.8 Hz, 1H); 7.18-7.47 (m, 14H).

Example 30

2(S)-(Carboxymethyl)-2-[3(S)-(4(S)-phenyloxazolidin-2-on-3-yl)-4(R)-(2-styryl)azetidin-2-on-1-yl]acetic acid N-[4-(2-phenylethyl)]piperazinamide. Example 21 (1.88 g, 2.78 mmol) was hydrolyzed to give 1.02 g (60%) of Example 30 as an off-white solid; $^1$H NMR (CDCl$_3$) δ 2.63 (dd, J=6.0 Hz, J=16.5 Hz, 1H); 2.75-2.85 (m, 1H); 3.00 (dd, J=8.2 Hz, J=16.6 Hz, 1H); 3.13-3.26 (m, 4H); 3.37-3.56 (m, 4H); 3.86-4.00 (m, 1H); 4.05-4.11 (m, 1H); 4.24 (d, J=5.0 Hz, 1H); 4.46-4.66 (m, 1H); 4.65-4.70 (m, 1H); 5.10-5.15 (m, 1H); 6.14 (dd, J=9.3 Hz, J=15.9 Hz, 1H); 6.71 (d, J=15.9 Hz, 1H); 7.22-7.41 (m, 15H); 12.02 (s, 1H).

Example 31

2(S)-(Carboxyethyl)-2-[3(S)-(4(S)-phenyloxazolidin-2-on-3-yl)-4(R)-(2-styryl)azetidin-2-on-1-yl]acetic acid N-[4-(2-phenylethyl)]piperazinamide. Example 22 (0.383 g, 0.55 mmol) was hydrolyzed to give 0.352 g (quantitative yield) of Example 31 as an off-white solid; $^1$H NMR (CDCl$_3$) δ 1.93-2.01 (m, 1H); 2.07-2.36 (m, 6H); 2.82-2.90 (m, 1H); 3.00-3.20 (m, 4H); 3.36-3.54 (m, 4H); 3.74-3.82 (m, 1H); 4.06-4.11 (m, 1H); 4.29 (d, J=4.9 Hz, 1H); 4.33-4.46 (m, 2H); 4.50-4.58 (m, 2H); 4.67-4.72 (m, 1H); 4.95-5.00 (m, 1H); 6.18 (dd, J=9.2 Hz, J=16.0 Hz, 1H); 6.67 (d, J=15.9 Hz, 1H); 7.19-7.42 (m, 15H); 8.80 (brs, 1H).

Example 32

2(R)-(Carboxymethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide. Example 23 (1.51 g, 2.27 mmol) was hydrolyzed to give 1.38 g (quantitative yield) of Example 32 as an off-white solid.

Example 32A

2(R)-(Carboxymethyl)-2-[3(R)-(4(R)-phenyloxazolidin-2-on-3-yl)-4(S)-(2-styryl)azetidin-2-on-1-yl]acetic acid N-(3-trifluoromethylbenzyl)amide. Example 23A (550 mg, 0.83 mmol) was hydrolyzed to give 479 mg (95%) of Example 32A as an off-white solid. Example 32A exhibited an $^1$H NMR spectrum consistent with the assigned structure.

Example 33

2(R)-(Carboxyethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide. Example 24 (0.604 g, 0.89 mmol) was hydrolyzed to give 0.554 g (quantitative yield) of Example 33 as an off-white solid.

Example 34

2(S)-(Carboxyethyl)-2-[3(S)-(4(S)-phenyloxazolidin-2-on-3-yl)-4(R)-(2-styryl)azetidin-2-on-1-yl]acetic acid N-(4-cyclohexyl)piperazinamide. Example 25 (0.537 g, 0.80 mmol) was hydrolyzed to give 0.492 g (quantitative yield) of Example 34 as an off-white solid; $^1$H NMR (CDCl$_3$) δ 1.09-1.17 (m, 1H); 1.22-1.33 (m, 2H); 1.40-1.47 (m, 2H); 1.63-1.67 (m, 1H); 1.85-1.90 (m, 2H); 1.95-2.00 (m, 1H); 2.05-2.15 (m, 3H); 2.20-2.24 (m, 1H); 2.30-2.36 (m, 1H); 2.85-2.93 (m, 1H); 3.25-3.33 (m, 1H); 3.36-3.46 (m, 2H); 3.81-3.87 (m, 1H); 4.08 (t, J=8.3 Hz, 1H); 4.28 (d, J=5.0 Hz, 1H); 4.33-4.56 (m, 4H); 4.70 (t, J=8.3 Hz, 1H); 4.83-4.91 (m, 1H); 6.17 (dd, J=9.1 Hz, J=15.9 Hz, 1H); 6.67 (d, J=15.9 Hz, 1H); 7.25-7.44 (m, 10H); 8.22 (brs, 1H).

Example 34A

2(S)-(2-(4-Cyclohexylpiperazinylcarbonyl)ethyl)-2-[3(S)-(4(S)-phenyloxazolidin-2-on-3-yl)-4(R)-(2-styryl)azetidin-2-on-1-yl]acetic acid. Example 25A (0.787 g, 1.28 mmol) was hydrolyzed to give 0.665 g (92%) of Example 34A as an off-white solid; $^1$H NMR (CDCl$_3$) δ 1.05-1.13 (m, 1H); 1.20-1.40 (m, 5H); 1.60-1.64 (m, 1H); 1.79-1.83 (m, 2H); 2.00-2.05 (m, 2H); 2.22-2.44 (m, 3H); 2.67-2.71 (m, 1H); 2.93-3.01 (m, 4H); 3.14-3.18 (m, 1H); 3.38-3.42 (m, 1H); 3.48-3.52 (m, 1H); 3.64-3.69 (m, 1H); 4.06-4.14 (m, 2H); 4.34-4.43 (m, 2H); 4.56 (t, J=8.8 Hz, 1H); 4.73 (t, J=8.4 Hz, 1H); 6.15 (dd, J=9.1 Hz, J=16.0 Hz, 1H); 6.65 (d, J=16.0 Hz, 1H); 7.25-7.42 (m, 10H).

Example 34B

2(R)-(Carboxymethyl)-2-[3(S)-(4(S)-phenyloxazolidin-2-on-3-yl)-4(R)-(2-styryl)azetidin-2-on-1-yl]acetic acid N-(2-fluoro-3-trifluoromethylbenzyl)carboxamide. Example 25B (0.26 g, 0.38 mmol) was hydrolyzed to give 0.238 g (quantitative yield) of Example 34B as an off-white solid; $^1$H NMR (CDCl$_3$) δ 3.27 (d, J=7.2 Hz, 1H); 4.06 (t, J=7.2 Hz, 1H); 4.15 (t, J=8.1 Hz, 1H); 4.27 (d, J=4.8 Hz, 1H); 4.56-4.76 (m, 5H); 6.34 (dd, J=9.5 Hz, J=15.7 Hz, 1H); 6.80 (d, J=15.7 Hz, 1H); 7.06 (t, J=7.7 Hz, 1H); 7.31-7.54 (m, 12H); 8.58 (t, J=5.9 Hz, 1H).

Example 34C

2(R)-(Carboxymethyl)-2-[3(S)-(4(S)-phenyloxazolidin-2-on-3-yl)-4(R)-(2-styryl)azetidin-2-on-1-yl]acetic acid N—[(S)-α-methylbenzyl]amide. Example 25C (0.215 g, 0.35 mmol) was hydrolyzed to give 0.195 g (quantitative yield) of Example 34C as an off-white solid; $^1$H NMR (CDCl$_3$) δ 1.56 (d, J=7.0 Hz, 1H); 3.10 (dd, J=4.5 Hz, J=17.9 Hz, 1H); 3.18 (dd, J=9.8 Hz, J=17.9 Hz, 1H); 4.00 (dd, J=4.5 Hz, J=9.7 Hz, 1H); 4.14 (t, J=8.2 Hz, 1H); 4.26 (d, J=4.7 Hz, 1H); 5.02-5.09 (m, 1H); 6.41 (dd, J=9.4 Hz, J=15.8 Hz, 1H); 6.78 (d, J=15.8 Hz, 1H); 7.18 (t, J=7.3 Hz, 1H); 7.26-7.43 (m, 12H); 8.29 (d, J=8.2 Hz, 1H).

Example 34D

2(R)-(Carboxymethyl)-2-[3(S)-(4(S)-phenyloxazolidin-2-on-3-yl)-4(R)-(2-styryl)azetidin-2-on-1-yl]acetic acid N—[(R)-α-methylbenzyl]amide. Example 25D (0.22 g, 0.35 mmol) was hydrolyzed to give 0.20 g (quantitative yield) of Example 34D as an off-white solid; $^1$H NMR (CDCl$_3$) δ 1.59 (d, J=7.0 Hz, 1H); 3.25 (d, J=7.0 Hz, 2H); 3.92 (t, J=7.3 Hz, 1H); 4.15 (t, J=8.3 Hz, 1H); 4.26 (d, J=5.0 Hz, 1H); 4.52 (dd, J=4.8 Hz, J=9.3 Hz, 1H); 4.65 (t, J=8.8 Hz, 1H); 4.72 (t, J=8.3 Hz, 1H); 5.07-5.28 (m, 1H); 6.29 (dd, J=9.5 Hz, J=15.6 Hz, 1H); 6.71 (d, J=16.0 Hz, 1H); 7.20-7.43 (m, 13H); 8.31 (d, J=8.0 Hz, 1H).

Example 34E

2(R)-(Carboxymethyl)-2-[3(S)-(4(S)-phenyloxazolidin-2-on-3-yl)-4(R)-(2-styryl)azetidin-2-on-1-yl]acetic acid N-methyl-N-(3-trifluoromethylbenzyl)amide. Example 25E (0.253 g, 0.37 mmol) was hydrolyzed to give 0.232 g (quantitative yield) of Example 34E as an off-white solid; $^1$H NMR (CDCl$_3$) δ 3.07-3.15 (m, 4H); 4.13 (t, J=8.2 Hz, 1H); 4.30 (d, J=4.9 Hz, 1H); 4.46-4.78 (m, 5H); 5.23 (dd, J=4.6 Hz, J=9.7 Hz, 1H); 6.20 (dd, J=9.4 Hz, J=15.9 Hz, 1H); 6.73 (d, J=15.9 Hz, 1H); 7.25-7.43 (m, 15H).

Example 34F

2(S)-(Carboxyethyl)-2-[3(S)-(4(S)-phenyloxazolidin-2-on-3-yl)-4(R)-(2-chlorostyr-2-yl)azetidin-2-on-1-yl]acetic acid N-(3-trifluoromethylbenzyl)amide. Example 25F (0.707 g, 0.99 mmol) was hydrolyzed to give 0.648 g (99%) of Example 34F as an off-white solid; $^1$H NMR (CDCl$_3$) δ 2.22-2.28 (m, 2H); 2.49-2.64 (m, 2H); 4.09 (t, J=8.0 Hz, 1H); 4.25-4.62 (m, 6H); 4.87 (t, J=8.0 Hz, 1H); 6.88 (s, 1H); 7.25-7.66 (m, 15H).

Example 34G

2(R)-(Carboxymethyl)-2-[3(S)-(4(S)-phenyloxazolidin-2-on-3-yl)-4(R)-(2'-methoxystyr-2-yl)azetidin-2-on-1-yl]acetic acid N-(3-trifluoromethylbenzyl)amide. Example 25G (0.268 g, 0.39 mmol) was hydrolyzed to give 0.242 g (98%) of Example 34G as an off-white solid; $^1$H NMR (CDCl$_3$) δ 3.26 (d, J=7.1 Hz, 1H); 3.79 (s, 3H); 4.14 (t, J=8.2 Hz, 1H); 4.25 (d, J=4.5 Hz, 1H); 4.51 (dd, J=5.9 Hz, J=15.5 Hz, 1H); 4.53-4.66 (m, 4H); 6.36 (dd, J=9.4 Hz, J=15.8 Hz, 1H); 8.88 (t, J=8.2 Hz, 1H); 6.70 (d, J=15.8 Hz, 1H); 7.18 (d, J=6.5 Hz, 1H); 7.25-7.48 (m, 10H); 7.48 (s, 1H); 8.66-8.69 (m, 1H).

Example 34H (2R)-(Benzyloxymethyl)-2-[3(S)-(4(S)-phenyloxazolidin-2-on-3-yl)-4(R)-(2-styryl)azetidin-2-on-1-yl]acetic acid. Example 25H (0.16 g, 0.28 mmol) was hydrolyzed to give 0.144 g (quantitative yield) of Example 34H as an off-white solid; $^1$H NMR (CDCl$_3$) δ 3.65 (dd, J=4.0 Hz, J=9.5 Hz, 1H); 3.82 (dd, J=5.5 Hz, J=9.5 Hz, 1H); 4.11 (dd, J=7.8 Hz, J=8.8 Hz, 1H); 4.33 (s, 2H); 4.50 (d, J=5.0 Hz, 1H); 4.57 (t, J=9.0 Hz, 1H); 4.67 (dd, J=4.0 Hz, J=5.0 Hz, 1H); 4.69 (dd, J=5.0 Hz, J=9.5 Hz, 1H); 4.75 (t, J=8.0 Hz, 1H); 6.17 (dd, J=9.3 Hz, J=15.8 Hz, 1H); 6.55 (d, J=16.0 Hz, 1H); 7.09-7.12 (m, 2H); 7.19-7.42 (m, 13H).

Example 34I

2(S)-(2-(4-Cyclohexylpiperazinylcarbonyl)methyl)-2-[3 (S)-(4(S)-phenyloxazolidin-2-on-3-yl)-4(R)-(2-styryl)azetidin-2-on-1-yl]acetic acid. Example 25I (737 mg, 1.12 mmol) was hydrolyzed to give 640 mg (95%) of Example 34I as an off-white solid. Example 34I exhibited an $^1$H NMR spectrum consistent with the assigned structure.

Example 34J

3(R)-[3(S)-(4(S)-Phenyloxazolidin-2-on-3-yl)-3-methyl-4(R)-(styr-2-yl)azetidin-2-on-1-yl]-3-[(3-trifluoromethyl) phenylmethylaminocarbonyl]propanoic acid. Using the general method of Example 26, 120 mg (0.18 mmol) of Example 25J was hydrolyzed to give 108 mg (98%) of Example 34J as an off-white solid; $^1$H NMR (CDCl$_3$) δ 1.22 (s, 3H); 3.25 (dd, J=3.5 Hz, J=18.0 Hz, 1H); 3.36 (dd, J=10.8 Hz, J=18.2 Hz, 1H); 4.01 (dd, J=4.0 Hz, J=10.5 Hz, 1H); 4.05 (dd, J=3.8 Hz, J=8.8 Hz, 1H); 4.33 (d, J=9.0 Hz, 1H); 4.44-4.51 (m, 3H); 4.61-4.66 (m, 1H); 4.73 (dd, J=3.8 Hz, J=8.8 Hz, 1H); 6.19 (dd, J=9.0 Hz, J=16.0 Hz, 1H); 6.74 (d, J=16.0 Hz, 1H); 7.22-7.54 (m, 13H); 7.65 (s, 1H).

Example 34K

2(R)-(Carboxymethyl)-2-[3(S)-(4(S)-phenyloxazolidin-2-on-3-yl)-4(R)-(propen-1-yl)azetidin-2-on-1-yl]acetic acid N-(3-trifluoromethylbenzyl)amide. Using the general method of Example 26, 160 mg (0.27 mmol) of Example 25K was hydrolyzed to give 131 mg (90%) of Example 34K as an off-white solid. $^1$H NMR (CDCl$_3$) δ 1.69 (dd, J=1 Hz, J=6.5 Hz, 3H); 3.23 (d, J=7 Hz, 1H); 3.93 (t, J=7.3 Hz, 1H); 4.14-4.20 (m, 3H); 4.29 (dd, J=5 Hz, J=9.5 Hz, 1H); 4.43 (dd, J=6 Hz, J=15 Hz, 1H); 4.61 (dd, J=6.5 Hz, J=15 Hz, 1H); 4.66-4.74 (m, 2H); 5.50-5.55 (m, 1H); 5.90-5.98 (m, 1H); 7.32-7.60 (m, 9H); 8.60-8.64 (m, 1H).

Example 34L

2(R)-(Carboxylmethyl)-2-[3(S)-(4(S)-phenyloxazolidin-2-on-3-yl)-4(R)-(2-styryl)azetidin-2-on-1-yl]acetic acid N—[(R)-1-(3-trifluoromethylpheny)ethyl]amide. Example 25L (166 mg, 0.24 mmol) was hydrolyzed to give 152 mg (quantitative yield) of Example 34L as an off-white solid; and exhibited an $^1$H NMR spectrum consistent with the assigned structure.

Example 34M

2(S)-(Methoxycarbonylethyl)-2-[3(S)-(4(S)-phenyloxazolidin-2-on-3-yl)-4(R)-(2-styryl)azetidin-2-on-1-yl]acetic acid. Example 25M (875 mg, 1.64 mmol) was hydrolyzed to give 757 mg (97%) of Example 34M as an off-white solid, and exhibited an $^1$H NMR spectrum consistent with the assigned structure.

Example 34N

2(R)-(Carboxylmethyl)-2-[3(S)-(4(S)-phenyloxazolidin-2-on-3-yl)-4(R)-(2-styryl)azetidin-2-on-1-yl]acetic acid N—[(S)-1-(3-trifluoromethylpheny)ethyl]amide. Example 25N (38.5 mg, 0.057 mmol) was hydrolyzed to give 35 mg (quantitative yield) of Example 34N as an off-white solid, and exhibited an $^1$H NMR spectrum consistent with the assigned structure.

Example 34O

2(S)-(tert-Butoxycarbonylethyl)-2-[3(S)-(4(S)-phenyloxazolidin-2-on-3-yl)-4(R)-(2-styryl)azetidin-2-on-1-yl] acetic acid. Example 25O (97 mg, 0.18 mmol) was dissolved in methanol/tetrahydrofuran (2.5 mL/2 mL) and reacted with lithium hydroxide (0.85 mL of a 0.85M solution in water; 0.72 mmol) for 6 hours at room temperature. The reaction was diluted with 15 mL dichloromethane and aqueous hydrochloric acid (1M) was added until the pH of the aqueous layer reached 5 (as measured by standard pH paper). The organic layer was then separated and evaporated to dryness to give 84 mg (89%) of Example 34O as an off-white solid, and exhibited an $^1$H NMR spectrum consistent with the assigned structure.

Example 34P

2(S)-(tert-Butoxycarbonylethyl)-2-[3(S)-(4(S)-phenyloxazolidin-2-on-3-yl)-4(R)-(2-styryl)azetidin-2-on-1-yl] acetic acid. Example 25P (200 mg, 0.39 mmol) was hydrolyzed according to the method used for Example 34O to give 155 mg (88%) of Example 34P as an off-white solid; and exhibited an $^1$H NMR spectrum consistent with the assigned structure.

Example 34Q

2(R)-(2-(3-trifluoromethylbenzyl)amino-1-ylcarbonyl) ethyl)-2-[3(S)-(4(S)-phenyloxazolidin-2-on-3-yl)-4(R)-(2-styryl)azetidin-2-on-1-yl]acetic acid. Example 25Q (150 mg, 0.24 mmol) was hydrolyzed according to the method used for Example 34O to give 143 mg (97%) of Example 34Q as an off-white solid, and exhibited an $^1$H NMR spectrum consistent with the assigned structure.

Example 34R

2(R)-(tert-Butoxycarbonylmethyl)-2-[3(RS)-2-thienylmethyl)-4(R)-(2-styryl)azetidin-2-on-1-yl]acetic acid N-(3-trifluoromethylbenzyl)amide. The imine prepared from 290 mg (0.84 mmol) of D-aspartic acid β-t-butyl ester t-(3-trifluoromethyl)benzylamide and cinnamaldehyde was combined with 2-thiophene-acetyl chloride to give 42 mg (8%) of Example 34R after flash column chromatography purification (70:30 hexanes/ethyl acetate), and exhibited an $^1$H NMR spectrum consistent with the assigned structure.

The following compounds were prepared according to the processes described herein:

| Example | Y | C(3)-C(4) Stereochemistry |
|---|---|---|
| 34S | F | (3S,4R) |
| 34T | F | not determined |
| 34U | Br | not determined |

| Example | A |
|---|---|
| 34V | (R)-1,2,3,4-tetrahydro-1-naphtylamide |
| 34W | 1-phenyl-cyclopentylamide |

| Example | C(3)-C(4) Stereochemistry | R |
|---|---|---|
| 34X | (3S,4R) | Me |
| 34Y | not determined | H |

| Example | A |
|---|---|
| 34Z | 1-phenyl-cyclopent-1-ylamino |
| 34AA | (R)-1-phenylethy-1-amino |

| Example | C(3)-C(4) Stereochemistry | A |
|---|---|---|
| 34AB | (3S,4R) | α,α-dimethylbenzylamino |
| 34AC | not determined | N-methyl-3-CF3-benzylamino |
| 34AD | not determined | (R)-α-methylbenzylamino |
| 34AE | (3S,4R) | (R)-α,N-dimethylbenzylamino |

Examples 36-42A, shown in the following table, were prepared using the procedure of Example 6, except that N-benzyloxycarbonyl-D-aspartic acid β-t-butyl ester monohydrate was replaced with Example 27, and 3-(trifluoromethyl)benzyl amine was replaced with the appropriate amine; all listed Examples exhibited an $^1$H NMR spectrum consistent with the assigned structure.

| Example | A' |
|---|---|
| 36 | 2-(piperidinyl)ethylamino |
| 37 | 4-(piperidinyl)piperidinyl |
| 38 | 4-(2-phenylethyl)piperazinyl |
| 39 | 1-benzylpiperidin-4-ylamino |
| 40 | 4-butylpiperazinyl |

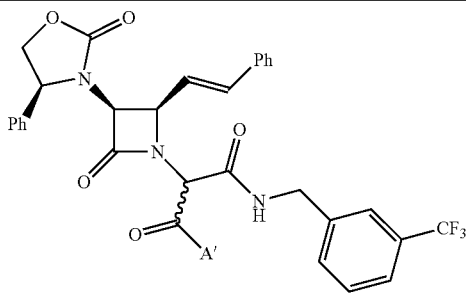

| Example | A' |
|---|---|
| 41 | 4-isopropylpiperazinyl |
| 42 | 4-cyclohexylpiperazinyl |
| 42A | 4-[2-(piperidinyl)ethyl]piperidinyl |

Examples 43-86A, shown in the following table, were prepared using the procedure of Example 6, except that N-benzyloxycarbonyl-D-aspartic acid β-t-butyl ester monohydrate was replaced with Example 28, and 3-(trifluoromethyl)benzyl amine was replaced with the appropriate amine; all listed Examples exhibited an $^1$H NMR spectrum consistent with the assigned structure.

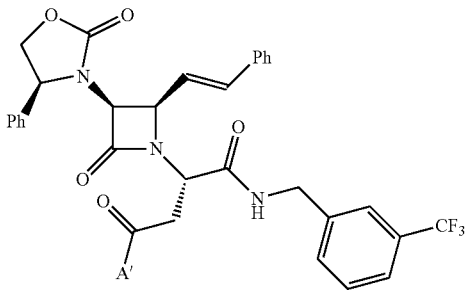

| Example | A' |
|---|---|
| 43 | 2-(piperidinyl)ethylamino |
| 44 | 4-(piperidinyl)piperidinyl |
| 45 | 4-(phenylethyl)piperazinyl |
| 46 | fur-2-ylmethylamino |
| 47 | 4-(pyrrolidinyl)piperazinyl |
| 48 | 4-(3-trifluoromethylphenyl)piperazinyl |
| 49 | 4-(benzyloxycarbonyl)piperazinyl |
| 50 | 4-[2-(2-hydroxyethoxy)ethyl]piperazinyl |
| 51 | 4-benzylpiperazinyl |
| 52 | 4-(3,4-methylenedioxybenzyl)piperazinyl |
| 53 | 4-phenylpiperazinyl |
| 54 | 4-(3-phenylprop-2-enyl)piperazinyl |
| 55 | 4-ethylpiperazinyl |
| 56 | 2-(dimethylamino)ethylamino |
| 57 | 4-(pyrrolidinylcarbonylmethyl)piperazinyl |
| 58 | 4-(1-methylpiperidin-4-yl)piperazinyl |
| 59 | 4-butylpiperazinyl |
| 60 | 4-isopropylpiperazinyl |
| 61 | 4-pyridylmethylamino |
| 62 | 3-(dimethylamino)propylamino |
| 63 | 1-benzylpiperidin-4-ylamino |
| 64 | N-benzyl-2-(dimethylamino)ethylamino |
| 65 | 3-pyridylmethylamino |
| 66 | 4-(cyclohexyl)piperazinyl |
| 67 | 4-(2-cyclohexylethyl)piperazinyl |
| 68 | 4-[2-(morpholin-4-yl)ethyl]piperazinyl |
| 69 | 4-(4-tert-butylbenzyl)piperazinyl |
| 70 | 4-[2-(piperidinyl)ethyl]piperazinyl |
| 71 | 4-[3-(piperidinyl)propyl]piperazinyl |
| 72 | 4-[2-(N,N-dipropylamino)ethyl]piperazinyl |
| 73 | 4-[3-(N,N-diethylamino)propyl]piperazinyl |

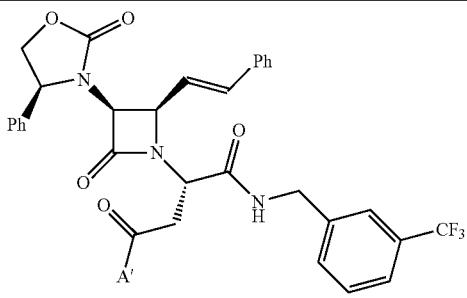

| Example | A' |
|---|---|
| 74 | 4-[2-(dimethylamino)ethyl]piperazinyl |
| 75 | 4-[3-(pyrrolidinyl)propyl]piperazinyl |
| 76 | 4-(cyclohexylmethyl)piperazinyl |
| 77 | 4-cyclopentylpiperazinyl |
| 78 | 4-[2-(pyrrolidinyl)ethyl]piperazinyl |
| 79 | 4-[2-(thien-2-yl)ethyl]piperazinyl |
| 80 | 4-(3-phenylpropyl)piperazinyl |
| 81 | 4-[2-(N,N-diethylamino)ethyl]piperazinyl |
| 82 | 4-benzylhomopiperazinyl |
| 83 | 4-(bisphenylmethyl)piperazinyl |
| 84 | 3-(4-methylpiperazinyl)propylamino |
| 85 | (+)-3(S)-1-benzylpyrrolidin-3-ylamino |
| 86 | 2-pyridylmethylamino |
| 86A | 4-[2-(piperidinyl)ethyl]piperidinyl |
| 86B | 1-benzylpiperidin-4-ylamino N-oxide |

Example 86B

Example 63 (44 mg, 0.06 mmol) was dissolved in 4 mL dichloromethane and reacted with 3-chloroperoxybenzoic acid (12 mg, 0.07 mmol) until the reaction was complete as assessed by TLC (dichloromethane 94%/methanol 6%, UV detection). The reaction was quenched with aqueous sodium sulfite, the dichloromethane layer was washed with 5% aqueous sodium bicarbonate and distilled water. Evaporation of the dichloromethane layer afforded Example 86B as an off-white solid (35 mg, 78%), and exhibited an $^1$H NMR spectrum consistent with the assigned structure.

Examples 121-132, shown in The following table, were prepared using the procedure of Example 6, except that N-benzyloxycarbonyl-D-aspartic acid β-t-butyl ester monohydrate was replaced with Example 30, and 3-(trifluoromethyl)benzyl amine was replaced with the appropriate amine; all listed Examples exhibited an $^1$H NMR spectrum consistent with the assigned structure.

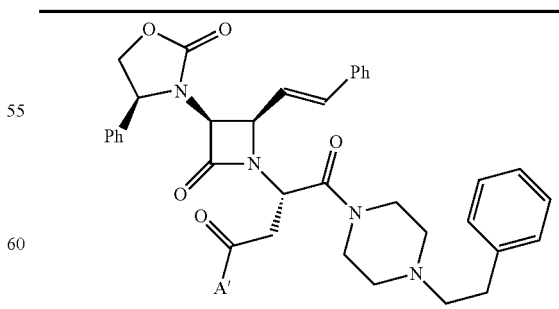

| Example | A' |
|---|---|
| 121 | 3-trifluoromethylbenzylamino |
| 122 | morpholin-4-ylamino |

71

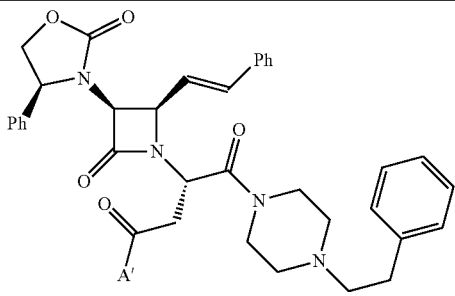

| Example | A' |
|---|---|
| 123 | 2-(dimethylamino)ethylamino |
| 124 | 3-(dimethylamino)propylamino |
| 125 | cyclohexylamino |
| 126 | piperidinyl |
| 127 | 2-methoxyethylamino |
| 128 | isopropylamino |
| 129 | isobutylamino |
| 130 | ethylamino |
| 131 | dimethylamino |
| 132 | methylamino |

Examples 132A-132B, shown in the following table, were prepared using the procedure of Example 6, except that N-benzyloxycarbonyl-D-aspartic acid β-t-butyl ester monohydrate was replaced with Example 34I, and 3-(trifluoromethyl)benzyl amine was replaced with the appropriate amine; all listed Examples exhibited an $^1$H NMR spectrum consistent with the assigned structure.

| Example | A' |
|---|---|
| 132A | (2,3-dichlorobenzyl)amino |
| 132B | 1-phenylcyclohexylamino |

Example 132C

2(S)-(tert-Butoxycarbonylmethyl)-2-[3(S)-(4(S)-phenyloxazolidin-2-on-3-yl)-4(R)-(2-styryl)azetidin-2-on-1-yl] acetic acid N-(4-cyclohexyl)piperazinamide. Example 132C was prepared using the procedure of Example 6 except that N-benzyloxycarbonyl-D-aspartic acid β-t-butyl ester monohydrate was replaced with Example 34P, and 3-(trifluoromethyl)benzyl amine was replaced with 1-cyclohexyl-pipera-

72 zine. Example 132C exhibited an $^1$H NMR spectrum consistent with the assigned structure.

The compounds shown in the following table were prepared according to the processes described herein.

| Example | A | A' |
|---|---|---|
| 132D | 1-phenyl-cyclopent-1-ylamino | 4-(piperidinyl)piperidinyl |
| 132E | 1-phenyl-cyclopent-1-ylamino | 1-benzylpiperidin-4-ylamino |
| 132F | (R)-1-phenylethy-1-amino | 4-(piperidinyl)piperidinyl |

Examples 133-134G, shown in the following table, were prepared using the procedure of Example 6, except that N-benzyloxycarbonyl-D-aspartic acid β-t-butyl ester monohydrate was replaced with Example 32, and 3-(trifluoromethyl)benzyl amine was replaced with the appropriate amine; all listed Examples exhibited an $^1$H NMR spectrum consistent with the assigned structure.

| Example | A' |
|---|---|
| 133 | 4-(piperidinyl)piperidinyl |
| 134 | 4-(2-phenylethyl)piperazinyl |
| 134A | 4-[2-(piperidinyl)ethyl]piperidinyl |
| 134B | 4-(pyrrolidinyl)piperazinyl |
| 134C | 1-benzylpiperidin-4-ylamino |
| 134D | (pyridin-3-ylmethyl)amino |
| 134E | 3-(dimethylamino)propylamino |
| 134F | 3-(S)-(1-benzylpyrrolidin-3-yl)amino |
| 134G | 4-[(piperidinyl)methyl]piperidinyl |
| 134H | 4-(piperidinyl)piperidinyl N-oxide |

Example 134H

Example 134H was prepared using the procedure of Example 86B, except that Example 133 was replaced with Example 110. Example 134H was obtained as an off-white solid (48 mg, 94%), and exhibited an $^1$H NMR spectrum consistent with the assigned structure.

Example 134I

2(R)-[[4-(Piperidinyl)piperidinyl]carboxymethyl]-2-[3 (S)-(4(R)-phenyloxazolidin-2-on-3-yl)-4(R)-(2-styryl)azetidin-2-on-1-yl]acetic acid N-(3-trifluoromethylbenzyl) amide. Example 1341 was prepared using the procedure of Example 6, except that N-benzyloxycarbonyl-D-aspartic acid β-t-butyl ester monohydrate was replaced with Example 32A, and 3-(trifluoromethyl)benzyl amine was replaced with 4-(piperidinyl)piperidine, and exhibited an $^1$H NMR spectrum consistent with the assigned structure.

The compounds shown in the following table were prepared according to the processes described herein.

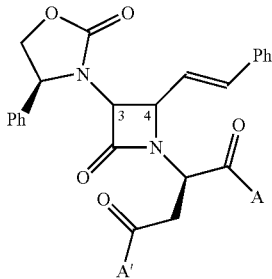

| Example | C(3)-C(4) Stereochemistry | A | A' |
|---|---|---|---|
| 134J | (3S,4R) | α,α-dimethylbenzylamino | 4-(piperidinyl)piperidinyl |
| 134K | (3S,4R) | α,α-dimethylbenzylamino | 1-benzylpiperidin-4-ylamino |
| 134L | not determined | N-methyl-3-CF3-benzylamino | 4-(piperidinyl)piperidinyl |
| 134M | (3S,4R) | N-methyl-3-CF3-benzylamino | 3-(pyrrolidinyl)piperidinyl |
| 134N | not determined | (R)-α-methylbenzylamino | 4-(piperidinyl)piperidinyl |
| 134O | (3S,4R) | (R)-α,N-dimethylbenzylamino | 4-(piperidinyl)piperidinyl |

Example 222

2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N-(2-fluoro-3-trifluoromethylbenzyl)carboxamide. Example 222 was prepared using the procedure of Example 6, except that N-benzyloxycarbonyl-D-aspartic acid β-t-butyl ester monohydrate was replaced with Example 34B, and 3-(trifluoromethyl)benzyl amine was replaced with 4-(piperidinyl)piperidine; Example 222 exhibited an $^1$H NMR spectrum consistent with the assigned structure.

Example 223

2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N—[(S)-α-methylbenzyl]amide. Example 223 was prepared using the procedure of Example 6, except that N-benzyloxycarbonyl-D-aspartic acid β-t-butyl ester monohydrate was replaced with Example 34C, and 3-(trifluoromethyl)benzyl amine was replaced with 4-(piperidinyl)piperidine; Example 223 exhibited an $^1$H NMR spectrum consistent with the assigned structure.

Example 224

2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N—[(R)-α-methylbenzyl]amide. Example 224 was prepared using the procedure of Example 6, except that N-benzyloxycarbonyl-D-aspartic acid β-t-butyl ester monohydrate was replaced with Example 34D, and 3-(trifluoromethyl)benzyl amine was replaced with 4-(piperidinyl)piperidine; Example 223 exhibited an $^1$H NMR spectrum consistent with the assigned structure.

Example 225

2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N-methyl-N-(3-trifluoromethylbenzyl)amide. Example 225 was prepared using the procedure of Example 6, except that N-benzyloxycarbonyl-D-aspartic acid β-t-butyl ester monohydrate was replaced with Example 34E, and 3-(trifluoromethyl)benzyl amine was replaced with 4-(piperidinyl)piperidine; Example 223 exhibited an $^1$H NMR spectrum consistent with the assigned structure; Calc'd for $C_{43}H_{48}F_3N_5O_5$: C, 66.91; H, 6.27; N, 9.07. found, C, 66.68; H, 6.25; N, 9.01.

Example 225 Hydrochloride Salt

Example 225 (212.5 mg) was dissolved in 30 mL dry $Et_2O$. Dry HCl gas was bubbled through this solution resulting in the rapid formation of an off-white precipitate. HCl addition was discontinued when no more precipitate was observed forming (ca. 5 minutes). The solid was isolated by suction filtration, washed twice with 15 mL of dry $Et_2O$ and dried to 213.5 mg (96% yield) of an off-white solid; Calc'd for $C_{43}H_{49}ClF_3N_5O_5$: C, 63.89; H, 6.11; N, 8.66; Cl, 4.39. found, C, 63.41; H, 5.85; N, 8.60; Cl, 4.86.

Example 225A

2(R)-[[4-[2-(piperidinyl)ethyl]piperidinyl]carbonylmethyl]-2-[3(S)-(4(S)-phenyloxazolidin-2-on-3-yl)-4(R)-(2-styryl)azetidin-2-on-1-yl]acetic acid N—[(S)-α-methylbenzyl]amide. Example 225A was prepared using the procedure of Example 6, except that N-benzyloxycarbonyl-D-aspartic acid β-t-butyl ester monohydrate was replaced with Example 34C, and 3-(trifluoromethyl)benzyl amine was replaced with 4-[2-(piperidinyl)ethyl]piperidine. Example 225A exhibited an $^1$H NMR spectrum consistent with the assigned structure.

Example 225B

2(R)-[[4-[2-(piperidinyl)ethyl]piperidinyl]carbonylmethyl]-2-[3(S)-(4(S)-phenyloxazolidin-2-on-3-yl)-4(R)-(2-styryl)azetidin-2-on-1-yl]acetic acid N—[(R)-α-methylbenzyl]amide. Example 225B was prepared using the procedure of Example 6, except that N-benzyloxycarbonyl-D-aspartic acid β-t-butyl ester monohydrate was replaced with Example 34D, and 3-(trifluoromethyl)benzyl amine was replaced with 4-[2-(piperidinyl)ethyl]piperidine. Example 225B exhibited an $^1$H NMR spectrum consistent with the assigned structure.

Example 225C

2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N—[(R)-1-(3-trifluoromethylpheny)ethyl]amide. Example 225C was prepared using the procedure of Example 6, except that N-benzyloxycarbonyl- D-aspartic acid β-t-butyl ester monohydrate was replaced with Example 34L, and 3-(trifluoromethyl)benzyl amine was replaced with 4-(piperidinyl)piperidine. Example 225C exhibited an ¹H NMR spectrum consistent with the assigned structure.

Example 225D

2(R)-[[4-(Piperidinyl)piperidinyl]carbonylmethyl]-2-[3 (S)-(4(S)-phenyloxazolidin-2-on-3-yl)-4(R)-(2-styryl)azetidin-2-on-1-yl]acetic acid N—[(S)-1-(3-trifluoromethylpheny)ethyl]amide. Example 225D was prepared using the procedure of Example 6, except that N-benzyloxycarbonyl-D-aspartic acid β-t-butyl ester monohydrate was replaced with Example 34N, and 3-(trifluoromethyl)benzyl amine was replaced with 4-(piperidinyl)piperidine. Example 225D exhibited an ¹H NMR spectrum consistent with the assigned structure.

Examples 87-120E, shown in the following table, were prepared using the procedure of Example 6, except that N-benzyloxycarbonyl-D-aspartic acid β-t-butyl ester monohydrate was replaced with Example 29, and 3-(trifluoromethyl)benzyl amine was replaced with the appropriate amine; all listed Examples exhibited an ¹H NMR spectrum consistent with the assigned structure.

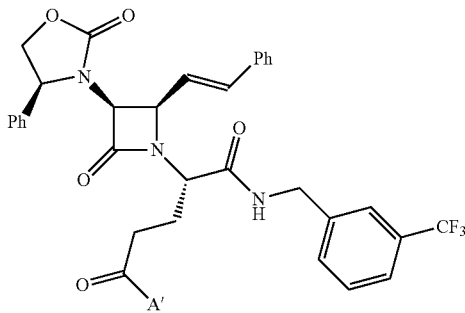

| Example | A' |
|---|---|
| 87 | 2-(piperidinyl)ethylamino |
| 88 | 4-(piperidinyl)piperidinyl |
| 89 | 2-(pyrid-2-yl)ethylamino |
| 90 | morpholin-4-ylamino |
| 91 | 4-(pyrrolidinyl)piperazinyl |
| 92 | 4-(3-trifluorophenyl)piperazinyl |
| 93 | 4-(benzyloxycarbonyl)piperazinyl |
| 94 | 4-[2-(2-hydroxylethoxy)ethyl]piperazinyl |
| 95 | 4-benzylpiperazinyl |
| 96 | 4-(3,4-methylenedioxybenzyl)piperazinyl |
| 97 | 4-phenylpiperazinyl |
| 98 | 4-(3-phenylprop-2-enyl)piperazinyl |
| 99 | 4-ethylpiperazinyl |
| 100 | 2-(dimethylamino)ethylamino |
| 101 | 4-(pyrrolidinylcarbonylmethyl)piperazinyl |
| 102 | 4-(1-methylpiperidin-4-yl)piperazinyl |
| 103 | 4-butylpiperazinyl |
| 104 | 4-isopropylpiperazinyl |
| 105 | 4-pyridylmethylamino |
| 106 | 3-(dimethylamino)propylamino |
| 107 | 1-benzylpiperidin-4-ylamino |
| 108 | N-benzyl-2-(dimethylamino)ethylamino |
| 109 | 3-pyridylmethylamino |
| 110 | 4-cyclohexylpiperazinyl |
| 111 | 4-(2-cyclohexylethyl)piperazinyl |
| 112 | 4-[2-(morpholin-4-yl)ethyl]piperazinyl |
| 113 | 4-(4-tert-butylbenzyl)piperazinyl |
| 114 | 4-[2-(piperidinyl)ethyl]piperazinyl |
| 115 | 4-[3-(piperidinyl)propyl]piperazinyl |
| 116 | 4-[2-(diisopropylamino)ethyl]piperazinyl |
| 117 | 4-[3-(diethylamino)propyl]piperazinyl |

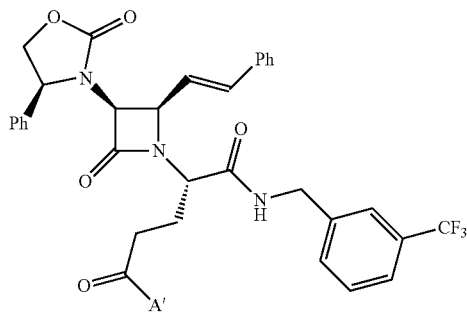

| Example | A' |
|---|---|
| 118 | 4-(2-dimethylaminoethyl)piperazinyl |
| 119 | 4-[3-(pyrrolidinyl)propyl]piperazinyl |
| 120 | 4-(cyclohexylmethyl)piperazinyl |
| 120A | 4-[2-(piperidinyl)ethyl]piperidinyl |
| 120B | 4-propyl-piperazinyl |
| 120C | 4-[N-(isopropyl)acetamid-2-yl]piperazinyl |
| 120D | 3-benzyl-hexahydro-(1H)-1,3-diazepinyl |
| 120E | 4-(piperidinylmethyl)piperidinyl |
| 120F | 4-cyclohexylpiperazinyl N-oxide |
| 120G | methoxy |
| 120H | 4-cyclohexylpiperazinyl |

Example 120F

Example 120F was prepared using the procedure of Example 86B, except that Example 63 was replaced with Example 110 to give an off-white solid (54.5 mg, 98%). Example 120F exhibited an ¹H NMR spectrum consistent with the assigned structure.

Example 120G

2(S)-(Methoxycarbonylethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide. Example 120G was prepared using the procedure of Example 6, except that N-benzyloxycarbonyl-D-aspartic acid β-t-butyl ester monohydrate was replaced with Example 34M, and exhibited an ¹H NMR spectrum consistent with the assigned structure.

Example 35

2(S)-[4-(2-phenylethyl)piperazinyl-carbonylethyl]-2-[3 (S)-(4(S)-phenyloxazolidin-2-on-3-yl)-4(R)-(2-styryl)azetidin-2-on-1-yl]acetic acid N-(3-trifluoromethylbenzyl) amide. Using the procedure of Example 6, except that N-benzyloxycarbonyl-D-aspartic acid β-t-butyl ester monohydrate was replaced with the carboxylic acid of Example 29 and 3-(trifluoromethyl)benzyl amine was replaced with 4-(2-phenylethyl)piperazine, the title compound was prepared; ¹H NMR (CDCl₃) δ 2.21-2.23 (m, 1H); 2.25-2.45 (m, 6H); 2.52-2.63 (m, 3H); 2.72-2.82 (m, 2H); 3.42-3.48 (m, 2H); 3.52-3.58 (m, 1H); 4.13-4.18 (m, 1H); 4.26 (dd, J=5.1 Hz, J=8.3 Hz, 1H); 4.29 (d, J=5.0 Hz, 1H); 4.44 (dd, J=6.0 Hz, J=15.0 Hz, 1H); 4.54 (dd, J=6.2 Hz, J=14.9 Hz, 1H); 4.61-4.68 (m, 2H); 4.70-4.75 (m, 1H); 6.27 (dd, J=9.6 Hz, J=15.8 Hz, 1H); 6.73 (d, J=15.8 Hz, 1H); 7.16-7.60 (m, 19H); 8.07-8.12 (m, 1H); FAB⁺ (M+H)⁺/z 794; Elemental Analysis calculated for $C_{45}H_{46}F_3N_5O_5$: C, 68.08; H, 5.84; N, 8.82. found: C, 67.94; H, 5.90; N, 8.64.

Examples 141-171, shown in the following table, were prepared using the procedure of Example 6, except that N-benzyloxycarbonyl-D-aspartic acid β-t-butyl ester monohydrate was replaced with Example 34, and 3-(trifluoromethyl)benzyl amine was replaced with the appropriate amine; all listed Examples exhibited an ¹H NMR spectrum consistent with the assigned structure.

| Example | A' |
|---|---|
| 141 | benzylamino |
| 142 | (2-methylbenzyl)amino |
| 143 | (3-methylbenzyl)amino |
| 144 | (4-methylbenzyl)amino |
| 145 | (α-methylbenzyl)amino |
| 146 | N-benzyl-N-methylamino |
| 147 | N-benzyl-N-(t-butyl)amino |
| 148 | N-benzyl-N-butylamino |
| 149 | (3,5-dimethylbenzyl)amino |
| 150 | (2-phenylethyl)amino |
| 151 | dimethylamino |
| 152 | (3-trifluoromethoxybenzyl)amino |
| 153 | (3,4-dichlorobenzyl)amino |
| 154 | (3,5-dichlorobenzyl)amino |
| 155 | (2,5-dichlorobenzyl)amino |
| 156 | (2,3-dichlorobenzyl)amino |
| 157 | (2-fluoro-5-trifluoromethylbenzyl)amino |
| 158 | (4-fluoro-3-trifluoromethylbenzyl)amino |
| 159 | (3-fluoro-5-trifluoromethylbenzyl)amino |
| 160 | (2-fluoro-3-trifluoromethylbenzyl)amino |
| 161 | (4-chloro-3-trifluoromethylbenzyl)amino |
| 162 | indan-1-ylamino |
| 163 | 4-(2-hydroxybenzimidazol-1-yl)-piperidinyl |
| 164 | 3(S)-(tert-butylaminocarbonyl)-1,2,3,4-tetrahydroisoquinolin-2-yl |
| 165 | (3,3-dimethylbutyl)amino |
| 166 | 4-hydroxy-4-phenylpiperidinyl |
| 167 | (cyclohexylmethyl)amino |
| 168 | (2-phenoxyethyl)amino |
| 169 | 3,4-methylenedioxybenzylamino |
| 170 | 4-benzylpiperidinyl |
| 171 | (3-trifluoromethylphenyl)amino |

Examples 172-221R, shown in the following table, were prepared using the procedure of Example 6, except that N-benzyloxycarbonyl-D-aspartic acid 3-t-butyl ester monohydrate was replaced with Example 34A, and 3-(trifluoromethyl)benzyl amine was replaced with the appropriate amine; all listed Examples exhibited an ¹H NMR spectrum consistent with the assigned structure.

| Example | A' |
|---|---|
| 172 | (3-trifluoromethoxybenzyl)amino |
| 173 | (3,4-dichlorobenzyl)amino |
| 174 | (3,5-dichlorobenzyl)amino |
| 175 | (2,5-dichlorobenzyl)amino |
| 176 | (2,3-dichlorobenzyl)amino |
| 177 | (2-fluoro-5-trifluoromethylbenzyl)amino |
| 178 | (4-fluoro-3-trifluoromethylbenzyl)amino |
| 179 | (3-fluoro-5-trifluoromethylbenzyl)amino |
| 180 | (2-fluoro-3-trifluoromethylbenzyl)amino |
| 181 | (4-chloro-3-trifluoromethylbenzyl)amino |
| 182 | (2-trifluoromethylbenzyl)amino |
| 183 | (3-methoxybenzyl)amino |
| 184 | (3-fluorobenzyl)amino |
| 185 | (3,5-difluorobenzyl)amino |
| 186 | (3-chloro-4-fluorobenzyl)amino |
| 187 | (3-chlorobenzyl)amino |
| 188 | [3,5-bis(trifluoromethyl)benzyl]amino |
| 189 | (3-nitrobenzyl)amino |
| 190 | (3-bromobenzyl)amino |
| 191 | benzylamino |
| 192 | (2-methylbenzyl)amino |
| 193 | (3-methylbenzyl)amino |
| 194 | (4-methylbenzyl)amino |
| 195 | (α-methylbenzyl)amino |
| 196 | (N-methylbenzyl)amino |
| 197 | (N-tert-butylbenzyl)amino |
| 198 | (N-butylbenzyl)amino |
| 199 | (3,5-dimethylbenzyl)amino |
| 200 | (2-phenylethyl)amino |
| 201 | (3,5-dimethoxybenzyl)amino |
| 202 | (1R)-(3-methoxyphenyl)ethylamino |
| 203 | (1S)-(3-methoxyphenyl)ethylamino |
| 204 | (α,α-dimethylbenzyl)amino |
| 205 | N-methyl-N-(3-trifluoromethylbenzyl)amino |
| 206 | [(S)-α-methylbenzyl]amino |
| 207 | (1-phenylcycloprop-1yl)amino |
| 208 | (pyridin-2-ylmethyl)amino |
| 209 | (pyridin-3-ylmethyl)amino |
| 210 | (pyridin-4-ylmethyl)amino |
| 211 | (fur-2-ylmethyl)amino |
| 212 | [(5-methylfur-2-yl)methyl]amino |
| 213 | (thien-2-ylmethyl)amino |
| 214 | [(S)-1,2,3,4-tetrahydro-1-naphth-1-yl]amino |
| 215 | [(R)-1,2,3,4-tetrahydro-1-naphth-1-yl]amino |
| 216 | (indan-1-yl)amino |
| 217 | (1-phenylcyclopent-1-yl)amino |
| 218 | (α,α-dimethyl-3,5-dimethoxybenzyl)amino |
| 219 | (2,5-dimethoxybenzyl)amino |
| 220 | (2-methoxybenzyl)amino |
| 221 | (α,α,2-trimethylbenzyl)amino |
| 221A | N-methyl-3-Me-benzylamide |
| 221B | N-methyl-2,3-Cl-benzylamide |
| 221C | N-methyl-3-Cl-benzylamide |
| 221D | N-methyl-3-Br-benzylamide |
| 221E | N-methyl-3,5-Cl-benzylamide |
| 221F | (R)-1-(3-trifluorophenyl)ethylamide |

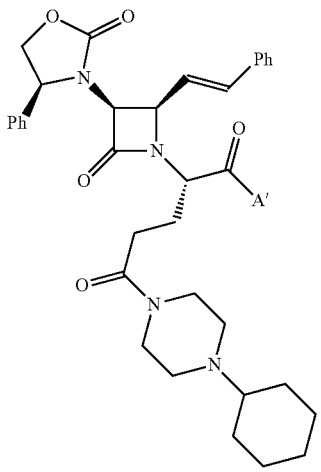

| Example | A' |
|---|---|
| 221G | 1-phenyl-cyclohexylamide |
| 221H | 1-(2-fluorophenyl)-cyclopentylamide |
| 221I | 1-(4-fluorophenyl)-cyclopentylamide |
| 221J | 4-CF3-benzylamide |
| 221K | α-phenyl-benzylamide |
| 221L | 3-phenyl-benzylamide |
| 221M | dibenzylamide |
| 221N | 1-naphthalene-methylamide |

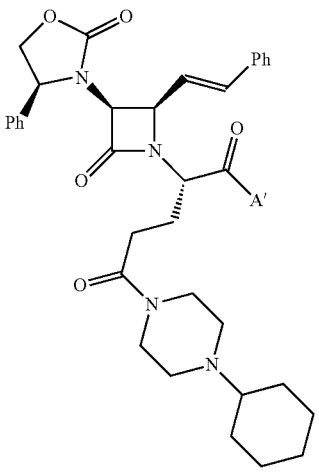

| Example | A' |
|---|---|
| 221O | 1,2,3,4-tetrahydro-isoquinolinamide |
| 221P | indan-2-ylamino |
| 221Q | α-(2-OH-ethyl)benzylamide |
| 221R | (S)-indan-1-ylamino |

The compounds shown in the following table were prepared according to the processes described herein.

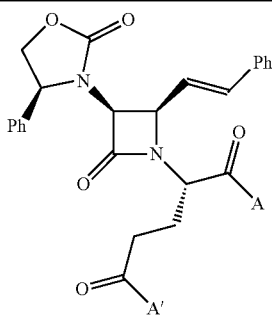

| Example | A | A' |
|---|---|---|
| 221S | (R)-1-indanylamino | 4-cyclohexylpiperazinyl |
| 221T | (αR)-α-(t-butoxycarbonylmethyl)benzylamino | 4-cyclohexylpiperazinyl |
| 221U | (R)-1,2,3,4-tetrahydro-1-naphtylamino | 4-(2-morpholinoethyl)piperazinyl |
| 221V | (R)-1,2,3,4-tetrahydro-1-naphtylamino | 2-dimethylaminoethylamino |
| 221W | (R)-1,2,3,4-tetrahydro-1-naphtylamino | 4-(2-phenylethyl)homopiperazinyl |
| 221X | (R)-1,2,3,4-tetrahydro-1-naphtylamino | 2-(1-piperidyl)ethylamino |
| 221Y | (R)-1,2,3,4-tetrahydro-1-naphtylamino | (S)-2-(1-pyrrolidinylmethyl)pyrrolidinyl |
| 221Z | (R)-1,2,3,4-tetrahydro-1-naphtylamino | 2-(1-pyrrolidinyl)ethylamino |
| 221AA | (R)-1,2,3,4-tetrahydro-1-naphtylamino | 4-(1-piperidyl)piperidinyl |
| 221AB | 3-CF3-benzylamino | 4-n-butylpiperazinyl |
| 221AC | 3-CF3-benzylamino | 4-ethylpiperazinyl |
| 221AD | (R)-1,2,3,4-tetrahydro-1-naphtylamino | (R)-1-benzylpyrrolidin-3-ylamino |
| 221AE | (R)-1,2,3,4-tetrahydro-1-naphtylamino | quinuclidin-3-ylamino |
| 221AF | (R)-1,2,3,4-tetrahydro-1-naphtylamino | 4-methylhomopiperazinyl |
| 221AG | (R)-1,2,3,4-tetrahydro-1-naphtylamino | 2-pyrrolylphenylamino |
| 221AH | (R)-1,2,3,4-tetrahydro-1-naphtylamino | morpholin-4-ylethylamino |
| 221AI | (R)-1,2,3,4-tetrahydro-1-naphtylamino | (S)-1-ethylpyrrolidin-2-ylaminomethyl |
| 221AJ | (R)-1,2,3,4-tetrahydro-1-naphtylamino | (R)-1-ethylpyrrolidin-2-ylaminomethyl |
| 221AK | (R)-1,2,3,4-tetrahydro-1-naphtylamino | (S)-1-butoxycarbonylpyrrolidin-3-ylamino |
| 221AL | (R)-1,2,3,4-tetrahydro-1-naphtylamino | quinolin-3-ylamino |
| 221AM | 1-(3-fluorophenyl)-cyclopentylamino | 4-cyclohexylpiperazinyl |
| 221AN | 1-(4-chlorophenyl)-cyclopropylamino | 4-cyclohexylpiperazinyl |
| 221AO | 1-(4-methoxyphenyl)-cyclopropylamino | 4-cyclohexylpiperazinyl |
| 221AP | 1-(4-methylphenyl)-cyclopropylamino | 4-cyclohexylpiperazinyl |
| 221AQ | 1-(4-chlorophenyl)-cyclopentylamino | 4-cyclohexylpiperazinyl |
| 221AS | 1-(4-methylphenyl)-cyclopentylamino | 4-cyclohexylpiperazinyl |

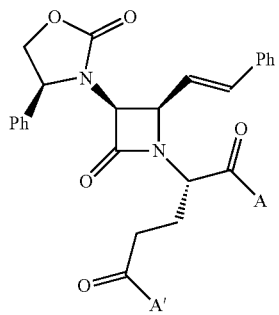

| Example | A | A' |
|---|---|---|
| 221AT | (R)-1,2,3,4-tetrahydro-1-naphtylamino | 3-(4-chlorophenyl)isoxazolin-5-ylamino |
| 221AU | 1-phenylcyclopentylamino | 4-(1-pyrrolidyl)piperidinyl |
| 221AV | indolinyl | 4-cyclohexylpiperazinyl |
| 221AW | 5-indanylamino | 4-cyclohexylpiperazinyl |
| 221AX | 1-phenylcyclopentylamino | 4-[3-((R)-Boc-amino)-1-pyrrolidyl)piperidinyl |
| 221AY | 4-indanylamino | 4-cyclohexylpiperazinyl |
| 221AZ | 1-phenylcyclopentylamino | (3R)-4-(3-chloroammoniumpyrrolidinyl)piperdinyl |
| 221BA | (R)-1,2,3,4-tetrahydro-1-naphtylamino | 4-(2-fluorophenyl)piperazinyl |
| 221BB | (R)-1,2,3,4-tetrahydro-1-naphtylamino | 4-(3-chlorophenyl)piperazinyl |
| 221BC | (R)-1,2,3,4-tetrahydro-1-naphtylamino | 4-(4-fluorophenyl)piperazinyl |
| 221BD | (R)-1,2,3,4-tetrahydro-1-naphtylamino | 4-ethylpiperazinyl |
| 221BE | (R)-1,2,3,4-tetrahydro-1-naphtylamino | 4-phenylpiperazinyl |
| 221BF | (R)-1,2,3,4-tetrahydro-1-naphtylamino | 4-benzylpiperazinyl |
| 221BG | (R)-1,2,3,4-tetrahydro-1-naphtylamino | 4-methylpiperazinyl |
| 221BH | (R)-1,2,3,4-tetrahydro-1-naphtylamino | 4-(2-methoxyphenyl)piperazinyl |
| 221BI | (R)-1,2,3,4-tetrahydro-1-naphtylamino | 4-(3-OH-n-propyl)piperazinyl |
| 221BJ | (R)-1,2,3,4-tetrahydro-1-naphtylamino | 4-(4-hydroxyphenyl)piperazinyl |

Examples 135-140, shown in the following table, were prepared using the procedure of Example 6, except that N-benzyloxycarbonyl-D-aspartic acid β-t-butyl ester monohydrate was replaced with Example 33, and 3-(trifluoromethyl)benzyl amine was replaced with the appropriate amine; all listed Examples exhibited an $^1$H NMR spectrum consistent with the assigned structure.

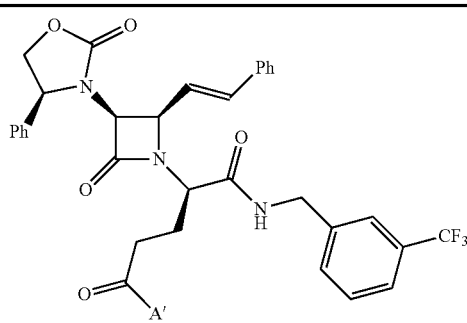

| Example | A' |
|---|---|
| 135 | 4-(piperidinyl)piperidinyl |
| 136 | 4-(2-phenylethyl)piperazinyl |
| 137 | 4-butylpiperazinyl |
| 138 | 4-isopropylpiperazinyl |
| 139 | 4-cyclohexylpiperazinyl |
| 140 | 4-(cyclohexylmethyl)piperazinyl |

Example 140A

2(R)-(2-(3-trifluoromethylbenzyl)amino-1-ylcarbonyl)ethyl)-2-[3(S)-(4(S)-phenyloxazolidin-2-on-3-yl)-4(R)-(2-styryl)azetidin-2-on-1-yl]acetic acid N-(4-cyclohexyl)piperazinamide. Example 140A was prepared using the procedure of Example 6, except that N-benzyloxycarbonyl-D-aspartic acid β-t-butyl ester monohydrate was replaced with Example 34Q, and 3-(trifluoromethyl)benzylamine was replaced with 1-cyclohexyl-piperazine, and exhibited an $^1$H NMR spectrum consistent with the assigned structure.

Examples 226-230C, shown in the following table, were prepared using the procedure of Example 6, except that N-benzyloxycarbonyl-D-aspartic acid β-t-butyl ester monohydrate was replaced with Example 34F, and 3-(trifluoromethyl)benzyl amine was replaced with the appropriate amine; all listed Examples exhibited an $^1$H NMR spectrum consistent with the assigned structure.

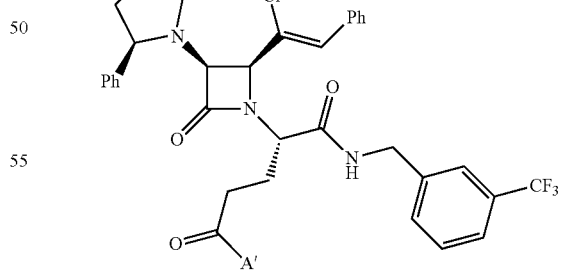

| Example | A' |
|---|---|
| 226 | 4-cyclohexylpiperazinyl |
| 227 | 4-(pyrrolidinyl)piperazinyl |
| 227A | 4-[2-(2-hydroxyethyloxy)ethyl]piperazinyl |
| 227B | 4-benzylpiperazinyl |
| 227C | 4-(3,4-methylendioxybenzyl)piperazinyl |
| 228 | 4-ethylpiperazinyl |

-continued

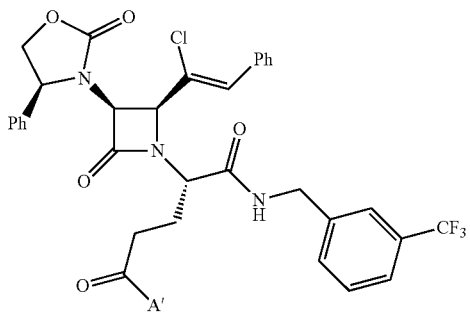

| Example | A' |
|---|---|
| 229 | 4-n-butylpiperazinyl |
| 230 | 4-isopropylpiperazinyl |
| 230A | 1-benzylpiperidin-4-ylamino |
| 230B | 4-(2-cyclohexylethyl)piperazinyl |
| 230C | 4[2-(morpholin-4-yl)ethyl]piperazinyl |

The following compounds were prepared according to the processes described herein:

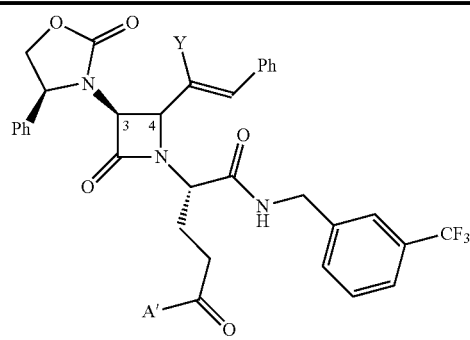

| Example | Y | C(3)-C(4) Stereochemistry | A' |
|---|---|---|---|
| 230D | F | not determined | 4-n-butylpiperazinyl |
| 230E | F | not determined | (R)-1-benzylpyrrolidin-3-amino |
| 230F | F | not determined | quinuclidin-3-ylamino |
| 230G | F | (3S,4R) | (S)-1-benzylpyrrolidin-3-amino |
| 230H | Cl | not determined | (R)-1-benzylpyrrolidin-3-amino |
| 230I | Cl | (3S,4R) | (R)-1-benzylpyrrolidin-3-amino |
| 230J | Cl | (3S,4R) | (S)-1-benzylpyrrolidin-3-amino |
| 230K | Cl | not determined | (S)-1-benzylpyrrolidin-3-amino |
| 230L | Br | not determined | 4-n-butylpiperazinyl |
| 230M | Br | not determined | 4-ethylpiperazinyl |

Example 86C

2(S)-[[4-(Piperidinyl)piperidinyl]carbonylmethyl]-2-[3(S)-(4(R)-phenyloxazolidin-2-on-3-yl)-4(R)-(2-styryl)azetidin-2-on-1-yl]acetic acid N-(3-trifluoromethylbenzyl)amide. Example 86C was prepared using the procedure of Example 6, except that N-benzyloxycarbonyl-D-aspartic acid 3-t-butyl ester monohydrate was replaced with Example 28A, and 3-(trifluoromethyl)benzyl amine was replaced with 4-(piperidinyl)piperidine, and exhibited an $^1$H NMR spectrum consistent with the assigned structure.

Example 231

2(R)-[[4-(Piperidinyl)piperidinyl]carbonylmethyl]-2-[3(S)-(4(S)-phenyloxazolidin-2-on-3-yl)-4(R)-(2'-methoxystyr-2-yl)azetidin-2-on-1-yl]acetic acid N-(3-trifluoromethylbenzyl)amide. Example 231 was prepared using the procedure of Example 6, except that N-benzyloxycarbonyl-D-aspartic acid β-t-butyl ester monohydrate was replaced with Example 34G, and 3-(trifluoromethyl)benzyl amine was replaced with 4-(piperidinyl)piperidine, and exhibited an $^1$H NMR spectrum consistent with the assigned structure.

Examples 232-233A, shown in the following table, were prepared using the procedure of Example 6, except that N-benzyloxycarbonyl-D-aspartic acid β-t-butyl ester monohydrate was replaced with Example 34H, and 3-(trifluoromethyl)benzyl amine was replaced with the appropriate amine; all listed Examples exhibited an $^1$H NMR spectrum consistent with the assigned structure.

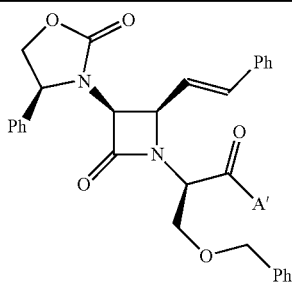

| Example | A' | α |
|---|---|---|
| 232 | 4-(piperidinyl)piperidinyl | D |
| 232A | (3-trifluorobenzyl)amino | D |
| 232B | 4-(3-trifluoromethylphenyl)piperazinyl | D or L |
| 232C | 4-(3-trifluoromethylphenyl)piperazinyl | D or L |
| 232D | 4-cyclohexylpiperazinyl | DL |
| 232E | 4-(piperidinylmethyl)piperidinyl | D |
| 233 | 4[2-(piperidinyl)ethyl]piperidinyl | D |
| 233A | 4-[(1-piperidyl)methyl]piperidinamide | D |

Example 234

(2RS)-[4-(piperidinyl)piperidinylcarbonyl]-2-methyl-2-[3(S)-(4(S)-phenyloxazolidin-2-on-3-yl)-4(R)-(2-styryl)azetidin-2-on-1-yl]acetic acid N-(3-trifluoromethylbenzyl)amide.

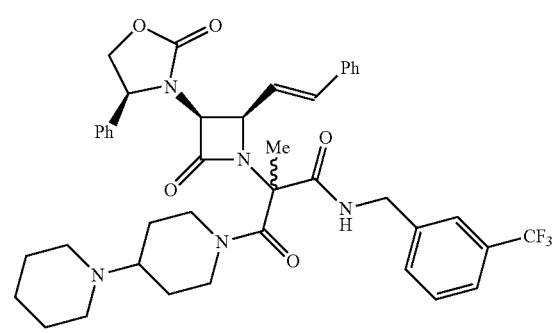 [SMILES: CC(C(=O)NCc1cccc(C(F)(F)F)c1)(C(=O)N1CCC(N2CCCCC2)CC1)N1C(=O)[C@@H](N2C(=O)OC[C@@H]2c2ccccc2)[C@H]1/C=C/c1ccccc1]

Example 37 (50 mg, 0.067 mmol) in tetrahydrofuran (4 mL) was treated sequentially with sodium hydride (4 mg, 0.168 mmol) and methyl iodide (6 μL, 0.094 mmol) at −78° C. The resulting mixture was slowly warmed to ambient temperature, and evaporated. The resulting residue was partitioned between dichloromethane and water, and the organic layer was evaporated. The resulting residue was purified by silica gel chromatography (95:5 chloroform/ methanol) to give 28 mg (55%) of the title compound as an off-white solid; MS (ES+): m/z=757 (M+).

Example 234A 4-(Piperidinyl)-piperidinyl 3(R)-[3(S)-(4(S)-phenyloxazolidin-2-on-3-yl)-3-methyl-4(R)-(styr-2-yl)azetidin-2-on-1-yl]-3-[(3-trifluoromethyl)phenylmethylaminocarbonyl]propanoic acid

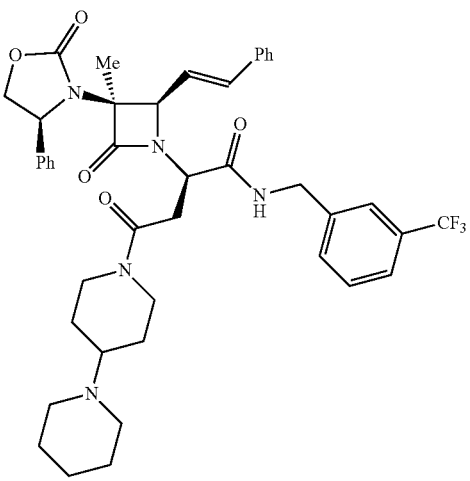 [SMILES: C[C@@]1(N2C(=O)OC[C@@H]2c2ccccc2)C(=O)N([C@H](CC(=O)N2CCC(N3CCCCC3)CC2)C(=O)NCc2cccc(C(F)(F)F)c2)[C@@H]1/C=C/c1ccccc1]

Using the procedure of Example 6, except that N-benzyloxycarbonyl-D-aspartic acid β-t-butyl ester monohydrate was replaced with the carboxylic acid of Example 34J and 3-(trifluoromethyl)benzyl amine was replaced with 4-(piperidinyl)piperidine, the title compound was prepared in quantitative yield; MS (m+H)+772.

The compounds shown in the following table were prepared according to the processes described herein.

| C(3)-C(4) Stereochemistry | R | A' |
|---|---|---|
| (3S,4R) | H | 4-(piperidyl)piperidinyl |
| (3S,4R) | Me | 4-(piperidyl)piperidinyl |
| not determined | H | 4-(piperidyl)piperidinyl |

Example 235

2(S)-[[(1-Benzylpiperidin-4-yl)amino]carbonylmethyl]-2-[3(S)-(4(S)-phenyloxazolidin-2-on-3-yl)-4(R)-(2-phenyleth-1-yl)azetidin-2-on-1-yl]acetic acid N-(3-trifluoromethylbenzyl)amide. Example 235 was prepared using the procedure of Example 8, except that N-benzyloxycarbonyl-L-aspartic acid β-t-butyl ester α-(3-trifluoromethyl)benzylamide was replaced with Example 63 (50 mg, 0.064 mmol) to give 40 mg (80%) of Example 235 as an off-white solid; Example 235 exhibited an $^1$H NMR spectrum consistent with the assigned structure.

Example 236

(2S)-[(4-cyclohexylpiperazinyl)carbonylethyl]-2-[3(S)-(4(S)-phenyloxazolidin-2-on-3-yl)-4(R)-(2-phenyleth-1-yl)azetidin-2-on-1-yl]acetic acid N-(3-trifluoromethylbenzyl)amide. Example 236 was prepared using the procedure of Example 8, except that N-benzyloxycarbonyl-L-aspartic acid β-t-butyl ester α-(3-trifluoromethyl)benzylamide was replaced with Example 110 (50 mg, 0.065 mmol) to give 42 mg (84%) of Example 236 as an off-white solid; Example 236 exhibited an $^1$H NMR spectrum consistent with the assigned structure.

Example 236A (2S)-[(4-cyclohexylpiperazinyl)carbonylethyl]-2-[3(S)-(4(S)-phenyloxazolidin-2-on-3-yl)-4(R)-(2-phenyleth-1-yl)azetidin-2-on-1-yl]acetic acid N—[(R)-1,2,3,4-tetrahydronaphth-1-yl]amide. Example 236A was prepared using the procedure of Example 8, except that N-benzyloxycarbonyl-L-aspartic acid β-t-butyl ester α-(3-trifluoromethyl)benzylamide was replaced with Example 215 (76 mg, 0.10 mmol) to give 69 mg (90%) of Example 236A as an off white solid. Example 236A exhibited an $^1$H NMR spectrum consistent with the assigned structure.

Example 237

2(R)-[[4-(Piperidinyl)piperidinyl]carbonylmethyl]-2-[3(S)-(4(S)-phenyloxazolidin-2-on-3-yl)-4(R)-(propen-1-yl)azetidin-2-on-1-yl]acetic acid N-(3-trifluoromethylbenzyl)amide. Example 237 was prepared using the procedure of Example 6, except that N-benzyloxycarbonyl-D-aspartic acid β-t-butyl ester monohydrate was replaced with Example 34K, and 3-(trifluoromethyl)benzyl amine was replaced with 4-(piperidinyl)piperidine. Example 237 exhibited an $^1$H NMR spectrum consistent with the assigned structure.

Example 238

(2S)-(Benzylthiomethyl)-2-[3(S)-(4(S)-phenyloxazolidin-2-on-3-yl)-4(R)-(2-styryl)azetidin-2-on-1-yl]acetic acid N-[4-[2-(piperid-1-yl)ethyl]piperidin-1-yl]amide. This Example was prepared using the procedure of Example 6, except that N-benzyloxycarbonyl-D-aspartic acid β-t-butyl ester monohydrate was replaced with the corresponding benzyl protected cysteine analog, and 3-(trifluoromethyl)benzyl amine was replaced with 4-[2-(piperid-1-yl)ethyl]piperidine.

Step 1. N-tButyloxycarbonyl-(S)-(benzyl)-D-cysteine-[4-(2-(1-piperidyl)ethyl)]piperidinenamide. N-tButyloxycarbonyl-(S)-Benzyl-N-(tbutyloxycarbonyl)-D-cysteine (0.289 g, 0.93 mmole) and 4-[2-(1-piperidyl)ethyl]piperidine (0.192 g, 0.98 mmole) in dichloromethane (20 mL) gave 0.454 g (quantitative yield) of Example X as an off-white solid. $^1$H NMR (CDCl$_3$) δ 0.89-1.15 (m, 2H); 1.39-1.44 (m, 16H); 1.54-1.61 (m, 4H); 1.62-1.71 (m, 1H); 2.21-2.35 (m, 5H); 2.49-2.58 (m, 2H); 2.66-2.74 (m, 1H); 2.79-2.97 (m, 1H); 3.67-3.76 (m, 3H); 4.48-4.51 (m, 1H); 4.72-4.75 (m, 1H); 5.41-5.44 (m, 1H); 7.19-7.34 (m, 5H).

Step 2. (S)-(benzyl)-D-cysteine-[4-(2-(1-piperidyl)ethyl)]piperidinenamide, dihydrochloride. N-tButyloxycarbonyl-(S)-(benzyl)-D-cysteine-[4-(2-(1-piperidyl)ethyl)]piperidinenamide (0.453 g, 0.93 mmole) was reacted overnight with acetyl chloride (0.78 mL, 13.80 mmole) in anhydrous methanol (15 mL). The title compound was obtained as an off-white solid by evaporating the reaction mixture to dryness (0.417 g, 97%). $^1$H NMR (CD$_3$OD) δ 0.94-1.29 (m, 2H); 1.49-1.57 (m, 1H); 1.62-1.95 (m, 10H); 2.65-2.80 (m, 2H); 2.81-2.97 (m, 4H); 3.01-3.14 (m, 2H); 3.50-3.60 (m, 3H); 3.81-3.92 (m, 2H); 4.41-4.47 (m, 2H); 7.25-7.44 (m, 5H).

Step 3. Using the general procedures described herein, the imine prepared from (S)-(benzyl)-D-cysteine-[4-(2-(1-piperidyl)ethyl)]piperidinenamide, dihydrochloride (0.417 g, 0.90 mmole) and cinnamaldehyde, in the presence on triethylamine (0.26 mL, 1.87 mmole), was combined with 2-(4(S)-phenyloxazolidin-2-on-3-yl) acetyl chloride (Example 1) to give 0.484 g (76%) of Example 238 as an off-white solid after recrytallization from dichloromethane/hexanes. $^1$H NMR (CDCl$_3$) δ 0.89-1.06 (m, 2H); 1.40-1.44 (m, 5H); 1.57-1.67 (m, 6H); 2.25-2.43 (m, 6H); 2.45-2.59 (m, 2H); 2.71-2.88 (m, 2H); 3.55-3.70 (m, 3H); 4.11-4.17 (m, 1H); 4.37-4.47 (m, 2H); 4.54-4.61 (m, 1H); 4.64-4.69 (m, 1H); 4.76-4.84 (m, 2H); 6.05-6.19 (m, 1H); 6.66-6.71 (m, 1H); 7.12-7.40 (m, 15H).

The following compounds are described

The following compounds are described

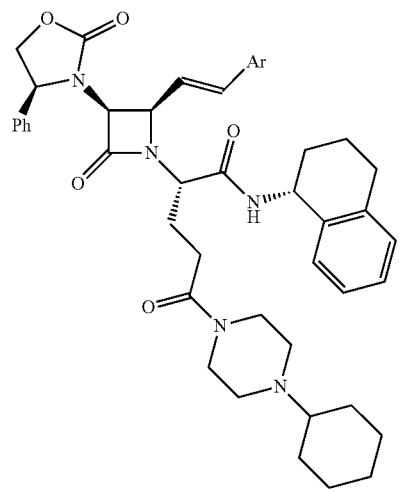

| Example | Ar |
|---------|-----|
| 257 | benzothiophen-7-yl |
| 254 | fur-2-yl |
| 255 | thien-2-yl |

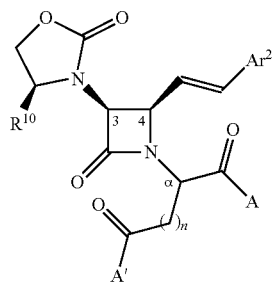

| Example | R$^{10}$ | Ar$^2$ | n | α | A | A' |
|---------|--------|--------|---|---|---|-----|
| 239 | Ph | Ph | 2 | L | 1-Ph-cyclopentylamino | 4-ethylpiperazin-1-yl |
| 240 | Ph | Ph | 2 | L | 1-Ph-cyclopentylamino | 4-benzylpiperazin-1-yl |
| 241 | Ph | Ph | 2 | L | (R)-1,2,3,4-tetrahydronaphth-1-ylamino | 4-cyclopentylpiperazin-1-yl |
| 242 | Ph | 3-MeO-Ph | 2 | L | (R)-1,2,3,4-tetrahydronaphth-1-ylamino | 4-cyclohexylpiperazin-1-yl |
| 243 | Ph | 3-Cl-Ph | 2 | L | (R)-1,2,3,4-tetrahydronaphth-1-ylamino | 4-cyclohexylpiperazin-1-yl |
| 244 | Ph | 3-Cl-Ph | 2 | L | 1-phenyl-cyclopent-1-ylamino | 4-cyclohexylpiperazin-1-yl |
| 245 | Ph | 3-F-Ph | 2 | L | (R)-1,2,3,4-tetrahydronaphth-1-ylamino | 4-cyclohexylpiperazin-1-yl |
| 246 | Ph | 3-CF$_3$-Ph | 2 | L | (R)-1,2,3,4-tetrahydronaphth-1-ylamino | 4-cyclohexylpiperazin-1-yl |
| 247 | Ph | 3-Cl-Ph | 1 | D | N-methyl-3-CF$_3$-benzylamino | 4-(1-piperidyl)piperidin-1-yl |
| 248 | Ph | 3-CN-Ph | 2 | L | (R)-1,2,3,4-tetrahydronaphth-1-ylamino | 4-cyclohexylpiperazin-1-yl |
| 249 | Ph | 3-NO$_2$-Ph | 2 | L | (R)-1,2,3,4-tetrahydronaphth-1-ylamino | 4-cyclohexylpiperazin-1-yl |
| 250 | Ph | 2-Cl-Ph | 2 | L | (R)-1,2,3,4-tetrahydronaphth-1-ylamino | 4-cyclohexylpiperazin-1-yl |
| 251 | 3-Cl-Ph | 3-Cl-Ph | 2 | L | (R)-1,2,3,4-tetrahydronaphth-1-ylamino | 4-cyclohexylpiperazin-1-yl |
| 252 | Ph | 3,5-Cl$_2$-Ph | 2 | L | (R)-1,2,3,4-tetrahydronaphth-1-ylamino | 4-cyclohexylpiperazin-1-yl |
| 253 | Ph | Ph | 1 | L | (S)-1-Ph-ethylamino | 4-(1-piperidyl)piperidin-1-yl |
| 256 | 3-Cl-Ph | Ph | 1 | D | (R)-1-Ph-ethylamino | 4-(1-piperidyl)piperidin-1-yl |
| 266 | Ph | 3-I-Ph | 1 | D | (R)-1-Ph-ethylamino | 4-(1-piperidyl)piperidin-1-yl |

The following compounds are described

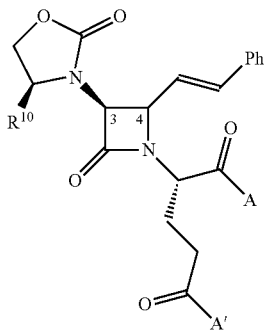

| Example | R[10] | Stereo-chemistry | A | A' |
|---|---|---|---|---|
| 258 | Ph | (3S,4R) | (R)-1,2,3,4-tetrahydronaphth-1-ylamino | 4-cycloheptylpiperazin-1-yl |
| 259 | Ph | (3S,4R) | (R)-1,2,3,4-tetrahydronaphth-1-ylamino | 4-(tetrahydrothiopyran-4-yl)piperazin-1-yl |
| 260 | Ph | (3R,4S) | 3-CF$_3$-benzylamino | 4-cyclohexylpiperazin-1-yl |
| 261 | Ph | (3S,4R) | 4-phenylpiperazin-1-yl | 3-F-5-CF$_3$-benzylamino |
| 262 | Ph | (3S,4R) | 4-(2-cyclohexylethyl)piperazin-1-yl | 3-F-5-CF$_3$-benzylamino |
| 263 | Ph | (3S,4R) | 4-(pyrid-2-yl)piperazin-1-yl | 3-F-5-CF$_3$-benzylamino |
| 264 | Ph | (3S,4R) | 4-(2-thien-2-ylethyl)piperazin-1-yl | 3-F-5-CF$_3$-benzylamino |
| 265 | 3-Cl-Ph | (3S,4R) | (R)-α-methylbenzylamino | 4-cyclohexylpiperazin-1-yl |

The following compounds are described

The following compounds are described

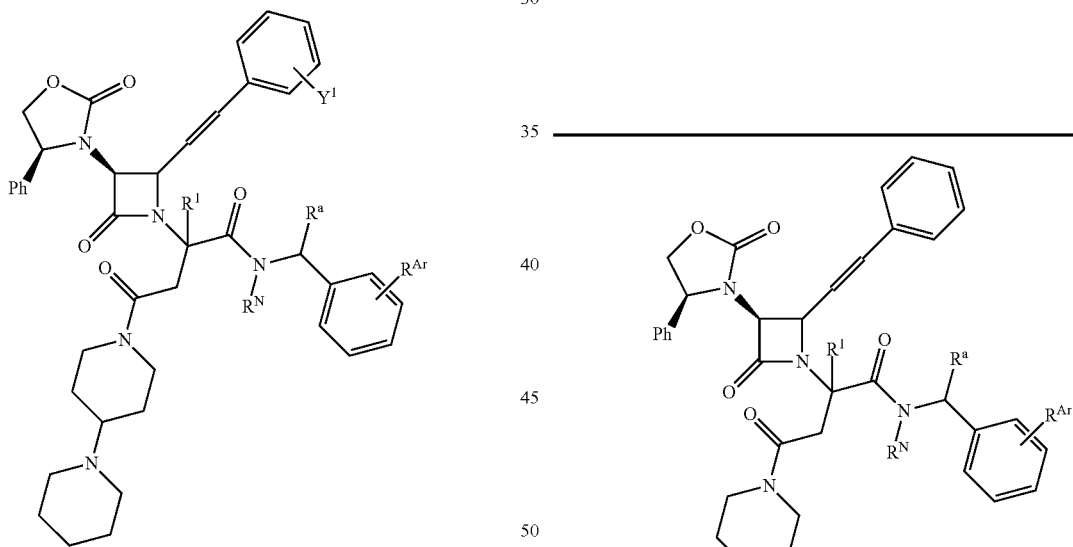

| Example | Y[1] | R[N] | R[a] | R[Ar] |
|---|---|---|---|---|
| 559 | 3-Cl | H | (R)-Me | H |
| 594 | 4-OH | H | (R)-Me | H |
| 597 | 3-NO$_2$ | H | (R)-Me | H |
| 600 | 3-NH$_2$ | H | (R)-Me | H |
| 606 | 3-Br | H | (R)-Me | H |
| 633 | 3-F | H | (R)-Me | H |
| 778 | 3-Me | H | (R)-Me | H |
| 623 | H | H | (R)-CF$_3$ | H |
| 626 | H | H | (S)-CF$_3$ | H |
| 682 | H | H | H | 2-Br |
| 677 | H | H | H | 2-F |
| 617 | 3-Br | Me | H | 3-CF$_3$ |

| Example | R[N] | R[a] | R[Ar] |
|---|---|---|---|
| 599 | Me | H | 3-CF$_3$ |
| 601 | H | (R)-Me | H |

The following compounds are described

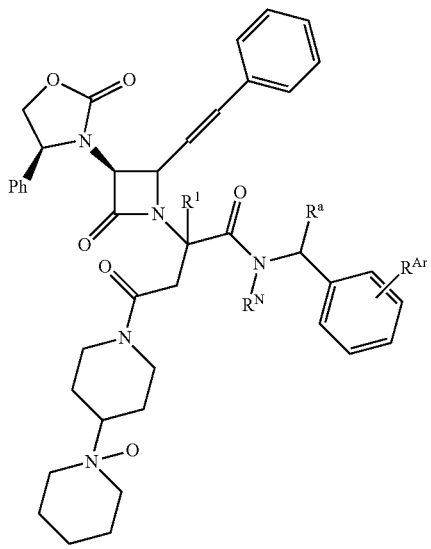

| Example | $R^N$ | $R^a$ | $R^{Ar}$ |
|---|---|---|---|
| 670 | Me | H | 3-CF$_3$ |
| 672 | H | (R)-Me | H |

The following table illustrates selected compounds further characterized by mass spectral analysis using FAB to observe the corresponding (M+H)$^+$ parent ion.

| Example | (m + H)$^+$/z |
|---|---|
| 37 | 744 |
| 38 | 766 |
| 39 | 766 |
| 40 | 718 |
| 41 | 704 |
| 42 | 744 |
| 42A | 772 |
| 44 | 758 |
| 63 | 780 |
| 85 | 766 |
| 86A | 786 |
| 86C | 758 |
| 88 | 772 |
| 91 | 759 |
| 95 | 780 |
| 96 | 824 |
| 104 | 732 |
| 110 | 772 |
| 111 | 800 |
| 112 | 803 |
| 120 | 786 |
| 120A | 800 |
| 120B | 732 |
| 120E | 788 |
| 132B | 758 |
| 133 | 758 |
| 134A | 786 |
| 134C | 780 |
| 134H | 772 |
| 136 | 794 |
| 137 | 746 |
| 138 | 732 |
| 139 | 772 |
| 174 | 772 |
| 175 | 772 |
| 176 | 772 |
| 177 | 790 |
| 179 | 790 |
| 180 | 790 |
| 182 | 772 |
| 183 | 734 |
| 184 | 722 |
| 185 | 740 |
| 186 | 756 |
| 187 | 738 |
| 188 | 840 |
| 189 | 749 |
| 190 | 782 |
| 191 | 704 |
| 192 | 718 |
| 193 | 718 |
| 199 | 732 |
| 200 | 718 |
| 201 | 764 |
| 202 | 748 |
| 203 | 748 |
| 205 | 786 |
| 206 | 718 |
| 207 | 730 |
| 208 | 705 |
| 209 | 705 |
| 210 | 705 |
| 211 | 694 |
| 212 | 708 |
| 213 | 710 |
| 214 | 744 |
| 215 | 744 |
| 216 | 7530 |
| 217 | 758 |
| 218 | 792 |
| 219 | 764 |
| 220 | 734 |
| 221 | 746 |
| 222 | 776 |
| 224 | 704 |
| 225 | 772 |
| 226 | 806 |
| 227 | 792 |
| 228 | 752 |
| 229 | 780 |
| 230 | 766 |
| 231 | 788 |
| 232 | 663 |
| 233 | 691 |
| 234 | 758 |
| 235 | 782 |
| 236 | 774 |

What is claimed is:

1. A method for treating post-traumatic stress disorder in a host animal, the method comprising administering to the host animal a therapeutically effective amount of one or more compounds of the formulae

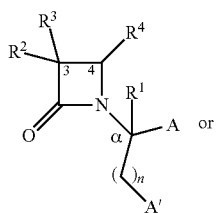

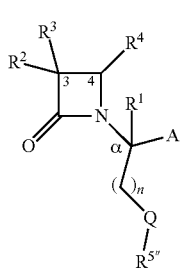

(II)

or salts thereof, wherein
A and A' are independently selected amides;
Q is oxygen; or Q is sulfur or disulfide, or an oxidized derivative thereof;
$R^{5''}$ is selected from hydrogen, alkyl, cycloalkyl, alkoxyalkyl, optionally substituted arylalkyl, optionally substituted heterocyclyl or optionally substituted heterocyclylalkyl, and optionally substituted aminoalkyl;
n is an integer selected from 0 to 3;
$R^1$ is hydrogen or $C_1$-$C_6$ alkyl;
$R^2$ is hydrogen, alkyl, alkenyl, alkynyl, alkoxy, alkylthio, halo, haloalkyl, cyano, formyl, alkylcarbonyl, or a substituent selected from the group consisting of —$CO_2R^8$, —$CONR^8R^{8'}$, and —$NR^8(COR^9)$; where $R^8$ and $R^{8'}$ are each independently selected from hydrogen, alkyl, cycloalkyl, optionally substituted aryl, or optionally substituted arylalkyl; or $R^8$ and $R^{8'}$ are taken together with the attached nitrogen atom to form a heterocyclyl group; and
where $R^9$ is selected from hydrogen, alkyl, cycloalkyl, alkoxyalkyl, optionally substituted aryl, optionally substituted arylalkyl, optionally substituted heteroaryl, optionally substituted heteroarylalkyl, and $R^8R^{8'}N$—($C_1$-$C_4$ alkyl);
$R^3$ is

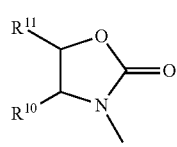

where $R^{10}$ and $R^{11}$ are each independently selected from the group consisting of hydrogen, optionally substituted alkyl, optionally substituted cycloalkyl, alkoxycarbonyl, alkylcarbonyloxy, optionally substituted aryl, optionally substituted arylalkyl, optionally substituted arylalkyloxy, optionally substituted arylalkylcarbonyloxy, diphenylmethoxy, and triphenylmethoxy; and
$R^4$ is optionally substituted arylalkyl, optionally substituted arylhaloalkyl, optionally substituted arylalkoxyalkyl, optionally substituted arylalkenyl, optionally substituted arylhaloalkenyl, or optionally substituted arylalkynyl;
where each optional substituent in each instance is independently of the formula $(CH_2)_xZ^X$, where x is an integer from 0-6 and $Z^X$ is selected from halogen, hydroxy, alkanoyloxy, optionally substituted aroyloxy, alkyl, alkoxy, cycloalkyl, cycloalkoxy, alkenyl, alkynyl, haloalkyl, haloalkoxy, halocycloalkyl, halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from $CO_2R^{40}$ and $CONR^5R^6$, where $R^{40}$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

2. The method of claim 1 wherein the patient also has one or more impulse control or anger disorders, one or more general anxiety disorders or related anxiety disorders, or one or more depression disorders, or a combination thereof.

3. The method of claim 1 wherein the compound is selective for the V1a receptor.

4. The method of claim 1 wherein the compound is of the formula (I)

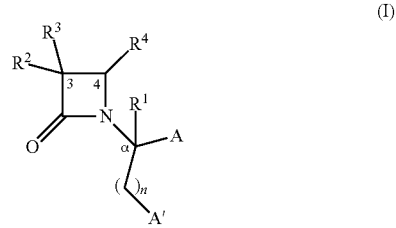

(I)

or a salt thereof.

5. The method of claim 4 wherein n is 1 or 2.

6. The method of claim 4 wherein A or A' is an amide of an optionally substituted arylalkylamine.

7. The method of claim 4 wherein A or A' is an amide of 1,2,3,4-tetrahydronaphth-1-ylamine, or A or A' is of the formula

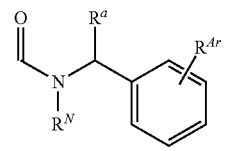

where $R^N$ is hydrogen or optionally substituted alkyl, or an amide prodrug forming group; $R^a$ is hydrogen or optionally substituted alkyl; and $R^{Ar}$ is hydrogen or one or more aryl substituents.

8. The method of claim 4 wherein A or A' is an amide of an optionally substituted pyrrolidinyl, piperidinyl, piperazinyl, or homopiperazinyl, where the substituent is heterocyclyl, heterocyclyl($C_1$-$C_4$)alkyl, ($C_3$-$C_{12}$)cycloalkyl, ($C_3$-$C_8$) cycloalkyl($C_1$-$C_4$)alkyl, aryl, or aryl($C_1$-$C_4$)alkyl.

9. The method of claim 4 wherein $R^1$ or $R^2$ is hydrogen, or $R^1$ and $R^2$ are both hydrogen.

10. The method of claim 1 wherein the compound is of the formula (II)

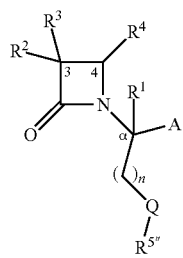

(II)

or a salt thereof, wherein n is an integer from 1 to 3.

11. The method of claim 10 wherein A is an amide of an optionally substituted arylalkylamine.

12. The method of claim 10 wherein A is an amide of 1,2,3,4-tetrahydronaphth-1-ylamine, or A is of the formula

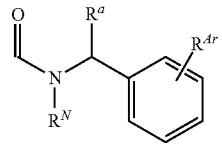

where $R^N$ is hydrogen or optionally substituted alkyl, or an amide prodrug forming group; $R^a$ is hydrogen or optionally substituted alkyl; and $R^{Ar}$ is hydrogen or one or more aryl substituents.

13. The method of claim 10 wherein A is an amide of an optionally substituted pyrrolidinyl, piperidinyl, piperazinyl, or homopiperazinyl, where the substituent is heterocyclyl, heterocyclyl($C_1$-$C_4$)alkyl, ($C_3$-$C_{12}$)cycloalkyl, ($C_3$-$C_8$)cycloalkyl($C_1$-$C_4$)alkyl, aryl, or aryl($C_1$-$C_4$)alkyl.

14. The method of claim 10 wherein Q is oxygen or sulfur.

15. The method of claim 10 wherein $R^{5'}$ is optionally substituted aryl($C_1$-$C_2$alkyl).

16. The method of claim 10 wherein $R^1$ or $R^2$ is hydrogen or both $R^1$ and $R^2$ are hydrogen.

17. The method of claim 10 wherein $R^3$ is

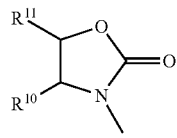

wherein $R^{10}$ and $R^{11}$ are each independently selected from the group consisting of hydrogen, optionally substituted alkyl, optionally substituted cycloalkyl, optionally substituted aryl, and optionally substituted arylalkyl.

18. The method of claim 1 wherein alkanoyloxy is $C_1$-$C_6$ alkanoyloxy, alkyl is $C_1$-$C_6$ alkyl, alkoxy is $C_1$-$C_6$ alkoxy, cycloalkyl is $C_3$-$C_8$ cycloalkyl, cycloalkoxy is $C_3$-$C_8$ cycloalkoxy, alkenyl is $C_2$-$C_6$ alkenyl, alkynyl is $C_2$-$C_6$ alkynyl, haloalkyl is $C_1$-$C_6$ haloalkyl, haloalkoxy is $C_1$-$C_6$ haloalkoxy, halocycloalkyl is $C_3$-$C_8$ halocycloalkyl, and halocycloalkoxy is $C_3$-$C_8$ halocycloalkoxy.

19. The method of claim 4 wherein $R^3$ is

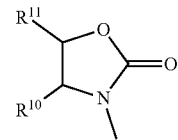

where $R^{11}$ is hydrogen; and $R^{10}$ is optionally substituted alkyl, optionally substituted cycloalkyl, optionally substituted aryl, or optionally substituted arylalkyl.

20. The method of claim 1 wherein $R^4$ is optionally substituted arylalkenyl or optionally substituted arylhaloalkenyl.

21. The method of claim 1 wherein the compound is of the formula

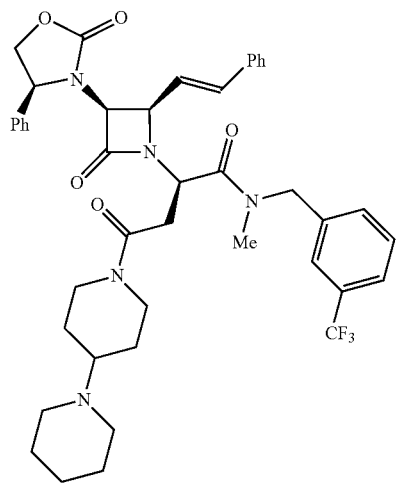 [SMILES: CN(Cc1cccc(C(F)(F)F)c1)C(=O)[C@@H](CC(=O)N1CCC(N2CCCCC2)CC1)N1C(=O)[C@@H](N2C(=O)OC[C@@H]2c2ccccc2)[C@H]1/C=C/c1ccccc1]

or a pharmaceutically acceptable salt thereof.

22. The method of claim 1 wherein the compound is of the formula

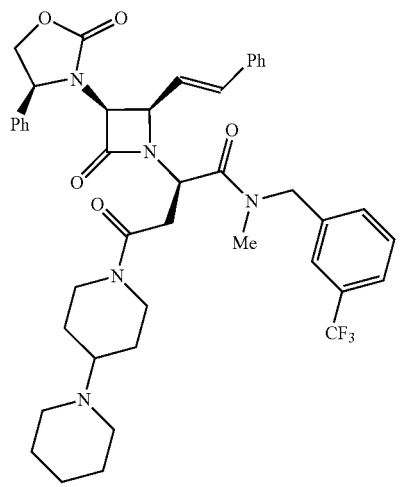 [SMILES: CN(Cc1cccc(C(F)(F)F)c1)C(=O)[C@@H](CC(=O)N1CCC(N2CCCCC2)CC1)N1C(=O)[C@@H](N2C(=O)OC[C@@H]2c2ccccc2)[C@H]1/C=C/c1ccccc1]

in a pharmaceutically acceptable salt form.

23. The method of claim 22 wherein the salt form is a hydrochloride salt form.

* * * * *

UNITED STATES PATENT AND TRADEMARK OFFICE
CERTIFICATE OF CORRECTION

PATENT NO. : 10,953,001 B2
APPLICATION NO. : 15/987053
DATED : March 23, 2021
INVENTOR(S) : Michael J. Brownstein It is certified that error appears in the above-identified patent and that said Letters Patent is hereby corrected as shown below:

In the Claims

In Claim 1, Lines 64 - 65, "halocycloalkoxy, halocycloalkoxy, amino," should read
– halocycloalkoxy, amino –.

Signed and Sealed this
Third Day of September, 2024

Katherine Kelly Vidal
*Director of the United States Patent and Trademark Office*